(12) United States Patent
Cristau et al.

(10) Patent No.: US 7,943,774 B2
(45) Date of Patent: May 17, 2011

(54) HETEROCYCLYL-SUBSTITUTED THIAZOLES AS CROP PROTECTION AGENTS

(75) Inventors: Pierre Cristau, Köln (DE); Nicola Rahn, Düsseldorf (DE); Stefan Herrmann, Langenfeld (DE); Tomoki Tsuchiya, Düsseldorf (DE); Ulrike Wachendorff-Neumann, Neuwied (DE); Arnd Voerste, Köln (DE); Jürgen Benting, Leichlingen (DE); Pierre Wasnaire, Düsseldorf (DE); Sebastian Hoffmann, Neuss (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 12/568,961

(22) Filed: Sep. 29, 2009

(65) Prior Publication Data
US 2010/0137245 A1 Jun. 3, 2010

(30) Foreign Application Priority Data
Oct. 1, 2008 (EP) .................................... 08165625

(51) Int. Cl.
| C07D 417/04 | (2006.01) |
|---|---|
| C07D 417/14 | (2006.01) |
| C07D 277/22 | (2006.01) |
| C07D 277/30 | (2006.01) |
| C07D 211/16 | (2006.01) |
| C07D 211/32 | (2006.01) |
| C07D 403/04 | (2006.01) |
| A61K 31/397 | (2006.01) |
| A61K 31/426 | (2006.01) |
| A61K 31/55 | (2006.01) |
| A61K 31/454 | (2006.01) |
| A61K 31/427 | (2006.01) |

(52) U.S. Cl. ........ 546/209; 546/193; 546/199; 548/204; 540/603; 514/210.18; 514/217.04; 514/217.1; 514/318; 514/326; 514/365

(58) Field of Classification Search ........................ None
See application file for complete search history.

(56) References Cited

U.S. PATENT DOCUMENTS
| 4,245,432 | A | 1/1981 | Dannelly |
|---|---|---|---|
| 4,272,417 | A | 6/1981 | Barke et al. |
| 4,808,430 | A | 2/1989 | Kouno |
| 5,876,739 | A | 3/1999 | Turnblad et al. |
| 6,372,967 | B1 | 4/2002 | Mariani et al. |
| 6,576,455 | B1 | 6/2003 | Kakefuda et al. |
| 2002/0115565 | A1 | 8/2002 | Asrar et al. |
| 2003/0176428 | A1 | 9/2003 | Schneidersmann et al. |
| 2006/0135501 | A1 | 6/2006 | Knox et al. |
| 2007/0054939 | A1 | 3/2007 | Guedat et al. |
| 2007/0074303 | A1 | 3/2007 | McCutchen et al. |
| 2008/0261979 | A1 | 10/2008 | Keil et al. |
| 2009/0054475 | A1 | 2/2009 | Chen et al. |
| 2009/0156592 | A1 | 6/2009 | Pasteris et al. |
| 2009/0238798 | A1 | 9/2009 | Bogdanova et al. |

FOREIGN PATENT DOCUMENTS
| EP | 1 832 586 A1 | 12/2007 |
|---|---|---|
| EP | 2 030 974 A1 | 4/2009 |
| WO | 02/080675 A1 | 10/2002 |
| WO | 2006/032322 A1 | 3/2006 |
| WO | 2007/014290 A2 | 2/2007 |
| WO | 2007/104558 A1 | 9/2007 |
| WO | 2007/115805 A2 | 10/2007 |
| WO | 2008/013925 | 1/2008 |
| WO | 2008/013925 A2 | 1/2008 |
| WO | 2008/091580 | 7/2008 |
| WO | 2008/091580 A2 | 7/2008 |
| WO | 2008/091594 A2 | 7/2008 |
| WO | 2009/055514 A2 | 4/2009 |

OTHER PUBLICATIONS

"An Alkoxyaryltriflouroperiodinane. A Stable Heterocyclic Derivative of Pentacoordinated Organoiodine(V)1," Journal of the American Chemical Society, 100:1, Jan. 4, 1978, pp. 300-301.
Amey et al., "Synthesis and Reactions of Stable Alkoxyaryltrifluoroperiodinanes.1 A "Tamed" Analogue of Iodine Pentafluoride for Use in Oxidations of Amines, Alcohols, and Other Species," Journal of the American Chemical Society, 101:18, Aug. 29, 1979, pp. 5294-5299.
Dess et al., "A Useful 12-I-5 Triacetoxyperiodinane (the Dess-Martin Periodinane) for the Selective Oxidation of Primary or Secondary Alcohols and a Variety of Related 12-I-5 Species1a," Journal of the American Chemical Society, 1991, 113, pp. 7277-7287.
Tojo et al., "Oxidation of Alcohols to Aldehydes and Ketones," Springer Berlin, 2006, pp. 1-97.
Maryanoff et al., "The Wittig Olefination Reaction and Modifications Involving Phosphoryl-Stabilized Carbanions. Sterochemistry, Mechanism, and Selected Synthetic Aspects," Chem. Rev., 1989, 89, pp. 863-927.
Julia et al., "Synthesis a L'aide de Sulvones v(+)—Methode de Synthese Generale de Doubles Liaisons," Tetrahedrom Letters No. 49, 1973, pp. 4833-4836.
Peterson, "A Carbonyl Olefination Reaction Using Silyl-Substituted Organometallic Compounds," The Journal of Organic Chemistry, 1968, 33, pp. 780-784.

(Continued)

Primary Examiner — Kamal A Saeed
Assistant Examiner — Nyeemah Grazier
(74) Attorney, Agent, or Firm — Baker Donelson Bearman, Caldwell & Berkowitz, PC

(57) ABSTRACT

Heterocyclyl-substituted thiazoles of the formula (I),

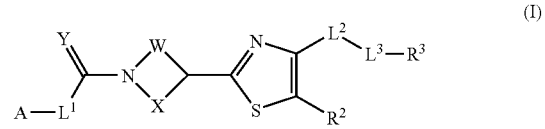

in which the symbols have the meanings given in the description, and also to the agrochemically active salts thereof, and their use for controlling phytopathogenic harmful fungi, and also processes for preparing compounds of the formula (I).

10 Claims, No Drawings

OTHER PUBLICATIONS

Corey et al., "A Synthetic Method for Formyl-Ethynyl Conversion (RCHO-RC=CH or RC=CR')," Tetrahedron Letters No. 36, 1972, pp. 3769-3772.

Brown et al., "A Convenient Synthesis of Dimethyl (Diazomethyl)phosphonate (Seyferth/Gilbert Reagent)," J. Org. Chem., 1996, 61, pp. 2540-2541.

Liepold et al., "Further Improvements of the Synthesis of Alkynes from Aldehydes," Synthesis, 2004, No. 1, pp. 59-62.

Eckhardt et al., "The First Applications of Cabene Ligands in Cross-Couplings of Alkyl Electrophiles: Sonogashira Reactions of Unactivated Alkyl Bromides and Iodides," J. Am. Chem. Soc., 2003, 125, pp. 13642-13643.

"Palladium-Catalyzed Heck Alkynylation of Benzyl Chlorides," Synlett, 2006, No. 18, pp. 2941-2946.

Nicolaou et al., "Synthesis and Biological Evaluation of 12,13-Cyclopropyl and 12,13-Cyclobutyl Epothilones," ChemBioChem, 2001, No. 1, pp. 69-75.

Iso et al., "Synthesis and Structure—Activity Relationships of 3-[(2-Methyl-1,3-thiazol-4-yl)ethynyl]pyridine Analogues as Potent, Noncompetitive Metabotropic Glutamate Receptor Subtype 5 Antagonists; Search for Cocaine Medications," J. Med. Chem. 2006, 49, pp. 1080-1100.

Thomsen et al., "Thiation with 2,4-Bis(4-Methoxyphenyl)-1,3,2,4-Dithiadiphosphetane 2,4-Disulfide: N-Methylthiopyrrolidone," Organic Synthesis, vol. 7, 1990, pp. 372-375.

Erian et al., "The Chemistry of a-Haloketones and Their Utility in Heterocyclic Synthesis," Molecules, 2003, 8, pp. 793-865.

Babu et al., "Synthesis, Antifungal Activity, and Structure—Activity Relationships of Coruscanone A Analogues," J. Med. Chem., 2006, 49, pp. 7877-7886.

"Selective a-Bromination of an Aralkyl Ketone with Phenyltrimethylammonium Tribromide: 2-bromoacetyl-6-methoxynaphthalene and 2,2-dibromoacetyl-6-methoxynaphthalene," Organic Syntheses, vol. 6, 1988, pp. 175-178.

"Selective a-Bromination of an Aralkyl Ketone with Phenyltrimethylammonium Tribromide: 2-bromoacety1-6-methoxynaphthalene and 2,2-dibromoacetyl-6-methoxynaphthalene," Organic Syntheses, vol. 53, 1973, pp. 111-115.

Green et al., "Mercury-Based Methods," Protective Groups in Organic Synthesis, Third Edition, pp. 494-653, (1999).

Deng et al., "Organolithium-Mediated Diversification of Peptide Thiazoles," Organic Letters, 2005, vol. 7, No. 2, pp. 299-301.

Jiang et al., "Synthesis of Diode Molecules and Their Sequential Assembly to Control Electron Transport," Angew. Chem. Int. Ed., 2004, 43, pp. 4471-4475.

Moreno et al., "A Simple Route to New Phenanthro- and Phenanthroid-Fused Thiazoles by a PIFA-Mediated (Hetero)biaryl Coupling Reaction," Eur. J. Org. Chem., 2002, pp. 2126-2135.

Montalbetti et al., "Amide bond formation and peptide coupling," Tetrahedron, 61, 2006, 10827-10852.

Jensen et al., "Studies on Amino Acids and Peptides XII Synthesis of Thiated Analogues of Boc-S-Ala-Aib-S-Ala-OMe and Ac-S-Ala-Aib-S-Ala-Ome," Tetrahedron, vol. 42, No. 23, 1986, pp. 6555-6564.

Jones et al., "The Synthesis of Unusual Tetrahydropyrimidine Amino Acids," Tetrahedron Letters, vol. 34, No. 46, 1993, pp. 7459-7462.

Wegler, "Chemie der Pflanzenschutz—und Schadlingsbekampfungsmittel," Bd. 2, Springer Verlag, 1970, s. pp. 401-412.

HETEROCYCLYL-SUBSTITUTED THIAZOLES AS CROP PROTECTION AGENTS

CROSS REFERENCE TO RELATED APPLICATIONS

This application claims priority to European Application 08165625.8 filed Oct. 1, 2008, the content of which is incorporated herein by reference in its entirety.

BACKGROUND OF THE INVENTION

1. Field of the Invention

Heterocyclyl-Substituted Thiazoles as Crop Protection Agents

The invention relates to heterocyclyl-substituted thiazoles and their agrochemically active salts, to their use and to methods and compositions for controlling phytopathogenic harmful fungi in and/or on plants or in and/or on seed of plants, to processes for preparing such compositions and treated seed and also to their use for controlling phytopathogenic harmful fungi in agriculture, horticulture and forestry, in animal husbandry, in the protection of materials and in the domestic and hygiene field. The present invention furthermore relates to a process for preparing heterocyclyl substituted thiazoles.

2. Description of Related Art

It is already known that certain heterocyclyl-substituted thiazoles can be employed as fungicidal crop protection agents (see WO 07/014,290, WO 08/013,925, WO 08/013,622, WO 08/091,594, WO 08/091,580, WO 09/055,514). However, the fungicidal activity of these compounds is, in particular at low application rates, not always sufficient.

Since the ecological and economic demands made on modern crop protection agents are increasing constantly, for example with respect to activity spectrum, toxicity, selectivity, application rate, formation of residues and favourable manufacture, and there can furthermore be problems, for example, with resistance, there is a constant need to develop novel crop protection agents, in particular fungicides which, at least in some areas, have advantages over the known fungicides.

SUMMARY OF THE INVENTION

Surprisingly, it has now been found that the present heterocyclyl-substituted thiazoles solve at least some aspects of the objects mentioned and are suitable for use as crop protection agents, in particular as fungicides.

Some heterocyclyl-substituted thiazoles are already known as pharmaceutically active compounds (see, for example, EP 1832586, WO 04/058750, WO 04/058751, WO 05/003128, WO 06/032322, WO 07/104,558, WO 07/115,805, WO 08/083,238), but not their surprising fungicidal activity.

The invention provides compounds of the formula (I),

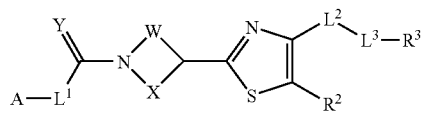

(I)

in which the symbols have the following meanings:

A represents methyl or

A represents unsubstituted or substituted phenyl, where the substituents independently of one another are selected from the list below cyano, nitro, halogen, $C_1$-$C_6$-alkyl, $C_1$-$C_3$-haloalkyl, $C_3$-$C_6$-cycloalkyl, $C_3$-$C_6$-halocycloalkyl, $C_4$-$C_{10}$-cycloalkylalkyl, $C_4$-$C_{10}$-alkylcycloalkyl, $C_5$-$C_{10}$-alkylcycloalkylalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_2$-alkyl)silyl, benzyl, phenyl, hydroxyl, $C_1$-$C_4$-alkoxy, $C_1$-$C_4$-haloalkoxy, $OCH_2OCH_3$, SH, $C_1$-$C_4$-alkylthio, $C_1$-$C_6$-haloalkylthio, CHO, COOH, ($C_1$-$C_4$-alkoxy)carbonyl, $CONR^6R^7$, $CR^6$=$NOR^7$, ($C_1$-$C_4$-alkyl)carbonyl, ($C_1$-$C_4$-haloalkyl)carbonyl, ($C_1$-$C_4$-alkyl)carbonyloxy, ($C_1$-$C_4$-alkyl)carbonylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, $NR^6R^7$, $NR^6COR^7$, $SF_5$, $SO_2NR^6R^7$, $C_2$-$C_4$-alkoxyalkyl or 1-methoxycyclopropyl or A is an optionally benzo-fused unsubstituted or substituted 5- or 6-membered heteroaryl, where the substituents independently of one another are selected from the list below Substituents at Carbon:

cyano, nitro, halogen, $C_1$-$C_6$-alkyl, $C_1$-$C_3$-haloalkyl, $C_3$-$C_6$-cycloalkyl, $C_3$-$C_6$-halocycloalkyl $C_4$-$C_{10}$-cycloalkylalkyl, $C_4$-$C_{10}$-alkylcycloalkyl, $C_5$-$C_{10}$-alkylcycloalkylalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_2$-alkyl)silyl, benzyl, phenyl, hydroxyl, $C_1$-$C_4$-alkoxy, $C_1$-$C_4$-haloalkoxy, $OCH_2OCH_3$, SH, $C_1$-$C_4$-alkylthio, $C_1$-$C_6$-haloalkylthio, CHO, COOH, ($C_1$-$C_4$-alkoxy)carbonyl, $CONR^6R^7$, $CR^6$=$NOR^7$, ($C_1$-$C_4$-alkyl)carbonyl, ($C_1$-$C_4$-haloalkyl)carbonyl, ($C_1$-$C_4$-alkyl)carbonyloxy, ($C_1$-$C_4$-alkyl)carbonylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, $NR^6R^7$, $NR^6COR^7$, $SF_5$, $SO_2NR^6R^7$, $C_2$-$C_4$-alkoxyalkyl or 1-methoxycyclopropyl Substituents at Nitrogen:

hydroxyl, $NR^6R^7$, $C_1$-$C_6$-alkyl, $C_1$-$C_3$-haloalkyl, $C_3$-$C_6$-cycloalkyl, $C_3$-$C_6$-halocycloalkyl, $C_4$-$C_{10}$-alkylcycloalkyl, $C_2$-$C_6$-alkenyl, $C_2$-$C_6$-haloalkenyl, $C_2$-$C_6$-alkynyl, or $C_2$-$C_6$-haloalkynyl $L^1$ represents $(C(R^1)_2)_n$ where n=0 to 3

$R^1$ are identical or different and independently of one another represent hydrogen, halogen, $C_1$-$C_2$-alkyl, $C_1$-$C_2$-haloalkyl or cyano, with the provision that $L^1$ may contain at most two $R^1$ different from hydrogen Y represents sulphur or oxygen, W represents an unsubstituted or monosubstituted $C_1$- to $C_3$-carbon chain, where the substituent is selected from the group consisting of oxo, hydroxyl, cyano and $C_1$-$C_4$-alkyl X represents an unsubstituted or monosubstituted $C_1$- to $C_2$-carbon chain, where the substituent is selected from the group consisting of oxo, hydroxyl, cyano and $C_1$-$C_4$-alkyl $R^2$ represents hydrogen, $C_1$-$C_2$-alkyl, $C_1$-$C_2$-haloalkyl or halogen $L^2$ represents —$C(R^8)_2$—$C(R^8)_2$— or —$CR^9$=$CR^9$— or —C≡C—

$L^3$ represents a direct bond or $L^3$ represents a $C_1$- to $C_4$-carbon chain which may contain up to two substituents, where the substituents independently of one another are selected from the list below:
  halogen, $C_1$-$C_2$-alkyl, $C_1$-$C_2$-alkoxy, $C_1$-$C_2$-haloalkyl or $C_3$-$C_6$-cycloalkyl $R^3$ represents methyl, $C_1$-$C_2$-haloalkyl, —CH=CH$_2$, —C≡CH, or unsubstituted or monosubstituted $C_3$-$C_{10}$-cycloalkyl, where the substituent is selected from the list below:
  cyano, halogen, $C_1$-$C_6$-alkyl, $C_1$-$C_3$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_2$-alkyl)silyl, phenyl, hydroxyl, oxo, $C_1$-$C_6$-alkoxy, $C_1$-$C_6$-haloalkoxy, $C_2$-$C_6$-alkenyloxy, $C_2$-$C_6$-alkynyloxy, $C_1$-$C_6$-alkylthio or $C_1$-$C_6$-haloalkylthio, or $R^3$ represents unsubstituted or substituted phenyl, where the substituents independently of one another are selected from the list below:
  cyano, nitro, halogen, $C_1$-$C_6$-alkyl, $C_1$-$C_3$-haloalkyl, $C_3$-$C_6$-cycloalkyl, $C_3$-$C_6$-halocycloalkyl, $C_4$-$C_{10}$-cycloalkylalkyl, $C_4$-$C_{10}$-halocycloalkylalkyl, $C_4$-$C_{10}$-alkylcycloalkyl, $C_5$-$C_{10}$-alkylcycloalkylalkyl, $C_4$-$C_{10}$-cycloalkoxyalkyl, $C_2$-$C_6$-alkenyl, $C_2$-$C_6$-haloalkenyl, $C_3$-$C_8$-cycloalkenyl, $C_3$-$C_8$-halocycloalkenyl, $C_2$-$C_6$-alkynyl, $C_2$-$C_6$-haloalkynyl, $C_2$-$C_6$-alkoxyalkyl, $C_2$-$C_6$-haloalkoxyalkyl, $C_3$-$C_8$-alkoxyalkoxyalkyl, tri($C_1$-$C_2$-alkyl)silyl, benzyl, phenyl, hydroxyl, $C_1$-$C_6$-alkoxy, $C_2$-$C_6$-alkoxyalkoxy, $C_1$-$C_6$-haloalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_3$-$C_6$-cycloalkoxy, $C_3$-$C_6$-cycloalkyloxy, $C_3$-$C_6$-halocycloalkoxy, $C_4$-$C_{10}$-cycloalkylalkyloxy, $NR^6R^7$, SH, $SF_5$, $C_1$-$C_6$-alkylthio, $C_1$-$C_6$-haloalkylthio, $C_2$-$C_6$-alkylalkylthio, $C_3$-$C_6$-cycloalkylthio, CHO, COOH, ($C_1$-$C_6$-alkoxy)carbonyl, $CONR^6R^7$, $CR^6$=$NOR^7$, ($C_1$-$C_6$-alkyl)carbonyl, ($C_1$-$C_6$-haloalkyl)carbonyl, ($C_1$-$C_6$-alkyl)carbonyloxy, ($C_1$-$C_6$-haloalkyl)carbonyloxy, ($C_1$-$C_6$-alkyl)carbonylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $NR^6COR^7$ or $SO_2NR^6R^7$ or $R^3$ represents saturated or partially or fully unsaturated naphthyl or indenyl which may contain up to two substituents, where the substituents independently of one another are selected from the list below:
  cyano, halogen, $C_1$-$C_6$-alkyl, $C_1$-$C_3$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_2$-alkyl)silyl, phenyl, hydroxyl, $C_1$-$C_6$-alkoxy, $C_1$-$C_6$-haloalkoxy, $C_2$-$C_6$-alkenyloxy, $C_2$-$C_6$-alkynyloxy, $C_1$-$C_6$-alkylthio or $C_1$-$C_6$-haloalkylthio, or $R^3$ represents an unsubstituted or substituted 5- or 6-membered heteroaryl radical, where the substituents independently of one another are selected from the list below:
substituents at carbon: cyano, nitro, halogen, $C_1$-$C_6$-alkyl, $C_1$-$C_3$-haloalkyl, $C_3$-$C_6$-cycloalkyl, $C_3$-$C_6$-halocycloalkyl $C_4$-$C_{10}$-cycloalkylalkyl, $C_4$-$C_{10}$-alkylcycloalkyl, $C_5$-$C_{10}$-alkylcycloalkylalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_2$-alkyl)silyl, benzyl, phenyl, hydroxyl, $C_1$-$C_4$-alkoxy, $C_1$-$C_4$-haloalkoxy, $OCH_2OCH_3$, SH, $C_1$-$C_4$-alkylthio, $C_1$-$C_6$-haloalkylthio, COOH, ($C_1$-$C_4$-alkoxy)carbonyl, $CONR^6R^7$, ($C_1$-$C_4$-alkyl)carbonyl, ($C_1$-$C_4$-haloalkyl)carbonyl, ($C_1$-$C_4$-alkyl)carbonyloxy, ($C_1$-$C_4$-alkyl)carbonylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, $NR^6R^7$, $NR^6COR^7$, $SF_5$, $SO_2NR^6R^7$, $C_2$-$C_4$-alkoxyalkyl or 1-methoxycyclopropyl substituents at nitrogen: hydroxyl, $C_1$-$C_6$-alkyl, $C_1$-$C_3$-haloalkyl, $C_3$-$C_6$-cycloalkyl, $C_3$-$C_6$-halocycloalkyl, $C_4$-$C_{10}$-alkylcycloalkyl, $C_2$-$C_6$-alkenyl, $C_2$-$C_6$-haloalkenyl, $C_2$-$C_6$-alkynyl, $C_2$-$C_6$-haloalkynyl or phenyl or $R^3$ represents benzo-fused unsubstituted or substituted 5- or 6-membered heteroaryl which may contain up to two substituents, where the substituents independently of one another are selected from the list below:
substituents at carbon: cyano, nitro, halogen, $C_1$-$C_6$-alkyl, $C_1$-$C_3$-haloalkyl, $C_3$-$C_6$-cycloalkyl, $C_3$-$C_6$-halocycloalkyl $C_4$-$C_{10}$-cycloalkylalkyl, $C_4$-$C_{10}$-alkylcycloalkyl, $C_5$-$C_{10}$-alkylcycloalkylalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_2$-alkyl)silyl, benzyl, phenyl, hydroxyl, $C_1$-$C_4$-alkoxy, $C_1$-$C_4$-haloalkoxy, $OCH_2OCH_3$, SH, $C_1$-$C_4$-alkylthio, $C_1$-$C_6$-haloalkylthio, COOH, ($C_1$-$C_4$-alkoxy)carbonyl, $CONR^6R^7$, ($C_1$-$C_4$-alkyl)carbonyl, ($C_1$-$C_4$-haloalkyl)carbonyl, ($C_1$-$C_4$-alkyl)carbonyloxy, ($C_1$-$C_4$-alkyl)carbonylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, $NR^6R^7$, $NR^6COR^7$, $SF_5$, $SO_2NR^6R^7$, $C_2$-$C_4$-alkoxyalkyl or 1-methoxycyclopropyl substituents at nitrogen: $C_1$-$C_6$-alkyl, $C_1$-$C_3$-haloalkyl, $C_3$-$C_6$-cycloalkyl, $C_3$-$C_6$-halocycloalkyl, $C_4$-$C_{10}$-alkylcycloalkyl, $C_2$-$C_6$-alkenyl, $C_2$-$C_6$-haloalkenyl, $C_2$-$C_6$-alkynyl, $C_2$-$C_6$-haloalkynyl or phenyl or $R^3$ is an unsubstituted or monosubstituted 5- to 15-membered heterocyclyl radical which is attached via a carbon atom and which may contain up to two further heteroatoms selected from the group consisting of nitrogen, oxygen and sulphur, where the substituent is selected from the list below:
substituents at carbon: cyano, halogen, $C_1$-$C_6$-alkyl, $C_1$-$C_3$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_2$-alkyl)silyl, phenyl, hydroxyl, $C_1$-$C_6$-alkoxy, $C_1$-$C_6$-haloalkoxy, $C_2$-$C_6$-alkenyloxy, $C_2$-$C_6$-alkynyloxy, $C_1$-$C_6$-alkylthio or $C_1$-$C_6$-haloalkylthio substituents at nitrogen: $C_1$-$C_6$-alkyl, $C_1$-$C_3$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_2$-alkyl)silyl or phenyl $R^6$, $R^7$ independently of one another represent hydrogen, $C_1$-$C_4$-alkyl, $C_1$-$C_3$-haloalkyl, $C_3$-$C_6$-cycloalkyl, $R^8$ are identical or different and independently of one another represent hydrogen, halogen, $C_1$-$C_4$-alkyl, $C_1$-$C_4$-alkoxy, $C_3$-$C_6$-cycloalkyl or $C_1$-$C_3$-haloalkyl, $R^9$ are identical or different and independently of one another represent hydrogen, $C_1$-$C_4$-alkyl, or $C_3$-$C_6$-cycloalkyl, and also agrochemically active salts thereof.

The invention also provides the use of the compounds of the formula (I) as fungicides.

DETAILED DESCRIPTION OF A PREFERRED EMBODIMENT

Heterocyclyl-substituted thiazoles of the formula (I) according to the invention and also their agrochemically active salts are highly suitable for controlling phytopathogenic harmful fungi. The compounds according to the invention mentioned above have in particular strong fungicidal activity and can be used both in crop protection, in the domestic and hygiene field and in the protection of materials.

The compounds of the formula (I) can be present both in pure form and as mixtures of various possible isomeric forms, in particular of stereoisomers, such as E and Z, threo and erythro, and also optical isomers, such as R and S isomers or atropisomers, and, if appropriate, also of tautomers. What is claimed are both the E and the Z isomers, and the threo and erythro, and also the optical isomers, mixtures of these isomers, and also the possible tautomeric forms.

Preference is given to compounds of the formula (I) in which one or more of the symbols have one of the meanings below:

A represents methyl
or
A represents phenyl which may contain up to two substituents, where the substituents independently of one another are selected from the list below:
cyano, nitro, halogen, $C_1$-$C_4$-alkyl, $C_1$-$C_3$-haloalkyl, $C_3$-$C_6$-cycloalkyl, $C_2$-$C_4$-alkenyl, $C_2$-$C_4$-alkynyl, hydroxyl, $C_1$-$C_4$-alkoxy, $C_1$-$C_4$-haloalkoxy, $C_1$-$C_4$-alkylthio, $C_1$-$C_4$-haloalkylthio, ($C_1$-$C_4$-alkoxy)carbonyl, ($C_1$-$C_4$-alkyl)carbonyl, ($C_1$-$C_4$-haloalkyl)carbonyl, $C_1$-$C_4$-alkylsulphinyl, $C_1$-$C_4$-haloalkylsulphinyl, $C_1$-$C_4$-alkylsulphonyl or $C_1$-$C_4$-haloalkylsulphonyl,
or
A represents a heteroaromatic radical selected from the group below: furan-2-yl, furan-3-yl, thiophen-2-yl, thiophen-3-yl, isoxazol-3-yl, isoxazol-4-yl, isoxazol-5-yl, 1H-pyrrol-1-yl, 1H-pyrrol-2-yl, 1H-pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1H-indol-1-yl, 1H-indol-2-yl, 1H-indol-3-yl, 1H-indol-4-yl, 1H-indol-5-yl, 1H-indol-6-yl, 1H-indol-7-yl, 1H-benzimidazol-1-yl, 1H-benzimidazol-2-yl, 1H-benzimidazol-4-yl, benzimidazol-5-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzoxazol-2-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl,
which may contain up to two substituents, where the substituents independently of one another are selected from the list below:
substituents at carbon: cyano, halogen, $C_1$-$C_4$-alkyl, $C_1$-$C_3$-haloalkyl, hydroxyl, $C_1$-$C_4$-alkoxy, $C_1$-$C_4$-haloalkoxy, $C_1$-$C_4$-alkylthio or $C_1$-$C_4$-haloalkylthio,
substituents at nitrogen: $C_1$-$C_4$-alkyl, $C_1$-$C_3$-haloalkyl, cyclopropyl, $C_2$-$C_4$-alkenyl or $C_2$-$C_4$-alkynyl,
$L^1$ represents $(C(R^1)_2)_n$
where n=0 to 3

$R^1$ are identical or different and independently of one another represent hydrogen, chlorine, fluorine, methyl, $CF_3$ or cyano,
with the provision that $L^1$ may contain at most two $R^1$ different from hydrogen,
Y represents sulphur or oxygen,
W represents an unsubstituted or monosubstituted $C_1$- to $C_2$-carbon chain, where the substituent is selected from the group consisting of cyano and $C_1$-$C_2$-alkyl,
X represents an unsubstituted or monosubstituted $C_1$- to $C_2$-carbon chain, where the substituent is selected from the group consisting of cyano and $C_1$-$C_2$-alkyl,
$R^2$ represents hydrogen, $C_1$-$C_2$-alkyl or halogen,
$L^2$ represents —C($R^8$)$_2$—C($R^8$)$_2$— or —CR$^9$=CR$^9$— or —C≡C—,
$L^3$ represents a direct bond,
or
$L^3$ represents a $C_1$- to $C_4$-carbon chain which may contain up to two substituents, where the substituents independently of one another are selected from the list below:
$C_1$-$C_2$-alkyl, $C_1$-$C_2$-alkoxy, $C_1$-$C_2$-haloalkyl or cyclopropyl,
$R^3$ represents methyl, $C_1$-$C_2$-haloalkyl, —CH=CH$_2$, —C≡CH, or unsubstituted or monosubstituted $C_3$-$C_{10}$-cycloalkyl, where the substituent is selected from the list below:
halogen, $C_1$-$C_6$-alkyl, $C_3$-$C_6$-cycloalkyl, $C_2$-$C_6$-alkenyl, $C_2$-$C_6$-alkynyl, tri($C_1$-$C_2$-alkyl)silyl, phenyl or oxo,
or
$R^3$ represents phenyl which may contain up to three substituents, where the substituents independently of one another are selected from the list below:
cyano, nitro, halogen, $C_1$-$C_6$-alkyl, $C_1$-$C_3$-haloalkyl, $C_3$-$C_6$-cycloalkyl, $C_3$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_2$-alkyl)silyl, phenyl, hydroxyl, $C_1$-$C_6$-alkoxy, $C_1$-$C_6$-haloalkoxy, $C_1$-$C_6$-alkylthio or $C_1$-$C_6$-haloalkylthio,
or
$R^3$ represents naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 1H-inden-2-yl, 1H-inden-3-yl, 1H-inden-4-yl, 1H-inden-5-yl, 1H-inden-6-yl, 1H-inden-7-yl, 2,3-dihydro-1H-inden-1-yl, 2,3-dihydro-1H-inden-2-yl, 2,3-dihydro-1H-inden-4-yl or 2,3-dihydro-1H-inden-5-yl,
which may contain up to two substituents, where the substituents independently of one another are selected from the list below:
cyano, halogen, $C_1$-$C_6$-alkyl, $C_1$-$C_3$-haloalkyl, $C_3$-$C_6$-cycloalkyl, phenyl, hydroxyl, $C_1$-$C_6$-alkoxy, $C_1$-$C_3$-haloalkoxy, $C_1$-$C_6$-alkylthio or $C_1$-$C_3$-haloalkylthio,
or
$R^3$ represents furan-2-yl, furan-3-yl, thiophen-2-yl, thiophen-3-yl, isoxazol-3-yl, isoxazol-4-yl, isoxazol-5-yl, 1H-pyrrol-1-yl, 1H-pyrrol-2-yl, 1H-pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, pyridin-2-yl, pyridin-3-yl, pyridin-4-yl, pyridazin-3-yl, pyridazin-4-yl, pyrimidin-2- yl, pyrimidin-4-yl, pyrimidin-5-yl, pyrazin-2-yl, 1,3,5-triazin-2-yl or 1,2,4-triazin-3-yl, which may contain up to two substituents, where the substituents independently of one another are selected from the list below:

substituents at carbon: cyano, halogen, $C_1$-$C_6$-alkyl, $C_1$-$C_3$-haloalkyl, $C_3$-$C_6$-cycloalkyl, phenyl, hydroxyl, $C_1$-$C_4$-alkoxy, $C_1$-$C_4$-haloalkoxy, $C_1$-$C_4$-alkylthio or $C_1$-$C_4$-haloalkylthio, substituents at nitrogen: $C_1$-$C_6$-alkyl, $C_1$-$C_3$-haloalkyl, $C_3$-$C_6$-cycloalkyl, $C_2$-$C_6$-alkenyl, $C_2$-$C_6$-alkynyl or phenyl, or $R^3$ represents 1H-indol-1-yl, 1H-indol-2-yl, 1H-indol-3-yl, 1H-indol-4-yl, 1H-indol-5-yl, 1H-indol-6-yl, 1H-indol-7-yl, 1H-benzimidazol-1-yl, 1H-benzimidazol-2-yl, 1H-benzimidazol-4-yl, benzimidazol-5-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl, which may contain up to two substituents, where the substituents independently of one another are selected from the list below:

substituents at carbon: cyano, halogen, $C_1$-$C_6$-alkyl, $C_1$-$C_3$-haloalkyl, $C_3$-$C_6$-cycloalkyl, phenyl, hydroxyl, $C_1$-$C_4$-alkoxy, $C_1$-$C_4$-haloalkoxy, $C_1$-$C_4$-alkylthio or $C_1$-$C_4$-haloalkylthio, substituents at nitrogen: $C_1$-$C_6$-alkyl, $C_1$-$C_3$-haloalkyl, $C_3$-$C_6$-cycloalkyl, $C_2$-$C_6$-alkenyl, $C_2$-$C_6$-alkynyl or phenyl, or $R^3$ represents an unsubstituted or monosubstituted 5- to 6-membered heterocyclyl radical which is attached via a carbon atom and which may contain up to two further heteroatoms selected from the group consisting of nitrogen, oxygen and sulphur, where the substituent is selected from the list below:

substituents at carbon: $C_1$-$C_6$-alkyl, $C_1$-$C_3$-haloalkyl, $C_3$-$C_6$-cycloalkyl, $C_2$-$C_6$-alkenyl, $C_2$-$C_6$-alkynyl, tri($C_1$-$C_2$-alkyl)silyl or phenyl, substituents at nitrogen: $C_1$-$C_6$-alkyl, $C_3$-$C_6$-cycloalkyl, $C_2$-$C_6$-alkenyl, $C_2$-$C_6$-alkynyl, tri($C_1$-$C_2$-alkyl)silyl or phenyl, $R^8$ are identical or different and independently of one another represent hydrogen, halogen, $C_1$-$C_2$-alkyl, $C_1$-$C_2$-alkoxy, cyclopropyl or $C_1$-$C_2$-haloalkyl, $R^9$ are identical or different and independently of one another represent hydrogen, $C_1$-$C_2$-alkyl, or cyclopropyl and also to the agrochemically active salts thereof.

Particular preference is given to compounds of the formula (I) in which one or more of the symbols have one of the meanings below:

A represents methyl, or

A represents phenyl which may contain up to two substituents, where the substituents independently of one another are selected from the list below:

cyano, nitro, halogen, $C_1$-$C_2$-alkyl, $C_1$-$C_2$-haloalkyl, hydroxyl, $C_1$-$C_2$-alkoxy or $C_1$-$C_2$-haloalkoxy, or A represents a heteroaromatic radical selected from the group below: furan-2-yl, furan-3-yl, thiophen-2-yl, thiophen-3-yl, oxazol-2-yl, oxazol-4-yl, oxazol-5-yl, thiazol-2-yl, thiazol-4-yl, thiazol-5-yl; pyrazol-1-yl, pyrazol-3-yl, pyrazol-4-yl, imidazol-1-yl, imidazol-2-yl, imidazol-4-yl, 1,2,4-triazol-1-yl, pyridin-2-yl, pyridin-3-yl, pyridin-4-yl, 1,2,4-triazin-3-yl, 1H-benzimidazol-2-yl or 1,3-benzothiazol-2-yl, which may contain up to two substituents, where the substituents independently of one another are selected from the list below:

substituents at carbon: cyano, halogen, $C_1$-$C_2$-alkyl, $C_1$-$C_2$-haloalkyl, hydroxyl, $C_1$-$C_2$-alkoxy or $C_1$-$C_2$-haloalkoxy, substituents at nitrogen: $C_1$-$C_2$-alkyl or $C_1$-$C_2$-haloalkyl, $L^1$ represents $(C(R^1)_2)_n$ where n=0 to 3, $R^1$ are identical or different and independently of one another represent hydrogen or methyl, with the provision that $L^1$ may contain at most two methyl substituents, Y represents sulphur or oxygen, W represents —$CH_2CH_2$—, X represents —$CH_2CH_2$—, $R^2$ represents hydrogen, methyl or halogen, $L^2$ represents —$C(R^8)_2$—$C(R^8)_2$— or —$CR^9$=$CR^9$— or —C≡C—, $L^3$ represents a direct bond, or $L^3$ represents a $C_1$- to $C_4$-carbon chain which may contain up to two substituents, where the substituents independently of one another are selected from the list below:

methyl, methoxy or $CF_3$, $R^3$ represents methyl, $C_1$-$C_2$-haloalkyl, —CH=$CH_2$, —C≡CH, or unsubstituted or monosubstituted $C_3$-$C_{10}$-cycloalkyl, where the substituent is selected from the list below:

fluorine, chlorine, methyl, ethyl, cyclopropyl, cyclopentyl or cyclohexyl, or $R^3$ represents phenyl which may contain up to three substituents, where the substituents independently of one another are selected from the list below:

cyano, halogen, $C_1$-$C_6$-alkyl, $C_1$-$C_3$-haloalkyl, phenyl, hydroxyl, $C_1$-$C_6$-alkoxy, $C_1$-$C_6$-haloalkoxy, $C_1$-$C_6$-alkylthio or $C_1$-$C_6$-haloalkylthio, or $R^3$ represents naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 1H-inden-2-yl, 1H-inden-3-yl, 1H-inden-4-yl, 1H-inden-5-yl, 1H-inden-6-yl, 1H-inden-7-yl, 2,3-dihydro-1H-inden-1-yl, 2,3-dihydro-1H-inden-2-yl, 2,3-dihydro-1H-inden-4-yl or 2,3-dihydro-1H-inden-5-yl, which may contain up to two substituents, where the substituents independently of one another are selected from the list below:

fluorine, chlorine, bromine, iodine, methyl, ethyl, $CF_3$, $CHF_2$, cyclopropyl, phenyl, hydroxyl, OMe, OEt, $OCF_3$, $OCHF_2$, $OC_2F_5$, SMe or $SCF_3$, or $R^3$ represents furan-2-yl, furan-3-yl, thiophen-2-yl, thiophen-3-yl, isoxazol-3-yl, isoxazol-4-yl, isoxazol-5-yl, 1H-pyrrol-1-yl, 1H-pyrrol-2-yl, 1H-pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl or 1,2,4-triazin-3-yl, which may contain up to two substituents, where the substituents independently of one another are selected from the list below:
  substituents at carbon: cyano, fluorine, chlorine, bromine, iodine, methyl, ethyl, 1-methylethyl, 1,1-dimethylethyl, $CF_3$, $CHF_2$, $C_2F_5$, $CCl_3$, cyclopropyl, phenyl, hydroxyl, OMe, OEt, OisoPr, $OCF_3$, $OCHF_2$, $OC_2F_5$, SMe or $SCF_3$,
  substituents at nitrogen: methyl, ethyl, 1-methylethyl, 1,1-dimethylethyl, cyclopropyl or phenyl, or $R^3$ represents 1H-indol-1-yl, 1H-indol-2-yl, 1H-indol-3-yl, 1H-indol-4-yl, 1H-indol-5-yl, 1H-indol-6-yl, 1H-indol-7-yl, 1H-benzimidazol-1-yl, 1H-benzimidazol-2-yl, 1H-benzimidazol-4-yl, benzimidazol-5-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl, which may contain up to two substituents, where the substituents independently of one another are selected from the list below:
  substituents at carbon: cyano, fluorine, chlorine, bromine, iodine, methyl, ethyl, 1-methylethyl, 1,1-dimethylethyl, $CF_3$, $CHF_2$, $C_2F_5$, $CCl_3$, cyclopropyl, phenyl, hydroxyl, OMe, OEt, OisoPr, $OCF_3$, $OCHF_2$, $OC_2F_5$, SMe or $SCF_3$,
  substituents at nitrogen: methyl, ethyl, 1-methylethyl, 1,1-dimethylethyl, cyclopropyl or phenyl, or $R^3$ represents unsubstituted or monosubstituted pyrrolidin-2-yl, pyrrolidin-3-yl, morpholin-3-yl, morpholin-2-yl, piperidin-2-yl, piperidin-3-yl or piperazin-2-yl, where the substituent is selected from the list below:
  substituents at carbon: methyl, ethyl, $CF_3$, cyclopropyl or phenyl,
  substituents at nitrogen: methyl, ethyl, cyclopropyl or phenyl, $R^8$ are identical or different and independently of one another represent hydrogen, methyl, ethyl or $CF_3$,
$R^9$ are identical or different and independently of one another represent hydrogen, methyl or ethyl,
and also to the agrochemically active salts thereof.

Very particular preference is given to compounds of the formula (I) in which one or more of the symbols have one of the meanings below:

A represents methyl, or

A represents phenyl which may contain up to two substituents, where the substituents independently of one another are selected from the list below:
  cyano, fluorine, chlorine, bromine, iodine, methyl, ethyl, $CF_3$, $CHF_2$, $C_2F_5$, $CCl_3$, hydroxyl, OMe, $OCF_3$, $OCHF_2$, $OCH_2CF_3$ or $OC_2F_5$, or A represents a heteroaromatic radical selected from the group below: thiophen-3-yl, pyrazol-1-yl, pyrazol-4-yl, pyridin-4-yl, 1H-benzimidazol-2-yl or 1,3-benzothiazol-2-yl, which may contain up to two substituents, where the substituents independently of one another are selected from the list below:
  substituents at carbon: cyano, fluorine, chlorine, bromine, iodine, methyl, ethyl, $CF_3$, $CHF_2$, $C_2F_5$, $CCl_3$, hydroxyl, OMe, $OCF_3$, $OCHF_2$, $OCH_2CF_3$ or $OC_2F_5$,
  substituents at nitrogen: methyl, ethyl or $CF_3$, $L^1$ represents $(C(R^1)_2)_n$
where n=0 to 3,
$R^1$ are identical or different and independently of one another represent hydrogen or methyl,
with the provision that $L^1$ may contain at most one methyl substituent,
Y represents sulphur or oxygen,
W represents —$CH_2CH_2$—,
X represents —$CH_2CH_2$—,
$R^2$ represents hydrogen, methyl, chlorine or bromine,
$L^2$ represents —$C(R^8)_2$—$C(R^8)_2$— or —$CR^9$=$CR^9$— or —C≡C—,
$L^3$ represents a direct bond, or $L^3$ represents a $C_1$- to $C_4$-carbon chain,
$R^3$ represents methyl, $CF_3$, —CH=$CH_2$, —C≡CH, cyclopropyl, cyclobutyl, cyclopentyl, cyclohexyl, cycloheptyl or cyclooctyl, or $R^3$ represents phenyl which may contain up to two substituents, where the substituents independently of one another are selected from the list below:
  cyano, fluorine, chlorine, bromine, iodine, methyl, ethyl, 1-methylethyl, 1,1-dimethylethyl, $CF_3$, $CHF_2$, $C_2F_5$, $CCl_3$, phenyl, hydroxyl, OMe, OEt, OisoPr, $OCF_3$, $OCHF_2$, $OC_2F_5$, SMe or $SCF_3$, or $R^3$ represents naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 1H-inden-2-yl, 1H-inden-3-yl, 1H-inden-4-yl, 1H-inden-5-yl, 1H-inden-6-yl, 1H-inden-7-yl, 2,3-dihydro-1H-inden-1-yl, 2,3-dihydro-1H-inden-2-yl, 2,3-dihydro-1H-inden-4-yl or 2,3-dihydro-1H-inden-5-yl, or $R^3$ represents furan-2-yl, furan-3-yl, thiophen-2-yl, thiophen-3-yl, isoxazol-3-yl, isoxazol-4-yl, isoxazol-5-yl, 1H-pyrrol-1-yl, 1H-pyrrol-2-yl, 1H-pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, pyridin-2-yl, pyridin-3-yl, pyridin-4-yl, pyridazin-3-yl, pyridazin-4-yl, pyrimidin-2- yl, pyrimidin-4-yl, pyrimidin-5-yl, pyrazin-2-yl, 1,3,5-triazin-2-yl or 1,2,4-triazin-3-yl, or $R^3$ represents 1H-indol-1-yl, 1H-indol-2-yl, 1H-indol-3-yl, 1H-indol-4-yl, 1H-indol-5-yl, 1H-indol-6-yl, 1H-indol-7-yl, 1H-benzimidazol-1-yl, 1H-benzimidazol-2-yl, 1H-benzimidazol-4-yl, benzimidazol-5-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl, or $R^3$ represents pyrrolidin-2-yl, pyrrolidin-3-yl, morpholin-3-yl, morpholin-2-yl, piperidin-2-yl, piperidin-3-yl or piperazin-2-yl, $R^8$ are identical or different and independently of one another represent hydrogen, methyl or ethyl, $R^9$ are identical or different and independently of one another represent hydrogen, methyl or ethyl, and also to the agrochemically active salts thereof.

Extraordinary preference is given to compounds of the formula (I) in which one or more of the symbols have one of the meanings below:

A represents methyl, 1,3-dihydro-2H-indazol-2-yl, 3-chlorophenyl, 2,5-dichlorophenyl, 3-(trifluoromethyl)phenyl, 3,4-dimethoxyphenyl, 2,5-dibromophenyl, 2-bromo-5-(trifluoromethyl)phenyl, 5-bromo-2-methylphenyl, 5-iodo-2-methylphenyl, 2,5-bis(trifluoromethyl)phenyl, 2-chloro-5-(trifluoromethyl)phenyl, 1H-pyrazol-1-yl, 3-(trifluoromethyl)-1H-pyrazol-1-yl, 3,5-dimethyl-1H-pyrazol-1-yl, 5-methyl-3-(trifluoromethyl)-1H-pyrazol-1-yl, 4-chloro-5-methyl-3-(trifluoromethyl)-1H-pyrazol-1-yl, 3,5-bis(trifluoromethyl)-1H-pyrazol-1-yl, 5-(difluoromethyl)-3-methyl-1H-pyrazol-1-yl, 3,5-dichloro-1H-pyrazol-1-yl, 3,5-dibromo-1H-pyrazol-1-yl, 5-chloro-1-methyl-1H-pyrazol-4-yl, thiophen-3-yl, pyridin-4-yl, 3-chloro-5-(trifluoromethyl)pyridin-2-yl, 1H-benzimidazol-2-yl or 1,3-benzothiazol-2-yl, $L^1$ is a direct bond, or $L^1$ represents —CH$_2$—, —CH$_2$CH$_2$—, —CH$_2$CH$_2$CH$_2$— or —CHCH$_3$—, Y represents sulphur or oxygen, W represents —CH$_2$CH$_2$—, X represents —CH$_2$CH$_2$—, $R^2$ represents hydrogen, methyl or bromine, $L^2$ represents —CH$_2$CH$_2$—, —CH$_2$CHCH$_3$—, —CH=CH— (Z), —CH=CH— (E) or —C≡C—, $L^3$ represents a direct bond, or $L^3$ represents —CH$_2$—, —CH$_2$C(CH$_3$)$_2$—, —CH$_2$CHCH$_3$—, $R^3$ represents methyl, —CH=CH$_2$, —C≡CH, CF$_3$, cyclohexyl, phenyl, 4-chlorophenyl, 4-methoxyphenyl, 3-(trifluoromethyl)phenyl, naphthalen-1-yl, naphthalen-2-yl or pyridin-3-yl, and also to the agrochemically active salts thereof.

Extraordinary preference is furthermore given to compounds of the formula (I) in which A represents unsubstituted or substituted pyrazol-1-yl or pyrazol-4-yl, which may contain up to two substituents, where the substituents independently of one another are selected from the list below:

substituents at carbon: cyano, fluorine, chlorine, bromine, iodine, methyl, ethyl, CF$_3$, CHF$_2$, C$_2$F$_5$, CCl$_3$, hydroxyl, OMe, OCF$_3$, OCHF$_2$, OCH$_2$CF$_3$, or OC$_2$F$_5$, substituents at nitrogen: methyl, ethyl or CF$_3$, and $L_1$ represents —CH$_2$—, where the other substituents have one or more of the meanings mentioned above, and to the agrochemically active salts thereof.

Extraordinary preference is furthermore given to compounds of the formula (I) in which A represents unsubstituted or substituted phenyl, where the substituents independently of one another are selected from the list below:

cyano, fluorine, chlorine, bromine, iodine, methyl, ethyl, CF$_3$, CHF$_2$, C$_2$F$_5$, CCl$_3$, hydroxyl, OMe, OCF$_3$, OCHF$_2$, OCH$_2$CF$_3$ or OC$_2$F$_5$, and $L^1$ represents —CH$_2$—, where the other substituents have one or more of the meanings mentioned above, and to the agrochemically active salts thereof.

Extraordinary preference is furthermore given to compounds of the formula (I) in which Y represents oxygen, where the other substituents have one or more of the meanings mentioned above, and to the agrochemically active salts thereof.

Extraordinary preference is furthermore given to compounds of the formula (I) in which one or more of the symbols have one of the meanings below:

W represents —CH$_2$CH$_2$—

X represents —CH$_2$CH$_2$— where the other substituents have one or more of the meanings mentioned above, and to the agrochemically active salts thereof.

Extraordinary preference is furthermore given to compounds of the formula (I) in which $R^2$ represents hydrogen, halogen or methyl, where the other substituents have one or more of the meanings mentioned above, and to the agrochemically active salts thereof.

Extraordinary preference is furthermore given to compounds of the formula (I) in which $L^2$ represents —CH$_2$CH$_2$—, where the other substituents have one or more of the meanings mentioned above, and to the agrochemically active salts thereof.

Extraordinary preference is furthermore given to compounds of the formula (I) in which $L^2$ represents —CH=CH— (Z), where the other substituents have one or more of the meanings mentioned above, and to the agrochemically active salts thereof.

Extraordinary preference is furthermore given to compounds of the formula (I) in which $L^2$ represents —CH=CH— (E), where the other substituents have one or more of the meanings mentioned above, and to the agrochemically active salts thereof.

Extraordinary preference is furthermore given to compounds of the formula (I) in which
$L^2$ represents —C≡C—,
where the other substituents have one or more of the meanings mentioned above,
and to the agrochemically active salts thereof.

Extraordinary preference is furthermore given to compounds of the formula (I) in which
$L^3$ represents a direct bond,
where the other substituents have one or more of the meanings mentioned above,
and to the agrochemically active salts thereof.

Extraordinary preference is furthermore given to compounds of the formula (I) in which
$L^3$ represents —CH$_2$—,
where the other substituents have one or more of the meanings mentioned above,
and to the agrochemically active salts thereof.

Extraordinary preference is furthermore given to compounds of the formula (I) in which
$R^3$ represents unsubstituted naphthalen-1-yl or naphthalen-2-yl,
where the other substituents have one or more of the meanings mentioned above,
and to the agrochemically active salts thereof.

Extraordinary preference is furthermore given to compounds of the formula (I) in which
$R^3$ represents unsubstituted phenyl,
where the other substituents have one or more of the meanings mentioned above,
and to the agrochemically active salts thereof.

Extraordinary preference is furthermore given to compounds of the formula (I) in which
A represents 2,5-dimethylphenyl, 2,3,6-trifluorophenyl, 3,5-bis(difluoromethyl)-1H-pyrazol-1-yl, 3-(propan-2-yl)-5-(trifluoromethyl)-1H-pyrazol-1-yl, 3-tert-butyl-5-(pentafluoroethyl)-1H-pyrazol-1-yl, 3-tert-butyl-5-(trifluoromethyl)-1H-pyrazol-1-yl, 5-ethyl-3-(trifluoromethyl)-1H-pyrazol-1-yl, 5-tert-butyl-3-(pentafluoroethyl)-1H-pyrazol-1-yl, 5-tert-butyl-3-(trifluoromethyl)-1H-pyrazol-1-yl, 2H-indazol-2-yl, 1,3-benzodioxol-5-yl or 1H-benzimidazol-2-yl,
where the other substituents have one or more of the meanings mentioned above,
and to the agrochemically active salts thereof.

Extraordinary preference is furthermore given to compounds of the formula (I) in which
$R^3$ represents 2,4-dichlorophenyl, 2,4-dimethoxyphenyl, 2,5-dimethoxyphenyl, 2-methoxyphenyl, 2-methylphenyl, 3,5-dimethylisoxazol-4-yl, 3-methylpyridin-2-yl, quinolin-8-yl, morpholin-4-yl, naphthalene, tert-butyl, trimethylsilyl, 1,2,3,4-tetrahydronaphthalen-1-yl, cyclohexyl, 2-bromophenyl, 2-chlorophenyl, 2-chloro-6-fluorophenyl, 2,6-difluorophenyl,
where the other substituents have one or more of the meanings mentioned above,
and to the agrochemically active salts thereof.

The radical definitions given above can be combined with one another as desired. Moreover, individual definitions may not apply.

Depending on the nature of the substituents defined above, the compounds of the formula (I) have acidic or basic properties and can form salts, if appropriate also inner salts, or adducts with inorganic or organic acids or with bases or with metal ions. If the compounds of the formula (I) carry amino, alkylamino or other groups which induce basic properties, these compounds can be reacted with acids to give salts, or they are directly obtained as salts in the synthesis. If the compounds of the formula (I) carry hydroxyl, carboxyl or other groups which induce acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, furthermore ammonia, primary, secondary and tertiary amines having ($C_1$-$C_4$)-alkyl groups, mono-, di- and trialkanolamines of ($C_1$-$C_4$)-alkanols, choline and also chlorocholine.

The salts obtainable in this manner also have fungicidal, herbicidal and insecticidal properties.

Examples of inorganic acids are hydrohalic acids, such as hydrogen fluoride, hydrogen chloride, hydrogen bromide and hydrogen iodide, sulphuric acid, phosphoric acid and nitric acid, and acidic salts, such as NaHSO$_4$ and KHSO$_4$. Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulphonic acids (sulphonic acids having straight-chain or branched alkyl radicals of 1 to 20 carbon atoms), arylsulphonic acids or aryldisulphonic acids (aromatic radicals, such as phenyl and naphthyl, which carry one or two sulphonic acid groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphonic acid radicals), where the alkyl and aryl radicals may carry further substituents, for example p-toluenesulphonic acid, salicylic acid, p-aminosalicylic acid, 2-phenoxybenzoic acid, 2-acetoxybenzoic acid, etc.

Suitable metal ions are in particular the ions of the elements of the second main group, in particular calcium and magnesium, of the third and fourth main group, in particular aluminium, tin and lead, and also of the first to eighth transition group, in particular chromium, manganese, iron, cobalt, nickel, copper, zinc and others. Particular preference is given to the metal ions of the elements of the fourth period. Here, the metals can be present in various valencies that they can assume.

Optionally substituted groups may be mono- or polysubstituted, where in the case of polysubstitution the substituents may be identical or different.

In the definitions of the symbols given in the formulae above, collective terms were used which are generally representative for the following substituents:
halogen: fluorine, chlorine, bromine and iodine;
alkyl: saturated, straight-chain or branched hydrocarbon radicals having 1 to 8 carbon atoms, for example (but not limited thereto) $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;
alkenyl: unsaturated, straight-chain or branched hydrocarbon radicals having 2 to 8 carbon atoms and a double bond in any position, for example (but not limited thereto) $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups having 2 to 8 carbon atoms and a triple bond in any position, for example (but not limited thereto) $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

alkoxy: saturated, straight-chain or branched alkoxy radicals having 1 to 8 carbon atoms, for example (but not limited thereto) $C_1$-$C_6$-alkoxy, such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

alkylthio: saturated, straight-chain or branched alkylthio radicals having 1 to 8 carbon atoms, for example (but not limited thereto) $C_1$-$C_6$-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

alkoxycarbonyl: an alkoxy group having 1 to 6 carbon atoms (as mentioned above) which is attached to the skeleton via a carbonyl group (—CO—);

alkylsulphinyl: saturated, straight-chain or branched alkylsulphinyl radicals having 1 to 8 carbon atoms, for example (but not limited thereto) $C_1$-$C_6$-alkylsulphinyl, such as methylsulphinyl, ethylsulphinyl, propylsulphinyl, 1-methylethylsulphinyl, butylsulphinyl, 1-methylpropylsulphinyl, 2-methylpropylsulphinyl, 1,1-dimethylethylsulphinyl, pentylsulphinyl, 1-methylbutylsulphinyl, 2-methylbutylsulphinyl, 3-methylbutylsulphinyl, 2,2-dimethylpropylsulphinyl, 1-ethylpropylsulphinyl, hexylsulphinyl, 1,1-dimethylpropylsulphinyl, 1,2-dimethylpropylsulphinyl, 1-methylpentylsulphinyl, 2-methylpentyl sulphinyl, 3-methylpentylsulphinyl, 4-methylpentylsulphinyl, 1,1-dimethylbutylsulphinyl, 1,2-dimethylbutylsulphinyl, 1,3-dimethylbutylsulphinyl, 2,2-dimethylbutylsulphinyl, 2,3-dimethylbutylsulphinyl, 3,3-dimethylbutylsulphinyl, 1-ethylbutylsulphinyl, 2-ethylbutylsulphinyl, 1,1,2-trimethylpropylsulphinyl, 1,2,2-trimethylpropylsulphinyl, 1-ethyl-1-methylpropylsulphinyl and 1-ethyl-2-methylpropylsulphinyl;

alkylsulphonyl: saturated, straight-chain or branched alkylsulphonyl radicals having 1 to 8 carbon atoms, for example (but not limited thereto) $C_1$-$C_6$-alkylsulphonyl, such as methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethylsulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexylsulphonyl, 1,1-dimethylpropylsulphonyl, 1,2-dimethylpropylsulphonyl, 1-methylpentylsulphonyl, 2-methylpentylsulphonyl, 3-methylpentylsulphonyl, 4-methylpentylsulphonyl, 1,1-dimethylbutylsulphonyl, 1,2-dimethylbutylsulphonyl, 1,3-dimethylbutylsulphonyl, 2,2-dimethylbutylsulphonyl, 2,3-dimethylbutylsulphonyl, 3,3-dimethylbutylsulphonyl, 1-ethylbutylsulphonyl, 2-ethylbutylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl;

cycloalkyl: monocyclic, saturated hydrocarbon groups having 3 to 10 carbon ring members, for example (but not limited thereto) cyclopropyl, cyclopentyl and cyclohexyl;

haloalkyl: straight-chain or branched alkyl groups having 1 to 8 carbon atoms (as mentioned above), where in these groups some or all of the hydrogen atoms may be replaced by halogen atoms as mentioned above, for example (but not limited thereto) $C_1$-$C_3$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl;

haloalkoxy: straight-chain or branched alkoxy groups having 1 to 8 carbon atoms (as mentioned above), where in these groups some or all of the hydrogen atoms may be replaced by halogen atoms as mentioned above, for example (but not limited thereto) $C_1$-$C_3$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy;

haloalkylthio: straight-chain or branched alkylthio groups having 1 to 8 carbon atoms (as mentioned above), where in these groups some or all of the hydrogen atoms may be replaced by halogen atoms as mentioned above, for example (but not limited thereto) $C_1$-$C_3$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio;

heteroaryl: a 5 or 6-membered completely unsaturated monocyclic ring system which contains one to four heteroatoms from the group consisting of oxygen, nitrogen and sulphur; if the ring contains a plurality of oxygen atoms, these are not directly adjacent;

5-membered heteroaryl which contains one to four nitrogen atoms or one to three nitrogen atoms and one sulphur or oxygen atom: 5-membered heteroaryl groups which, in addition to carbon atoms, may contain one to four nitrogen atoms or one to three nitrogen atoms and one sulphur or oxygen atom as ring members, for example (but not limited thereto) 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

5-membered heteroaryl which is attached via nitrogen and contains one to four nitrogen atoms, or benzo-fused 5-membered heteroaryl which is attached via nitrogen and contains one to three nitrogen atoms: 5-membered heteroaryl groups which, in addition to carbon atoms, may contain one to four nitrogen atoms and one to three nitrogen atoms, respectively, as ring members and in which two adjacent carbon ring members or a nitrogen and an adjacent carbon ring member may be bridged by a buta-1,3-dien-1,4-diyl group in which one or two carbon atoms may be replaced by nitrogen atoms, where these rings are attached to the skeleton via one of the nitrogen ring members, for example (but not limited thereto) 1-pyrrolyl, 1-pyrazolyl, 1,2,4-triazol-1-yl, 1-imidazolyl, 1,2,3-triazol-1-yl, 1,3,4-triazol-1-yl;

6-membered heteroaryl which contains one to four nitrogen atoms: 6-membered heteroaryl groups which, in addition to carbon atoms, may contain one to three or one to four nitrogen atoms as ring members, for example (but not limited thereto) 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 5-membered heteroaryl which contains one to three nitrogen atoms or one nitrogen atom and one oxygen or sulphur atom: for example (but not limited thereto) 1H-indol-1-yl, 1H-indol-2-yl, 1H-indol-3-yl, 1H-indol-4-yl, 1H-indol-5-yl, 1H-indol-6-yl, 1H-indol-7-yl, 1H-benzimidazol-1-yl, 1H-benzimidazol-2-yl, 1H-benzimidazol-4-yl, benzimidazol-5-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl and 1,3-benzoxazol-2-yl, benzo-fused 6-membered heteroaryl which contains one to three nitrogen atoms: for example (but not limited thereto) quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, and isoquinolin-8-yl;

heterocyclyl: a three- to fifteen-membered saturated or partially unsaturated heterocycle which contains one to four heteroatoms from the group consisting of oxygen, nitrogen and sulphur: mono-, bi- or tricyclic heterocycles which contain, in addition to carbon ring members, one to three nitrogen atoms and/or one oxygen or sulphur atom or one or two oxygen and/or sulphur atoms; if the ring contains a plurality of oxygen atoms, these are not directly adjacent; such as, for example (but not limited thereto), oxiranyl, aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydroopyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

leaving group: $S_N1$ or $S_N2$ leaving group, for example halogen (chlorine, bromine, iodine), alkylsulphonates (—$OSO_2$-alkyl, for example —$OSO_2CH_3$, —$OSO_2CF_3$) or arylsulphonates (—$OSO_2$-aryl, for example —$OSO_2Ph$, —$OSO_2PhMe$).

Not included are combinations which contradict natural laws and which the person skilled in the art would therefore have excluded based on his expert knowledge. Excluded are, for example, ring structures having three or more adjacent oxygen atoms.

The present invention furthermore relates to a process for preparing the heterocyclyl-substituted thiazoles of the formula (I) according to the invention, comprising at least one of steps (a) to (u) below:

(a) the conversion of compounds of the formula (VII) in the presence of an organometallic compound $R^9$-M and, if appropriate, in the presence of a solvent, into compounds of the formula (VIII), according to the reaction scheme below (Scheme 1):

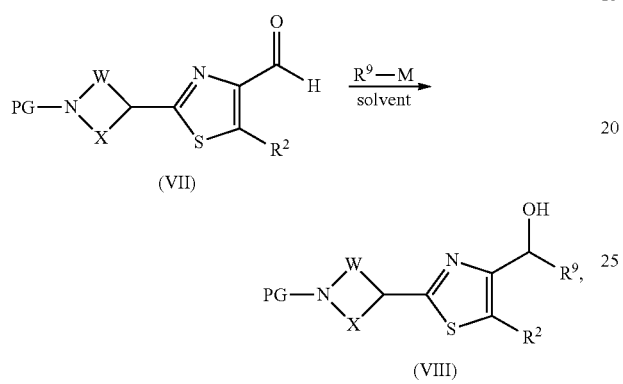

where

PG=unsubstituted or substituted phenylmethyl (where the substituents independently of one another are selected from the group consisting of methyl, methoxy, nitro, dioxolano), acetyl, $C_1$-$C_4$-alkoxycarbonyl and benzyloxycarbonyl, M=for example MgCl, MgBr, MgI, Li, $R^9$=$C_1$-$C_4$-alkyl or $C_3$-$C_6$-cycloalkyl, W, X, and $R^2$ are as defined for formula (I) above.

(b) the reaction of alcohols of the formula (VIII) with an oxidizing agent in the presence of a solvent, to give ketones of the formula (IX), according to the reaction scheme below (Scheme 2):

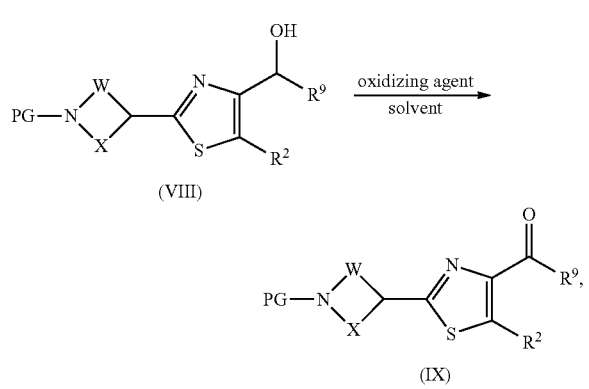

where

PG=unsubstituted or substituted phenylmethyl (where the substituents independently of one another are selected from the group consisting of methyl, methoxy, nitro, dioxolano), acetyl and $C_1$-$C_4$-alkoxycarbonyl, $R^9$=$C_1$-$C_4$-alkyl or $C_3$-$C_6$-cycloalkyl, W, X, and $R^2$ are as defined for formula (I) above.

(c) the conversion of ketones of the formula (IX) in the presence of a base or an acid and, if appropriate, a solvent, into compounds of the formula (IVb), according to the reaction scheme below (Scheme 3):

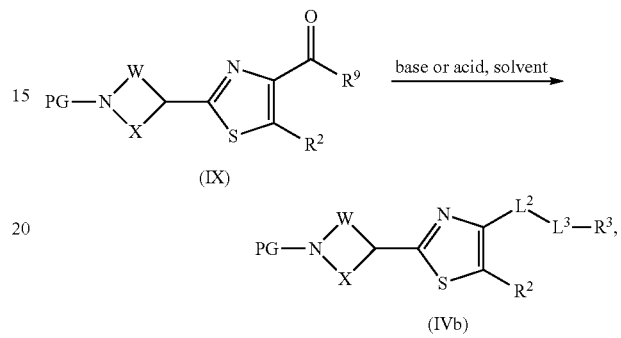

where

PG=unsubstituted or substituted phenylmethyl (where the substituents independently of one another are selected from the group consisting of methyl, methoxy, nitro, dioxolano), acetyl and $C_1$-$C_4$-alkoxycarbonyl, $L^2$=—$CR^9$=$CR^9$—, W, X, $L^3$, $R^2$, $R^3$ and $R^9$ are as defined for formula (I) above.

(d) the conversion of aldehydes of the formula (VII) in the presence of a base or an acid and, if appropriate, a solvent, into compounds of the formula (IVb), according to the reaction scheme below (Scheme 4):

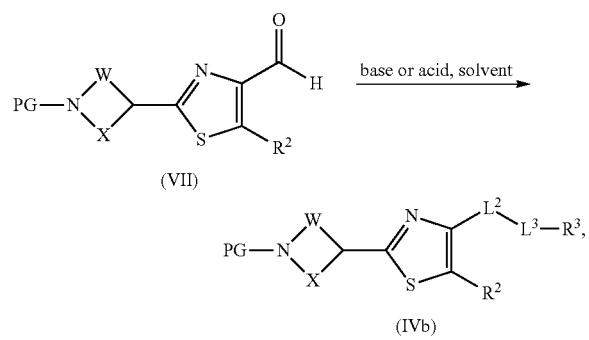

where

PG=unsubstituted or substituted phenylmethyl (where the substituents independently of one another are selected from the group consisting of methyl, methoxy, nitro, dioxolano), acetyl and $C_1$-$C_4$-alkoxycarbonyl, $L^2$=—$CR^9$=$CR^9$—, W, X, $L^3$, $R^2$, $R^3$ and $R^9$ are as defined for formula (I) above.

(e) the conversion of aldehydes of the formula (VII) in the presence of a base and, if appropriate, a solvent, into alkynes of the formula (X) according to the reaction scheme below (Scheme 5):

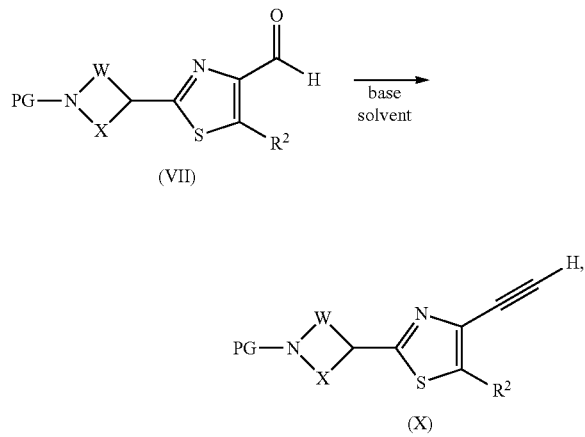

where
- PG=unsubstituted or substituted phenylmethyl (where the substituents independently of one another are selected from the group consisting of methyl, methoxy, nitro, dioxolano), acetyl and $C_1$-$C_4$-alkoxycarbonyl,
- W, X and $R^2$ are as defined for formula (I) above.

(f) the reaction of alkynes of the formula (X) with an $R^3$-$L^3$-halide in an optionally catalyzed C—C coupling reaction in the presence of a base and, if appropriate, a solvent, to give compounds of the formula (IVc), according to the reaction scheme below (Scheme 6):

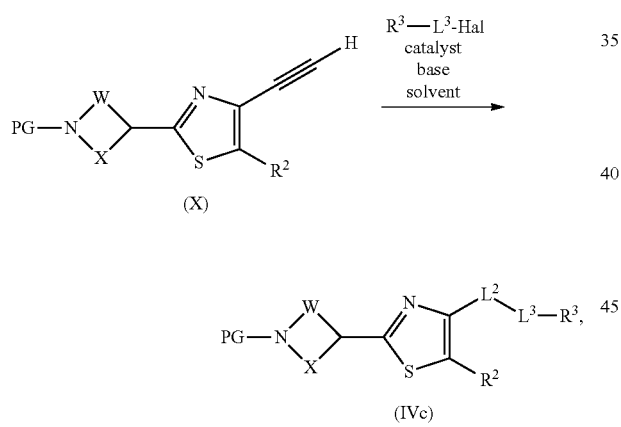

where
- PG=unsubstituted or substituted phenylmethyl (where the substituents independently of one another are selected from the group consisting of methyl, methoxy, nitro, dioxolano), acetyl and $C_1$-$C_4$-alkoxycarbonyl,
- Hal=Cl, Br or I,
- $L^2$=—C≡C—,
- W, X, $L^3$, $R^2$ and $R^3$ are as defined for formula (I) above.

(g) the reaction of alkynes of the formula (X) with a trialkylsilyl chloride $(R^{10}R^{11}R^{12})$SiCl or trialkylsilyl triflate $(R^{10}R^{11}R^{12})$SiOSO$_2$CF$_3$ or other known silylating agents in the presence of a base and, if appropriate, a solvent, to give compounds of the formula (XI), according to the reaction scheme below (Scheme 7):

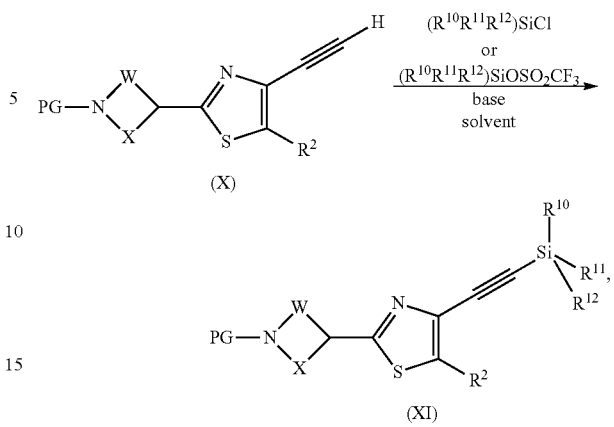

where
- PG=unsubstituted or substituted phenylmethyl (where the substituents independently of one another are selected from the group consisting of methyl, methoxy, nitro, dioxolano), acetyl and $C_1$-$C_4$-alkoxycarbonyl,
- $R^{10}$, $R^{11}$ and $R^{12}$=$C_1$-$C_4$ alkyl or phenyl,
- W, X and $R^2$ are as defined for formula (I) above.

(h) the reaction of alkynes of the formula (XI) with a compound $R^3$-$L^3$-Hal, if appropriate in the presence of a catalyst, in the presence of a base and, if appropriate, a solvent, to give compounds of the formula (IVc), according to the reaction scheme below (Scheme 8):

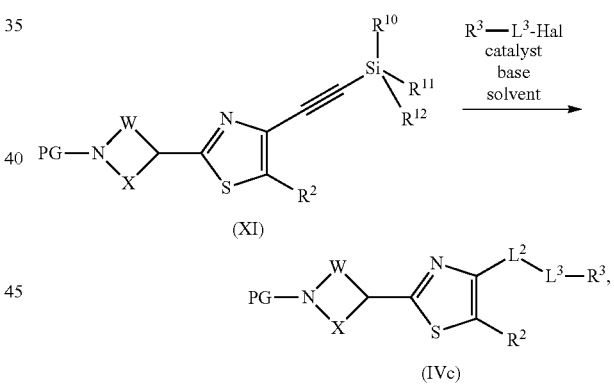

where
- PG=unsubstituted or substituted phenylmethyl (where the substituents independently of one another are selected from the group consisting of methyl, methoxy, nitro, dioxolano), acetyl and $C_1$-$C_4$-alkoxycarbonyl,
- Hal=Cl, Br or I,
- $R^2$=hydrogen, $C_1$-$C_2$-alkyl or $C_1$-$C_2$-haloalkyl,
- $L^2$=—C≡C—,
- $R^{10}$, $R^{11}$ and $R^{12}$=$C_1$-$C_4$-alkyl or phenyl,
- W, X, $L^3$ and $R^3$ are as defined for formula (I) above.

(i) the reaction of thioamides of the formula (V) with compounds of the formula (VIa) or (VIb) in the presence of a base and, if appropriate, in the presence of a solvent, to give compounds of the formula (IVa) or (IVb), according to the reaction scheme below (Scheme 9):

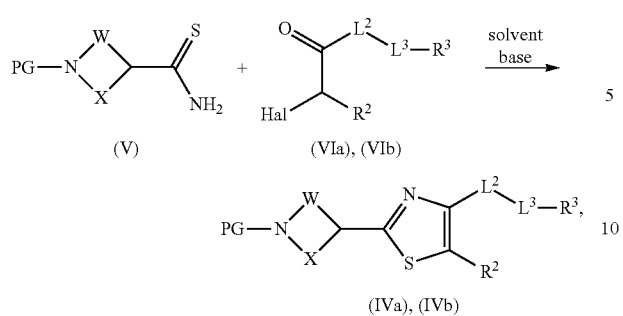

(V) + (VIa), (VIb) → (IVa), (IVb)

where
PG=unsubstituted or substituted phenylmethyl (where the substituents independently of one another are selected from the group consisting of methyl, methoxy, nitro, dioxolano), acetyl, $C_1$-$C_4$-alkoxycarbonyl and benzyloxycarbonyl,
Hal=Cl, Br or I,
$L^2$=—C($R^8$)$_2$—C($R^8$)$_2$— for compounds of the formula (IVa) and (VIa),
$L^2$=—$CR^9$=$CR^9$— for compounds of the formula (IVb) and (VIb),
W, X, $L^3$, $R^2$, $R^3$, $R^8$ and $R^9$ are as defined for formula (I) above.

(j) the conversion of compounds of the formula (IVb) or (IVc) in the presence of hydrogen, a catalyst and, if appropriate, a solvent, into compounds of the formula (IVa), according to the reaction scheme below, (Scheme 10):

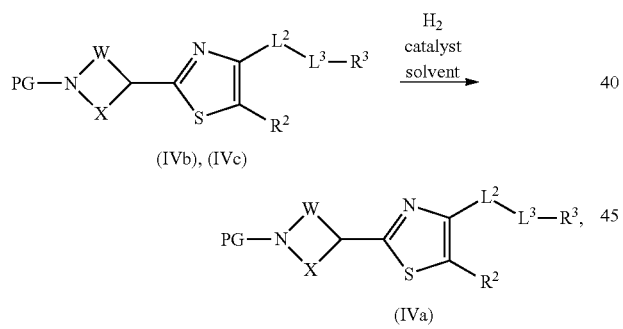

where
PG=acetyl or $C_1$-$C_4$-alkoxycarbonyl,
$L^2$=—C($R^8$)$_2$—C($R^8$)$_2$— for compounds of the formula (IVa),
$L^2$=—$CR^9$=$CR^9$— for compounds of the formula (IVb),
$L^2$=—C≡C— for compounds of the formula (IVc),
W, X, $L^3$, $R^2$, $R^3$, $R^8$ and $R^9$ are as defined for formula (I) above.

(k) the conversion of compounds of the formula (IV), if appropriate in the presence of a solvent and, if appropriate, in the presence of an acid or, if appropriate, in the presence of a base or, if appropriate, in the presence of a source of hydrogen, into compounds of the formula (II), according to the reaction scheme below (Scheme 11):

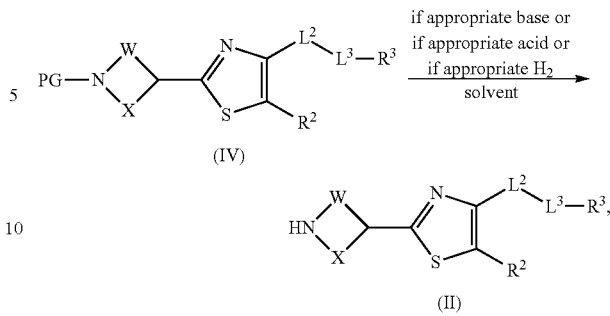

where
PG=acetyl, $C_1$-$C_4$-alkoxycarbonyl or benzyloxycarbonyl,
W, X, $L^2$, $L^3$, $R^2$, and $R^3$ are as defined for formula (I) above.

(l) the conversion of compounds of the formula (IIa') in the presence of a halogenating agent, if appropriate in the presence of an acid and a solvent, into compounds of the formula (IIa), according to the reaction scheme below (Scheme 12):

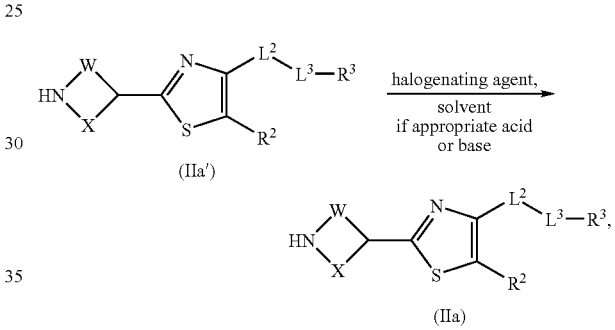

where
$L^2$=—C($R^8$)$_2$—C($R^8$)$_2$—,
$R^2$=I, Br or Cl for compounds of the formula (IIa),
$R^2$=hydrogen for compounds of the formula (IIa'),
W, X, $L^3$, $R^3$ and $R^8$ are as defined for formula (I) above.

(m) the reaction of compounds of the formula (III) with compounds of the formula (II), if appropriate in the presence of a coupling agent, a base and a solvent, to give compounds of the formula (I), according to the reaction scheme below (Scheme 13):

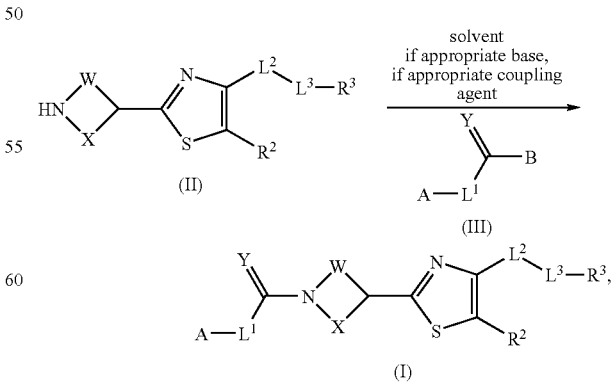

where
B=OH, chlorine, bromine or iodine,

Y=oxygen,

A, W, X, $L^1$, $L^2$, $L^3$, $R^2$, and $R^3$ are as defined for formula (I) above.

(n) the conversion of compounds of the formula (I) in the presence of a sulphurizing agent and, if appropriate, in the presence of a solvent, into compounds of the formula (I), according to the reaction scheme below (Scheme 14):

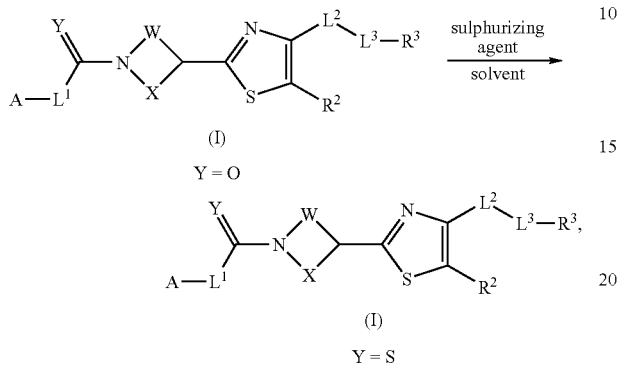

where

A, W, X, $L^1$, $L^2$, $L^3$, $R^2$, and $R^3$ are as defined for formula (I) above.

(o) the conversion of aldehydes of the formula (XII) in the presence of a base and, if appropriate, a solvent, into alkynes of the formula (XIII), according to the reaction scheme below (Scheme 17):

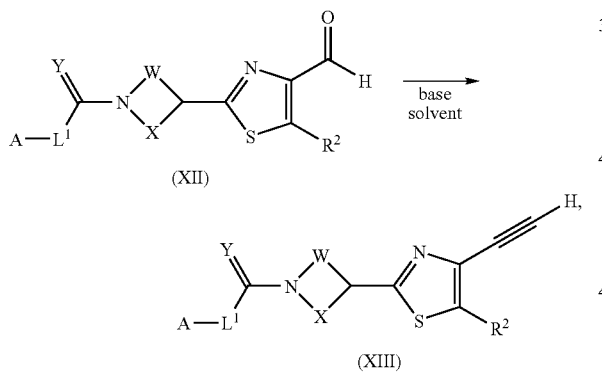

where

A, W, X, Y, $L^1$ and $R^2$ are as defined for formula (I) above.

(p) the reaction of alkynes of the formula (XIII) with a trialkylsilyl chloride $(R^{10}R^{11}R^{12})SiCl$ or trialkylsilyl triflate $(R^{10}R^{11}R^{12})SiOSO_2CF_3$ or other known silylating agents in the presence of a base and, if appropriate, a solvent, to give compounds of the formula (XIV), according to the reaction scheme below (Scheme 18):

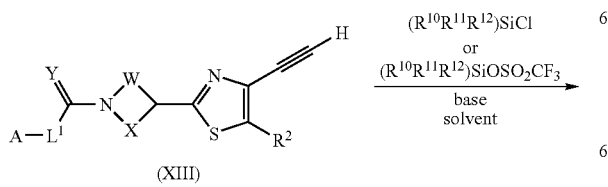

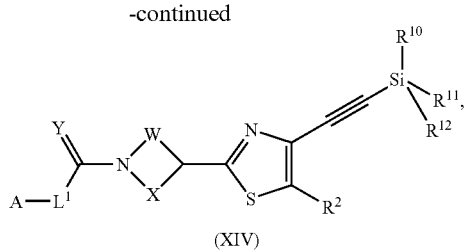

where $R^{10}$, $R^{11}$ and $R^{12}$=$C_1$-$C_4$ alkyl or phenyl,

A, W, X, Y, $L^1$ and $R^2$ are as defined for formula (I) above.

(q) the reaction of alkynes of the formula (XIII) with an $R^3$-$L^3$-halide in an optionally catalyzed C—C coupling reaction in the presence of a base and, if appropriate, a solvent, to give compounds of the formula (Ic), according to the reaction scheme below (Scheme 19):

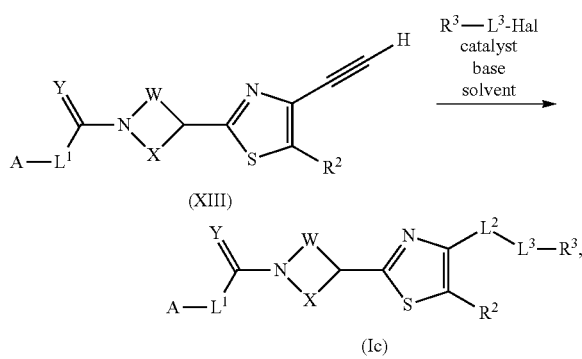

where

Hal=Cl, Br or I, $L^2$=—C≡C—,

A, W, X, Y, $L^1$ $L^3$, $R^2$ and $R^3$ are as defined for formula (I) above.

(r) the reaction of alkynes of the formula (XIV) with a compound $R^3$-$L^3$-Hal, if appropriate in the presence of a catalyst, in the presence of a base and, if appropriate, a solvent, to give compounds of the formula (Ic), according to the reaction scheme below (Scheme 20):

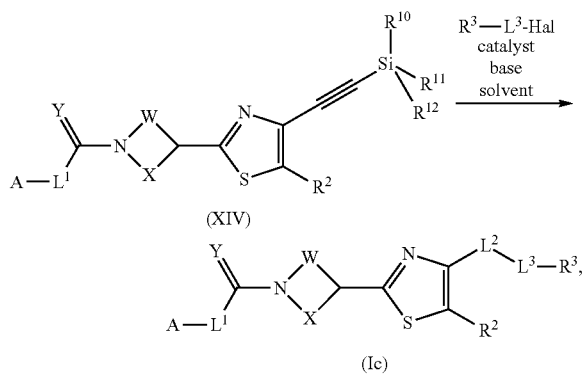

where
Hal=Cl, Br or I,
$L^2$=—C≡C—,
$R^{10}$, $R^{11}$ and $R^{12}$=$C_1$-$C_4$ alkyl or phenyl,
A, W, X, Y, $L^1$ $L^3$, $R^2$ and $R^3$ are as defined for formula (I) above.

(s) the conversion of aldehydes of the formula (XII) in the presence of a base or an acid and, if appropriate, a solvent, into compounds of the formula (Ib), according to the reaction scheme below (Scheme 21):

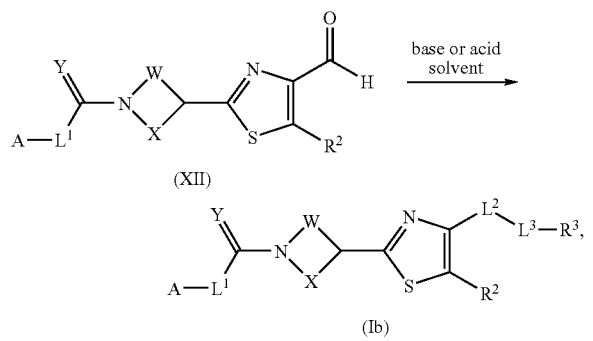

where
$L^2$=—$CR^9$=$CR^9$—,
A, W, X, Y, $L^1$ $L^3$, $R^2$, $R^3$ and $R^9$ are as defined for formula (I) above.

(t) the conversion of compounds of the formula (Ic) in the presence of hydrogen, a catalyst and, if appropriate, a solvent, into compounds of the formula (Ib), according to the reaction scheme below (Scheme 22):

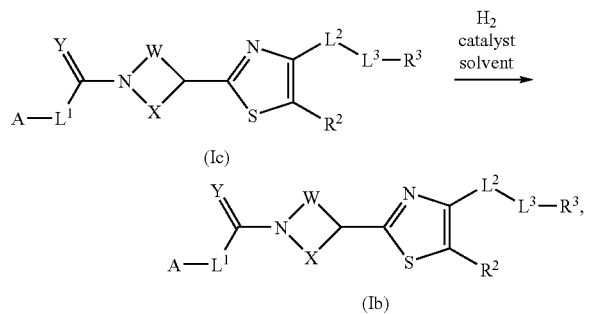

where
$L^2$=—$CR^9$=$CR^9$— for compounds of the formula (Ib),
$L^2$=—C≡C— for compounds of the formula (Ic),
A, W, X, Y, $L^1$ $L^3$, $R^2$, $R^3$ and $R^9$ are as defined for formula (I) above.

(u) the conversion of compounds of the formula (Ib) or (Ic) in the presence of hydrogen, a catalyst and, if appropriate, a solvent, into compounds of the formula (Ia), according to the reaction scheme below (Scheme 23):

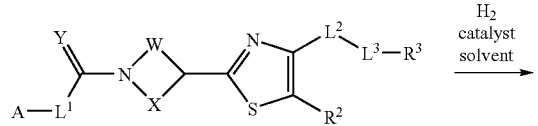

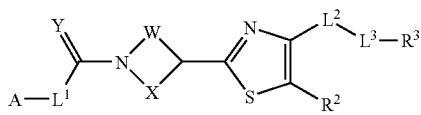

(Ic) → (Ia)
(Ib) → (Ia), where
$L^2$=—$C(R^8)_2$—$C(R^8)_2$— for compounds of the formula (Ia),
$L^2$=—$CR^9$=$CR^9$— for compounds of the formula (Ib),
$L^2$=—C≡C— for compounds of the formula (Ic),
A, W, X, Y, $L^1$ $L^3$, $R^2$, $R^3$, $R^8$ and $R^9$ are as defined for formula (I) above.

A general summary of the synthesis paths is shown in Schemes 15 and 24.

A compound of the general formula (V) is reacted with a compound of the formula (VIa) or (VIb) to give a cyclic compound of the formula (IVa) or (IVb) (Scheme 9). Another option of preparing compounds of the formula (IV) is to start with compounds of the formula (VII). These can be subjected to a reaction with a substrate of the general formula $R^9$-M (Scheme 1). A secondary alcohol of the formula (VIII) is formed, which is then oxidized, giving a compound of the formula (IX) (Scheme 2). A compound of the formula (VII) or (IX) is subjected to an olefination to prepare a compound of the formula (IVb) (Scheme 3 and Scheme 4). Another possible route of preparing compounds of the formula (IV) also starts with a compound of the formula (VII). A compound of the formula (VII) is alkynylated to prepare a terminal alkyne of the general formula (X) (Scheme 5). A transition metal-catalyzed C—C coupling reaction of a compound of the formula (X) with a halide of the formula $R^3$-$L^3$-Hal gives a compound of the formula (IVc) (Scheme 6). A compound of the formula (X) can also be provided with a silyl group, which leads to a compound of the formula (XI) (Scheme 7). This is then subjected to a transition metal-catalyzed coupling reaction, namely with a substrate of the general formula $R^3$-$L^3$-Hal, to prepare a compound of the formula (IVc) (Scheme 8). Using hydrogen, the double and triple bonds of a compound of the formula (IVb) and (IVc) can be hydrogenated, to give a compound of the formula (IVa) (Scheme 10). The protective group of a compound of the formula (IV), which is labelled PG, is then removed, forming a compound of the formula (II) or the corresponding salt (Scheme 11). A compound of the formula (IIa') can be halogenated to form a compound of the formula (IIa) (Scheme 12). A compound of the formula (II) or a corresponding salt is coupled with a substrate of the formula (III), which allows the preparation of a compound of the formula (I) (Scheme 13). A compound of the formula (I) is treated with a sulphurizing agent to generate a compound of the formula (I) (Scheme 14).

Scheme 15

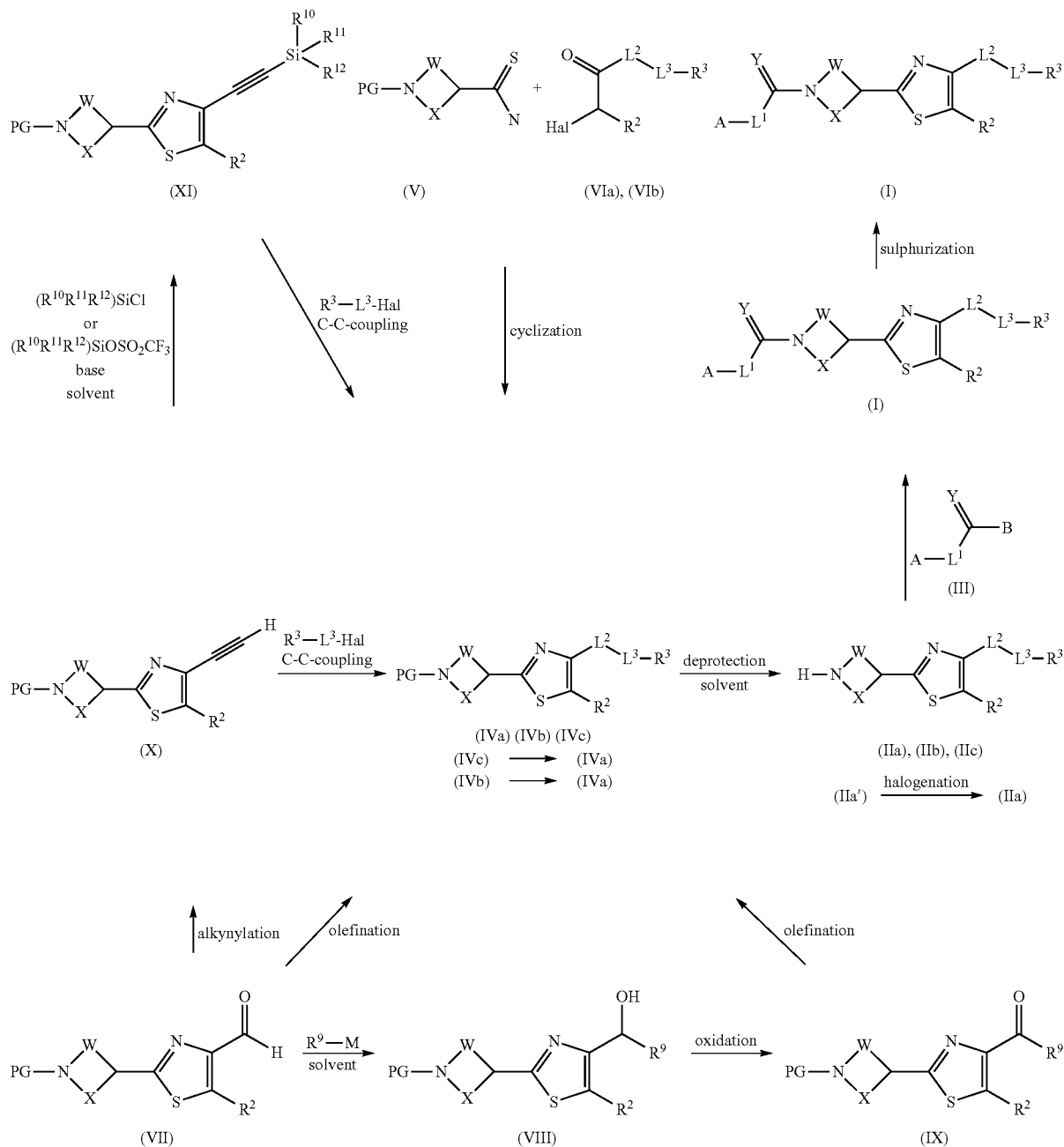

Another possible route of preparing compounds of the formula (I) starts with a compound of the formula (XII) (Scheme 24). A compound of the formula (XII) is alkynylated to prepare a terminal alkyne of the general formula (XIII) (Scheme 17). A transition metal-catalyzed C—C coupling reaction of a compound of the formula (XIII) with a halide of the formula $R^3$-$L^3$-Hal gives a compound of the formula (Ic) (Scheme 19). A compound of the formula (XIII) can also be provided with a silyl group, which leads to a compound of the formula (XIV) (Scheme 18). This is then subjected to a transition metal-catalyzed coupling reaction, namely with a substrate of the general formula $R^3$-$L^3$-Hal, to prepare a compound of the formula (Ic) (Scheme 20). A compound of the formula (XII) is subjected to an olefination to prepare a compound of the formula (Ib) (Scheme 21). Using hydrogen, the triple bond of a compound of the formula (Ic) can be hydrogenated, to give a compound of the formula (Ib) (Scheme 22). Using hydrogen, the double and triple bonds of a compound of the formula (Ib) and (Ic) can be hydrogenated, to give a compound of the formula (Ia) (Scheme 23).

Scheme 24

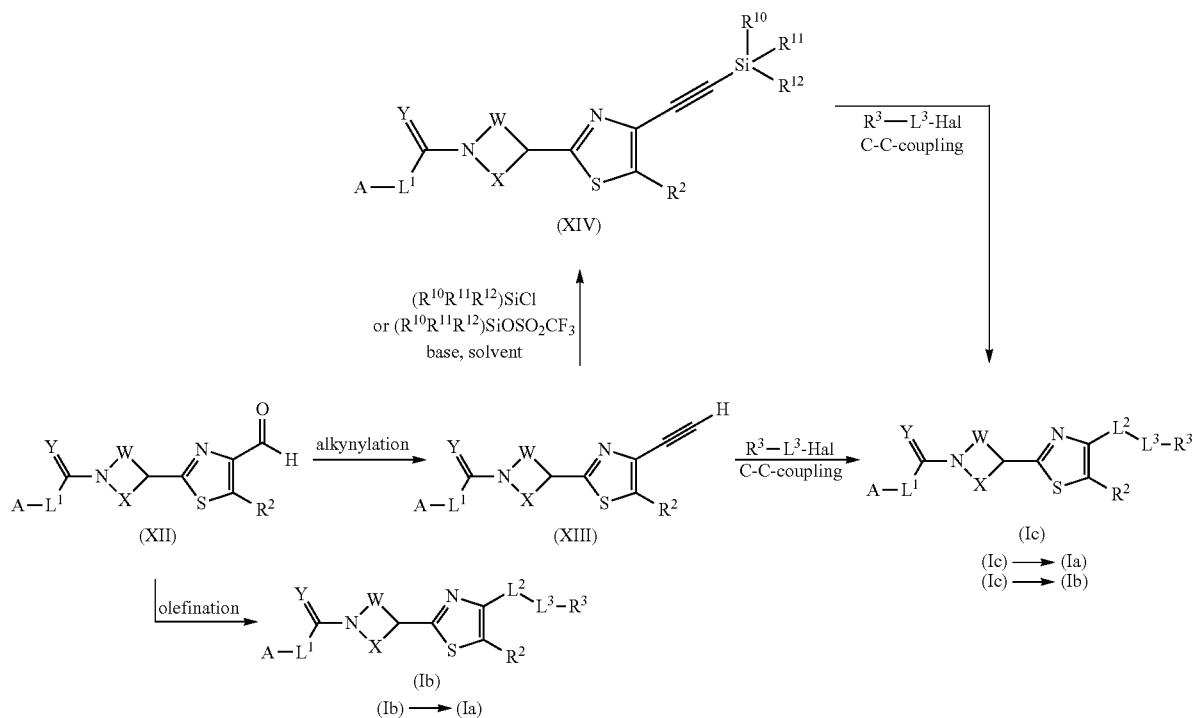

One way of preparing the intermediate (VIII) from compound (VII) is shown in Scheme 1.

Starting materials of the formula (VIII) are prepared from the aldehyde (VII) by addition of an organometallic reagent $R^9$-M (for example M=Mg, Li). The alcohols (VIII) are preferably prepared by addition of a Grignard reagent $R^9$—MgX (X=Cl, Br, or I) to compounds (VII) in tetrahydrofuran at −78° C., under an inert atmosphere (see, for example, WO 07/039,177).

The aldehyde (VII) is commercially available (for example Maybridge) or can be prepared from commercially available precursors according to procedures described in the literature. The aldehyde (VII) is prepared, for example, from the corresponding methyl or ethyl ester (XV) by reduction with lithium aluminium hydride in tetrahydrofuran at 0° C., followed by an oxidation of the corresponding alcohol with Dess-Martin reagent at room temperature in dichloromethane (see, for example, WO 07/147,336 and WO 07/039,177 for the reduction with lithium aluminium hydride and *J. Am. Chem. Soc.* 1978, 100, 300-301; 1979, 101, 5294-5299; 1991, 113, 7277-7287 for the oxidation using Dess-Martin reagent).

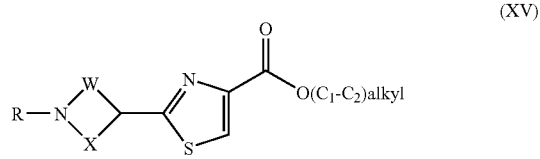

(XV)

where

R=H or acid-labile amine protective groups, such as, for example, t-butoxycarbonyl (tBoc) or benzyloxycarbonyl (Cbz) or a benzyl protective group, such as, for example, benzyl (Bn).

W and X are as defined for formula (I) above.

Methyl or ethyl esters (XV) are known and can be prepared from commercially available precursors according to methods described in the literature, for example from nitriles of the formula (XVI), carboxylic acids of the formula (XVII), carbonyl chlorides of the formula (XVIII), amides of the formula (XIX) or thioamides of the formula (V) (FIG. 2). A preferred method is the Hantzsch thiazole synthesis. Starting from (V) and commercially available ethyl or methyl halpyruvate in ethanol or in N,N-dimethylformamide in the presence of, for example, triethylamine at room temperature (for examples see WO 07/014290 and the references cited therein).

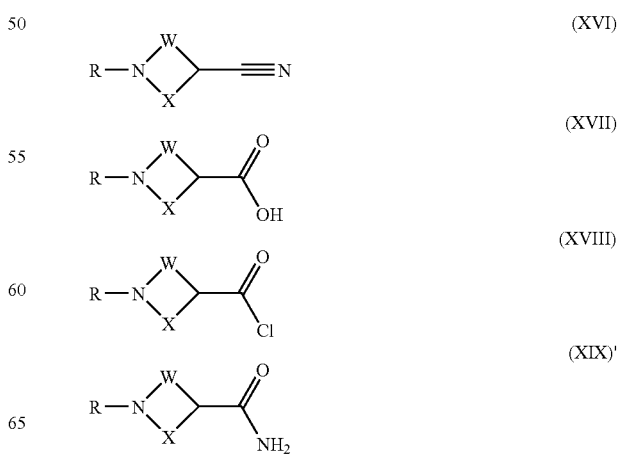

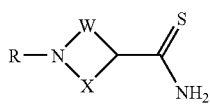

(V)

where
R=H or acid-labile amine protective groups, such as, for example, t-butoxycarbonyl (tBoc) or benzyloxycarbonyl (Cbz) or a benzyl protective group, such as, for example, benzyl (Bn).

W and X are as defined for formula (I) above.

One way of preparing intermediate (IX) from compound (VIII) is shown in Scheme 2.

Compounds of the formula (IX) are prepared by oxidation of the alcohol (VIII). There are numerous methods for preparing ketones from secondary alcohols in the literature (see, "Oxidation of Alcohols to Aldehydes and Ketones", Gabriel Tojo, Marcos Fernández, Springer Berlin, 2006, 1-97, and the literature cited therein). The oxidation is preferably carried out under Swern conditions or using Dess-Martin periodinane (see, for example, J. Am. Chem. Soc. 1978, 100, 300-301). Suitable solvents are all solvents which for their part are not oxidized by the oxidizing agent, such as, for example, dichloromethane, chloroform or acetonitrile, if appropriate in the presence of a reaction auxiliary, for example an acid (for example sulphuric acid or hydrochloric acid) or else a base (for example triethylamine or pyridine).

One way of obtaining intermediate (IX) from compound (VIII) is, for example, using Dess-Martin periodinane (15% in dichloromethane, commercially available, for example, from Acros).

Suitable for use as solvents are all customary solvents which are inert under the reaction conditions, such as, for example, cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene), nitriles (for example acetonitrile), carboxylic esters (for example ethyl acetate), amides (for example N,N-dimethylformamide, N,N-dimethylacetamide), dimethyl sulphoxide, 1,3-dimethyl-2-imidazolinone and water, and the reaction can be carried out in mixtures of two or more of these solvents.

The starting materials are employed in equimolar amounts; however, the oxidizing agent can, if required, also be used in excess. The reaction is usually carried out at temperatures of 0° C.-100° C. and preferably at room temperature, but it can also be carried out at the reflux temperature of the reaction mixture. The reaction time varies depending on the scale of the reaction and the reaction temperature, but is generally between a couple of minutes and 48 hours.

After the reaction has ended, compound (IX) is removed from the reaction mixture using one of the customary separation techniques. If required, the compounds are purified by recrystallisation, distillation or chromatography, or they can, if appropriate, also be used for the next step without prior purification.

One way of preparing the intermediate (IVb) from compound (IX) or (VII) is shown in Schemes 3 and 4.

Ketones of the formula (IX) or aldehydes of the formula (VII) are converted into (Z)- or (E)-(IVb), for example by a Wittig or Horner-Wadsworth-Emmons olefination (see, for example, Chem. Rev. 1989, 89, 863-927 and the references cited therein) or, for example, by a Julia olefination (see, for example, Tetrahedron Lett., 1973, 14, 4833-4836) or, for example, by a Peterson olefination (see, for example, J. Org. Chem. 1968, 33, 780). Preferably, the olefination is carried out under Wittig or Horner-Wadsworth-Emmons conditions.

The reagents, such as phosphonium salts and phosphonate reagents, are either commercially available or can be obtained in the manner described in the literature (see, for example, "The Chemistry of Organophosphorus Compounds"; John Wiley & Sons, 1994, Vol 3, 45-184, and the literature cited therein).

Suitable for use as solvents are all customary solvents which are inert under the reaction conditions, such as, for example, cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene), and the reaction can be carried out in mixtures of two or more of these solvents. The preferred solvents are tetrahydrofuran and toluene.

Suitable for use as bases are the bases usually employed in the olefination reactions mentioned above, for example NaH, tBuOK, nBuLi, (see, for example, Rev. 1989, 89, 863-927 and the references cited therein). Suitable acids are those which are usually employed in olefination reactions, such as for example, sulphonic acids or sulphuric acid.

The starting materials are employed in equimolar amounts; however, the phosphonium salts or phosphonates can, if required, also be used in excess. The reaction is usually carried out at temperatures of 0° C.-100° C. and preferably at 0° C.-25° C., but it can also be carried out at the reflux temperature of the reaction mixture. The reaction time varies depending on the scale of the reaction and the reaction temperature, but is generally between a couple of minutes and 48 hours.

After the reaction has ended, compounds (IVb) are removed from the reaction mixture using one of the customary separation techniques. If required, the compounds are purified by recrystallisation, distillation or chromatography, or they can, if appropriate, also be used for the next step without prior purification.

One way of preparing the intermediate (X) from compound (VII) is shown in Scheme 5.

It is known from the literature that alkynylations of aldehydes can be carried out by a Corey-Fuchs reaction (Tetrahedron Lett. 1972, 36, 3769-3772) or a Seyferth-Gilbert homologation (see, for example, J. Org. Chem., 1996, 61, 2540-2541). Alternatively, the alkyne (X) can also be prepared from the aldehyde (VII) using Bestmann-Ohira's reagent analogously to the literature procedures (see, for example, Synthesis 2004, 1, 59-62).

Suitable for use as solvents are all customary solvents which are inert under the reaction conditions, such as, for example, cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride) and halogenated aromatic hydrocarbons (for example chlorobenzene, dichlorobenzene), and the reaction can be carried out in mixtures of two or more of these solvents. The preferred solvents are tetrahydrofuran and toluene.

All known bases can be used in the reaction; however, preference is given to using alkali metal and alkaline earth metal oxides, hydroxides and carbonates. At least one equivalent of the base has to be added to the Bestmann-Ohira's reagent and, if required, the base may be used in excess.

The starting materials are employed in equimolar amounts; however, the Bestmann-Ohira's reagent can, if required, also be used in excess. The reaction is usually carried out at temperatures of 0° C.-60° C. and preferably at 0° C.-40° C., but it can also be carried out at the reflux temperature of the reaction mixture. The reaction time varies depending on the scale of the reaction and the reaction temperature, but is generally between a couple of minutes and 48 hours.

After the reaction has ended, the compounds (VIc) are removed from the reaction mixture using one of the customary separation techniques. If required, the compounds are purified by recrystallisation, distillation or chromatography, or they can, if appropriate, also be used for the next step without prior purification.

Analogously to the method described above, the compounds (XIII) can be synthesized from the corresponding compounds (XII) as shown in Scheme 17. The aldehyde (XII) can be prepared according to procedures known from the literature (for examples, see WO 08/013,925, WO 08/013, 622 and the references cited therein).

One way of preparing the intermediate (IVc) from compound (X) is shown in Scheme 6.

A compound of the general formula (IVc) can be obtained from an alkyne of the general formula (X) by palladium-catalyzed cross-coupling analogously to procedures described in the literature (see, for example, *J. Am. Chem. Soc.* 2003, 125, 13642-13643, *Synlett.* 2006, 18, 2941-2946), namely using a halide of the formula $R^3$-$L^3$-Hal, where the primary halide is reacted in the presence of a catalyst such as, for example, [(π-allyl)PdCl]$_2$, Pd(OAc)$_2$, PdCl$_2$(CH$_3$CN)$_2$, Pd(PPh$_3$)$_4$ or PdCl$_2$(PPh$_3$)$_2$ and, if appropriate, in the presence of other cocatalysts, such as, for example, CuI, Cs$_2$CO$_3$ and 1,3-bis(1-adamantyl)imidazolium chloride, for example in a solvent mixture of DMF and diethyl ether at 0-80° C.

Halides of the formula $R^3$-$L^3$-Hal are either commercially available or can be obtained by methods known from the literature.

Alternatively, the terminal alkyne can also be provided with a protective group, such as for example, by reaction with benzyl chloride in the presence of a palladium(II) catalyst, such as, for example, Pd(OAc)$_2$ or PdCl$_2$(CH$_3$CN)$_2$, and caesium carbonate and also 2-dicyclohexylphosphino-2',4',6'-triisopropylbiphenyl, in tetrahydrofuran or acetonitrile at 0-80° C.

After the reaction has ended, the compounds (IVc) are removed from the reaction mixture using one of the customary separation techniques. If required, the compounds are purified by recrystallisation, distillation or chromatography, or they can, if appropriate, also be used for the next step without prior purification.

Analogously to the method described above, the compounds (Ic) can be synthesized from corresponding compounds (XIII) as shown in Scheme 19.

One way of preparing the intermediate (XI) from compound (X) is shown in Scheme 7.

To form a direct bond between the triple bond ($L^2$ is —C≡C—) and $R^3$, is may be necessary to silylate the terminal alkyne prior to the palladium-catalyzed coupling reaction. Silylations of terminal alkynes are carried out using one of the known methods for silylating terminal alkynes, such as, for example, by adding a base (such as, for example, lithium hexamethyldisilazide) at −78° C. in a polar aprotic solvent to the terminal alkyne and capturing the resulting intermediate using, for example, a silyl halide (*CHEMBIOCHEM,* 2001, 1, 69-75) or silyl triflate.

Suitable for use as solvents are all customary solvents which are inert under the reaction conditions, such as, for example, cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride) and halogenated aromatic hydrocarbons (for example chlorobenzene, dichlorobenzene). The reaction can also be carried out in mixtures of two or more of these solvents. The preferred solvents are tetrahydrofuran and toluene.

All known bases may be employed; however, preference is given to using lithium hexamethyldisilazide, sodium hexamethyldisilazide, potassium hexamethyldisilazide and lithium diisopropylamide for the reaction. At least one equivalent of the base has to be added to the alkyne of the general formula (X), and if required it may be used in excess.

At least one equivalent of silyl chloride or silyl triflate can be used as source of the silyl group in the reaction.

The reaction is usually carried out at temperatures of −78° C.-100° C. and preferably at −20° C.-40° C., but it can also be carried out at the reflux temperature of the reaction mixture. The reaction time varies depending on the scale of the reaction and the reaction temperature, but is generally between a couple of minutes and 48 hours.

After the reaction has ended, the compounds (XI) are removed from the reaction mixture using one of the customary separation techniques. If required, the compounds are purified by recrystallisation, distillation or chromatography, or they can, if appropriate, also be used for the next step without prior purification.

Analogously to the method described above, the compounds (XIV) can be synthesized from corresponding compounds (XIII) as shown in Scheme 18.

One way of preparing the intermediate (IVc) from compound (IX) is shown in Scheme 8.

A compound of the general formula (IVc) can be prepared from an alkyne of the general formula (XI) by palladium-catalyzed coupling reactions, such as, for example, the Sonogashira reaction (*J. Med. Chem.* 2006, 49, 1080-1110), where the halide has the general formula $R^3$-$L^3$-halide in which $L^3$ is a direct bond.

Suitable for use as solvents are all customary solvents which are inert under the reaction conditions, such as, for example, cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), carboxylic esters (for example ethyl acetate), amides (for example N,N-dimethylformamide, N,N-dimethylacetamide), dimethyl sulphoxide and 1,3-dimethyl-2-imidazolinone, and the reaction can be carried out in mixtures of two or more of these solvents. The preferred solvent is N,N-dimethylformamide.

The reaction should be carried out in the presence of the following additives: triethylamine (at least one equivalent based on the compound (XI)), copper(I) iodide (at least 0.1 equivalent based on the compound (XI)) and a source of fluoride such as, for example, tetra-n-butylammonium fluoride (at least 1 equivalent based on the compound (XI) or a slight excess).

A large number of the commercially available palladium (0) catalysts are suitable for use in the reaction; however, preference is given to using tetrakistriphenylphosphine-palladium (Aldrich) in the reaction. The amount of catalyst used is at least 1% to an excess based on the starting material (XI).

The reaction is usually carried out at temperatures of 25° C.-120° C. and preferably at 70° C.-90° C., but it can also be carried out at the reflux temperature of the reaction mixture. The reaction time varies depending on the scale of the reaction and the reaction temperature, but is generally between a couple of minutes and 48 hours.

After the reaction has ended, the compounds (IVc) are removed from the reaction mixture using one of the customary separation techniques. If required, the compounds are purified by recrystallisation, distillation or chromatography, or they can, if appropriate, also be used for the next step without prior purification.

Analogously to the method described above, the compounds (Ic) can be synthesized from corresponding compounds (XIV) as shown in Scheme 20.

One way of synthesizing compounds of the formula (IVa) or (IVb) is shown in Scheme 9.

Thiocarboxamides (V) are either commercially available or can be obtained by methods known from the literature, for example by sulphurization of the corresponding commercially available carboxamide using, for example, Lawesson's reagent (*Org. Synth.* Vol. 7, 1990, 372) at room temperature in a mixture of chloroform/dimethoxyethane (1/2.5). Here, PG represents a protective group as defined in Scheme 2.

α-Haloketones (VIa) and (VIb) are either commercially available or can be obtained by methods known from the literature (for examples see *Molecules*, 2003, 8, 793-865). Alternatively, enolates or silylenol ethers prepared from (XIIa) or (XIIb) can be reacted with a halogen source to give α-haloketones (VIa) or (VIb), (*J. Med. Chem.* 2006, 49, 7877-7886; *J. Med. Chem.* 2006, 49, 1080-1110; *Org. Synth. Vol.* 6, 1988, 175; *Org. Synth. Vol.* 53, 1973, 111). (Scheme 16)

In Scheme 16,

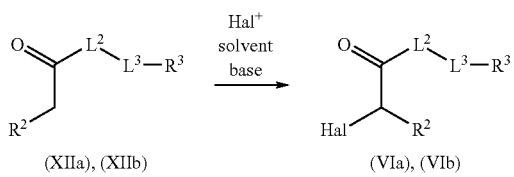

Scheme 16

Hal=Cl, Br or I,
$L^2$=—$C(R^8)_2$—$C(R^8)_2$— for compounds of the formula (VIa) and (XIIa),
$L^2$=—$CR^9$=$CR^9$— for compounds of the formula (VIb) and (XIIb),
$L^3$, $R^2$, $R^3$, $R^8$ and $R^9$ are as defined for formula (I) above.

The thiazoles (IVa) or (IVb) are obtained by a Hantzsch thiazole synthesis from thiocarboxamides (V) and α-haloketones (VIa) or (VIb) (see, for example, "*Comprehensive Heterocyclic Chemistry*", Pergamon Press, 1984; Vol 6, pages 235-363, "*Comprehensive Heterocyclic Chemistry II*", Pergamon Press, 1996; Vol 3, pages 373-474 and the references cited therein, and WO 07/014,290).

Suitable for use as solvents are all customary solvents which are inert under the reaction conditions, such as, for example, alcohols (for example methanol, ethanol, propanol), cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene), nitriles (for example acetonitrile), carboxylic esters (for example ethyl acetate), amides (for example N,N-dimethylformamide, N,N-dimethylacetamide), dimethyl sulphoxide, 1,3-dimethyl-2-imidazolinone, water and acetic acid, or the reaction can be carried out in mixtures of two or more of these solvents. The preferred solvents are N,N-dimethylformamide and ethanol.

If appropriate, an auxiliary base such as, for example, triethylamine is used.

The starting materials are employed in equimolar amounts. However, (V) or (VI) can each also be used in excess. The reaction is usually carried out at temperatures of 0° C.-100° C. and preferably at room temperature, but it can also be carried out at the reflux temperature of the reaction mixture. The reaction time varies depending on the scale of the reaction and the reaction temperature, but is generally between a couple of minutes and 48 hours.

If required, the compounds are purified by recrystallization or chromatography, or they can, if appropriate, also be used in the next step without prior purification.

One way of preparing the intermediate (IVa) from compound (IVb) or (IVc) is shown in Scheme 10.

A triple bond or a double bond is converted by hydrogenation using a suitable catalyst into a single bond. A catalyst for the reaction in Scheme 10 is selected from the hydrogenation catalysts known from the literature ("*Reductions in Organic Chemistry*", Miloš Hudlický, John Wiley & Sons, 1984), such as for example, palladium on activated carbon or Pearlmans catalyst ($Pd(OH)_2$ on activated carbon). Using such a catalyst, it is possible to prepare a compound of the formula (IVa) from a compound of the formula (IVb) or (IVc).

Suitable for use as solvents are all customary solvents which are inert under the reaction conditions, such as, for example, alcohols (for example methanol, ethanol, propanol), cyclic and acyclic ethers (for example diethyl ether, tetrahydrofuran, dioxane, dimethoxyethane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene), nitriles (for example acetonitrile), carboxylic esters (for example ethyl acetate), amides (for example N,N-dimethylformamide, N,N-dimethylacetamide), dimethyl sulphoxide, 1,3-dimethyl-2-imidazolinone, water and acetic acid, or the reaction can be carried out in mixtures of two or more of these solvents. The preferred solvents are N,N-dimethylformamide and ethanol.

The amount of catalyst used is 0.1-90 mol % based on the starting material; preference is given to using 1-30 mol % of the catalyst based on the starting material. The reaction can be carried out at superatmospheric pressure (1-1000 bar) or, preferably, at atmospheric pressure. The reaction is usually carried out at temperatures of 0° C.-150° C. and preferably at room temperature, but it can also be carried out at the reflux temperature of the reaction mixture. The reaction time varies depending on the scale of the reaction and the reaction temperature, but is generally between half an hour and 48 hours.

After the reaction has ended, the compounds (IVa) are removed from the reaction mixture using one of the customary separation techniques. If required, the compounds are purified by recrystallisation, distillation or chromatography, or they can, if appropriate, also be used for the next step without prior purification.

One way of preparing the intermediate (II) from corresponding compounds (IV) is shown in Scheme 11.

A compound of the general formula (IV) is converted into a corresponding compound of the general formula (II) by suitable methods, described in the literature, for removing protective groups ("*Protective Groups in Organic Synthesis*"; Third Edition; Theodora W. Greene, Peter G. M. Wuts; 494-653, and the literature cited therein).

t-Butoxycarbonyl and benzyloxycarbonyl protective groups can be removed in an acidic medium (for example using hydrochloric acid or trifluoroacetic acid). Acetyl protective groups can be removed under basic conditions (using, for example, potassium carbonate or caesium carbonate). Benzylic protective groups can be removed hydrogenolytically using hydrogen in the presence of a catalyst (for example palladium on activated carbon).

Suitable for use as solvents are all customary solvents which are inert under the reaction conditions, such as, for example, alcohols (for example methanol, ethanol, propanol), cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene), nitriles (for example acetonitrile), carboxylic esters (for example ethyl acetate), amides (for example N,N-dimethylformamide, N,N-dimethylacetamide), dimethyl sulphoxide, 1,3-dimethyl-2-imidazolinone, water and acetic acid, or the reaction can be carried out in mixtures of two or more of these solvents.

Acids which can be used for this reaction of deprotecting t-butoxycarbonyl and benzyloxycarbonyl groups are, for example, trifluoroacetic acid, hydrochloric acid or other acids, as described in the literature (for example "*Protective Groups in Organic Synthesis*"; Third Edition; Theodora W. Greene, Peter G. M. Wuts; pp. 494-653).

The reaction is usually carried out at temperatures of 0° C.-150° C. and preferably at room temperature, but it can also be carried out at the reflux temperature of the reaction mixture. The reaction time varies depending on the scale of the reaction and the reaction temperature, but is generally between half an hour and 72 hours.

After the reaction has ended, the compounds (II) are removed from the reaction mixture using one of the customary separation techniques. If required, the compounds are purified by recrystallisation, distillation or chromatography, or they can, if appropriate, also be used for the next step without prior purification. Moreover, it is possible to isolate the compound of the general formula (II) as a salt, for example as a salt of hydrochloric acid or trifluoroacetic acid.

One way of preparing the intermediate (IIa) from compound (IIa') is shown in Scheme 12.

A compound of the general formula (IIa) in which $R^2$=Cl, Br and I is obtained by halogenation from a compound of the general formula (IIa') where $R^2$=H, see, for example, *Org. Lett.*, 2005, 7(2), 299-301; *Angew. Chem., Int. Ed.*, 2004, 43(34), 4471-4475; *Eur. J. Org. Chem.*, 2002, (13), 2126-2135.

Suitable for use as solvents are all customary solvents which are inert under the reaction conditions, such as, for example, alcohols (for example methanol, ethanol, propanol), cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene), carboxylic esters (for example ethyl acetate), amides (for example N,N-dimethylformamide, N,N-dimethylacetamide), dimethyl sulphoxide, 1,3-dimethyl-2-imidazolinone, water and acetic acid, or the reaction can be carried out in mixtures of two or more of these solvents.

Suitable for use as halogen source are, for example, N-bromosuccinimide, N-chlorosuccinimide, N-iodosuccinimide, pyridinium tribromide, bromine, iodine or chlorine.

If appropriate, a base, such as for example, lithium diisopropylamide or butyllithium, may be used to lithiate the 5-position of the thiazole prior to the addition of the electrophilic halogen source.

The reaction can, if appropriate, be carried out using an acid, such as for example acetic acid, sulphuric acid, hydrobromic acid or hydrochloric acid.

The starting materials and the halogenating agent are employed in equimolar amounts. The halogenating agent can also be used in excess. The reaction is usually carried out at temperatures of 0° C.-60° C. and preferably at 0° C.-30° C., but it can also be carried out at the reflux temperature of the reaction mixture. The reaction time varies depending on the scale of the reaction and the reaction temperature, but is generally between a couple of minutes and 48 hours.

After the reaction has ended, the compounds (II) are removed from the reaction mixture using one of the customary separation techniques. If required, the compounds are purified by recrystallisation, distillation or chromatography, or they can, if appropriate, also be used for the next step without prior purification.

One way of preparing compounds of the formula (I) in which Y=oxygen from corresponding compounds (II) is shown in Scheme 13.

Acid halides (III) (B=halogen) or the corresponding carboxylic acids (III) (B=OH) are commercially available or can be prepared by processes described in the literature. Moreover, a substrate of the general formula (III) where B=Cl can be prepared from the corresponding acid (B=OH) by chlorination using processes known from the literature (for example *Tetrahedron* 2005, 61, 10827-10852, and the literature cited therein).

A compound of the general formula (I) where Y=O can be synthesized by a coupling reaction of a compound of the corresponding general formula (II) with a substrate of the general formula (III) where B=Cl, if appropriate in the presence of an acid scavenger/a base.

Suitable for use as solvents are all customary solvents which are inert under the reaction conditions, such as, for example, alcohols (for example methanol, ethanol, propanol), cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene) and nitriles (for example acetonitrile), or the reaction can be carried out in mixtures of two or more of these solvents. The preferred solvents are tetrahydrofuran and dichloromethane.

At least one equivalent of an acid scavenger/a base (for example Hünig base, triethylamine or commercially available polymeric acid scavengers) is employed, based on the starting material of the general formula (II). If the starting material is a salt, at least two equivalents of the acid scavenger are required.

The reaction is usually carried out at temperatures of 0° C.-100° C. and preferably at 20° C.-30° C., but it can also be carried out at the reflux temperature of the reaction mixture. The reaction time varies depending on the scale of the reaction and the reaction temperature, but is generally between a couple of minutes and 48 hours.

After the reaction has ended, the compounds (I) are removed from the reaction mixture using one of the customary separation techniques. If required, the compounds are purified by recrystallisation, distillation or chromatography, or they can, if appropriate, also be used for the next step without prior purification.

Alternatively, a compound of the formula (I) where Y=O can also be synthesized from the corresponding compound of the general formula (II) using a substrate of the general formula (III) where B=OH in the presence of a coupling agent, analogously to the procedures described in the literature (for example *Tetrahedron* 2005, 61, 10827-10852, and the references cited therein).

Suitable coupling agents are, for example, peptide coupling agents (for example, 1-ethyl-3-(30-dimethylamino)carbodiimide mixed with 4-dimethylaminopyridine, 1-ethyl-3-(30-dimethylamino)carbodiimide mixed with hydroxybenzotriazole, bromotri(pyrrolidino)phosphonium hexafluorophosphate, 2-(1H-7-azabenzotriazol-1-yl)-1,1,3,3-tetramethyluronium hexafluorophosphate methanaminium, etc.)

If appropriate, a base, such as for example, triethylamine or Hünig base, may be employed in the reaction.

Suitable for use as solvents are all customary solvents which are inert under the reaction conditions, such as, for example, alcohols (for example methanol, ethanol, propanol), cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene), nitriles (for example acetonitrile) and amides (for example N,N-dimethylformamide, N,N-dimethylacetamide), or the reaction can be carried out in mixtures of two or more of these solvents. The preferred solvents are N,N-dimethylformamide and dichloromethane.

The reaction is usually carried out at temperatures of 0° C.-100° C. and preferably at 0° C.-30° C., but it can also be carried out at the reflux temperature of the reaction mixture. The reaction time varies depending on the scale of the reaction and the reaction temperature, but is generally between a couple of minutes and 48 hours.

After the reaction has ended, the compounds (I) are removed from the reaction mixture using one of the customary separation techniques. If required, the compounds are purified by recrystallisation, distillation or chromatography, or they can, if appropriate, also be used for the next step without prior purification.

One way of preparing compounds of the formula (I) in which Y=sulphur from corresponding compounds (I) in which Y is oxygen is shown in Scheme 14.

Suitable for use as solvents are all customary solvents which are inert under the reaction conditions, such as, for example, alcohols (for example methanol, ethanol, propanol), cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene), nitriles (for example acetonitrile), carboxylic esters (for example ethyl acetate) and amides (for example N,N-dimethylformamide, N,N-dimethylacetamide), or the reaction can be carried out in mixtures of two or more of these solvents. The preferred solvents are chloroform and 1,2-dimethoxyethane.

Suitable sulphurizing agents are, for example, Lawesson's reagent (s. *Tetrahedron* 1986, 42, 6555-6564, *Tetrahedron Lett.* 1993, 46, 7459-7462) and phosphorus pentasulphide. The starting material and the sulphurizing agent are employed in equimolar amounts; however, the sulphurizing agent may, if appropriate, also be employed in excess.

The reaction is usually carried out at temperatures of 0° C.-150° C. and preferably at 0° C.-100° C., but it can also be carried out at the reflux temperature of the reaction mixture. The reaction time varies depending on the scale of the reaction and the reaction temperature, but is generally between a couple of minutes and 48 hours.

After the reaction has ended, the compounds (I) are removed from the reaction mixture using one of the customary separation techniques. If required, the compounds are purified by recrystallisation, distillation or chromatography.

Novel are compounds of the formula (IX) in which

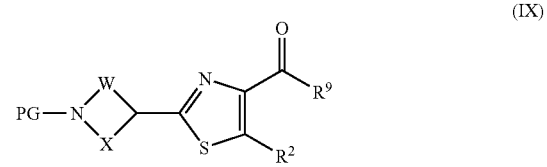

the symbols have the meanings below
PG represents unsubstituted or substituted phenylmethyl (where the substituents independently of one another are selected from the group consisting of methyl, methoxy, nitro, dioxolano), acetyl, $C_1$-$C_4$-alkoxycarbonyl or benzyloxycarbonyl,
$R^9$=$C_1$-$C_4$-alkyl, $C_3$-$C_6$-cycloalkyl,
W, X and $R^2$ have the general, preferred, particularly preferred or very particularly preferred meanings given above.

Novel are compounds of the formula (X) in which

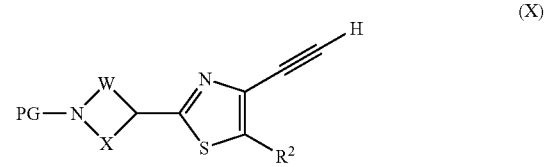

the symbols have the meanings below:
PG represents unsubstituted or substituted phenylmethyl (where the substituents independently of one another are selected from the group consisting of methyl, methoxy, nitro, dioxolano), acetyl, $C_1$-$C_4$-alkoxycarbonyl or benzyloxycarbonyl,
W, X and $R^2$ have the general, preferred, particularly preferred or very particularly preferred meanings given above.

Novel are compounds of the formula (XI) in which

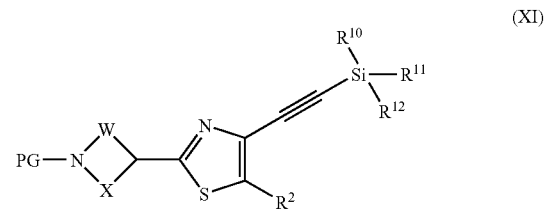

the symbols have the meanings below
PG represents unsubstituted or substituted phenylmethyl (where the substituents independently of one another are selected from the group consisting of methyl, methoxy, nitro, dioxolano), acetyl, $C_1$-$C_4$-alkoxycarbonyl or benzyloxycarbonyl, $R^{10}$, $R^{11}$ and $R^{12}$=$C_1$-$C_4$ alkyl or phenyl, W, X and $R^2$ have the general, preferred, particularly preferred or very particularly preferred meanings given above.

Novel are compounds of the formula (IV) in which

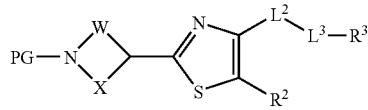

(IV)

the symbols have the meanings below

PG represents unsubstituted or substituted phenylmethyl (where the substituents independently of one another are selected from the group consisting of methyl, methoxy, nitro, dioxolano), acetyl, $C_1$-$C_4$-alkoxycarbonyl or benzyloxycarbonyl, W, X, $L^2$, $L^3$, $R^2$, $R^3$, $R^8$ and $R^9$ have the general, preferred, particularly preferred or very particularly preferred meanings given above.

Novel are compounds of the formula (IIb) and (IIc) in which

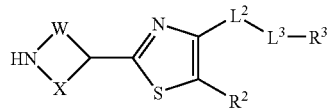

(IIb), (IIc)

the symbols have the meanings below $L^2$ represents —$CR^9$=$CR^9$— for compounds of the formula (IIb)

$L^2$ represents —C≡C— for compounds of the formula (IIc)

W, X, $L^3$, $R^2$, $R^3$, and $R^9$ have the general, preferred, particularly preferred or very particularly preferred meanings given above.

Novel are compounds of the formula (XIII) in which

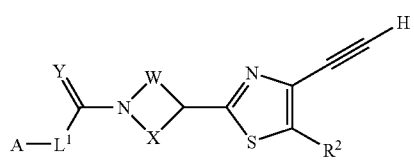

(XIII)

the symbols have the meanings below

A, W, X, Y and $R^2$ have the general, preferred, particularly preferred or very particularly preferred meanings given above.

Novel are compounds of the formula (XIV) in which

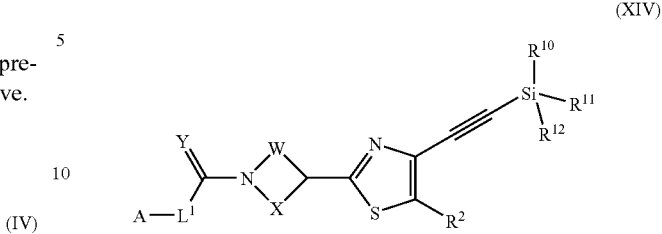

(XIV)

the symbols have the meanings below $R^{10}$, $R^{11}$ and $R^{12}$=$C_1$-$C_4$ alkyl or phenyl, A, W, X, Y, $L^1$ and $R^2$ have the general, preferred, particularly preferred or very particularly preferred meanings given above.

The processes according to the invention for preparing the compounds of the formula (I) are preferably carried out using one or more reaction auxiliaries.

Suitable reaction auxiliaries are, if appropriate, the customary inorganic or organic bases or acid acceptors. These preferably include alkali metal or alkaline earth metal acetates, amides, carbonates, bicarbonates, hydrides, hydroxides or alkoxides, such as for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or isopropoxide, n-, iso-, s- or t-butoxide, or potassium methoxide, ethoxide, n- or isopropoxide, n-, iso-, s- or t-butoxide, furthermore also basic organic nitrogen compounds, such as, for example, trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, 1,4-diazabicyclo[2.2.2]-octane (DABCO), 1,5-diazabicyclo[4.3.0]-non-5-ene (DBN), or 1,8-diazabicyclo[5.4.0]-undec-7-ene (DBU).

The processes according to the invention are preferably carried out using one or more diluents. Suitable diluents are virtually all inert organic solvents. These preferably include aliphatic and aromatic, optionally halogenated hydrocarbons, such as pentane, hexane, heptane, cyclohexane, petroleum ether, benzine, ligroine, benzene, toluene, xylene, methylene chloride, ethylene chloride, chloroform, carbon tetrachloride, chlorobenzene and o-dichlorbenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone or methyl isobutyl ketone, esters, such as methyl acetate or ethyl acetate, nitriles, such as, for example acetonitrile or propionitrile, amides, such as, for example, dimethylformamide, dimethylacetamid and N-methylpyrrolidone, and also dimethyl sulphoxide, tetramethylene sulphone and hexamethylphosphoric triamide and DMPU.

In the processes according to the invention, the reaction temperatures can be varied within a relatively wide range. In general, the processes are carried out at temperatures between 0° C. and 250° C., preferably at temperatures between 10° C. and 185° C.

The processes according to the invention are generally carried out under atmospheric pressure. However, it is also possible to operate under elevated or reduced pressure.

To carry out the processes according to the invention, the starting materials required in each case are generally employed in approximately equimolar amounts. However, it is also possible to use a relatively large excess of in each case one of the components used. Work-up in the processes according to the invention is in each case carried out by customary methods (cf. the Preparation Examples).

The invention furthermore provides the non-medicinal use of the heterocyclyl-substituted thiazoles according to the invention for controlling unwanted microorganisms.

The invention furthermore relates to a composition for controlling unwanted microorganisms which comprises at least one heterocyclyl-substituted thiazole according to the present invention.

Moreover, the invention relates to a method for controlling unwanted microorganisms, characterized in that the heterocyclyl-substituted thiazoles according to the invention are applied to the microorganisms and/or in their habitat.

The invention furthermore relates to a seed treated with at least one heterocyclyl-substituted thiazole according to the invention.

A last subject-matter of the invention relates to a method for protecting seed against unwanted microorganisms by using seed treated with at least one heterocyclyl-substituted thiazole according to the present invention.

The compounds according to the invention have strong microbicidal action and can be used for controlling unwanted microorganisms, such as fungi and bacteria, in crop protection and in the protection of materials.

The heterocyclyl-substituted thiazoles of the formula (I) according to the invention have very good fungicidal properties and can be used in crop protection, for example, for controlling Plasmodiophoromycetes, Oomycetes, Chytridiomycetes, Zygomycetes, Ascomycetes, Basidiomycetes and Deuteromycetes.

In crop protection, bactericides can be used for controlling, for example, Pseudomonadaceae, Rhizobiaceae, Enterobacteriaceae, Corynebacteriaceae and Streptomycetaceae.

The fungicidal compositions according to the invention can be used for the curative or protective control of phytopathogenic fungi. Accordingly, the invention also relates to curative and protective methods for controlling phytopathogenic fungi using the active compounds or compositions according to the invention, which are applied to the seed, the plant or plant parts, the fruit or the soil in which the plants grow.

The compositions according to the invention for controlling phytopathogenic fungi in crop protection comprise an effective, but non-phytotoxic amount of the active compounds according to the invention. "Effective, but non-phytotoxic amount" means an amount of the composition according to the invention which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on a plurality of factors, for example on the fungus to be controlled, the plant, the climatic conditions and the ingredients of the compositions according to the invention.

According to the invention, it is possible to treat all plants and parts of plants. Plants are to be understood here as meaning all plants and plant populations, such as wanted and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by varietal property rights. Parts of plants are to be understood as meaning all above-ground and below-ground parts and organs of the plants, such as shoot, leaf, flower and root, examples which may be mentioned being leaves, needles, stems, trunks, flowers, fruit bodies, fruits and seeds and also roots, tubers and rhizomes. Plant parts also include harvested material and vegetative and generative propagation material, for example seedlings, tubers, rhizomes, cuttings and seeds.

The following plants may be mentioned as plants which can be treated according to the invention: cotton, flax, grapevines, fruit, vegetables, such as Rosaceae sp. (for example pomaceous fruit, such as apples and pears, but also stone fruit, such as apricots, cherries, almonds and peaches and soft fruit such as strawberries), Ribesioidae sp., Juglandaceae sp., Betulaceae sp., Anacardiaceae sp., Fagaceae sp., Moraceae sp., Oleaceae sp., Actimidaceae sp., Lauraceae sp., Musaceae sp. (for example banana trees and plantations), Rubiaceae sp. (for example coffee), Theaceae sp., Sterculiceae sp., Rutaceae sp. (for example lemons, oranges and grapefruit), Solanaceae sp. (for example tomatoes), Liliaceae sp., Asteraceae sp. (for example lettuce), Umbelliferae sp., Cruciferae sp., Chenopodiaceae sp., Cucurbitaceae sp. (for example cucumbers), Alliaceae sp. (for example leek, onions), Papilionaceae sp. (for example peas); major crop plants, such Gramineae sp. (for example maize, lawn, cereals such as wheat, rye, rice, barley, oats, millet and triticale), Asteraceae sp. (for example sunflowers), Brassicaceae sp. (for example white cabbage, red cabbage, broccoli, cauliflowers, brussels sprouts, pak choi, kohlrabi, garden radish, and also oilseed rape, mustard, horseradish and cress), Fabacae sp. (for example beans, peanuts), Papilionaceae sp. (for example soya beans), Solanaceae sp. (for example potatoes), Chenopodiaceae sp. (for example sugarbeet, fodderbeet, swiss chard, beetroot); crop plants and ornamental plants in garden and forest; and also in each case genetically modified varieties of these plants. Preferably, cereal plants are treated according to the invention.

Some pathogens of fungal diseases which can be treated according to the invention may be mentioned by way of example, but not by way of limitation:

Diseases caused by powdery mildew pathogens, such as, for example, *Blumeria* species, such as, for example, *Blumeria graminis*; *Podosphaera* species, such as, for example, *Podosphaera leucotricha*; *Sphaerotheca* species, such as, for example, *Sphaerotheca fuliginea*; *Uncinula* species, such as, for example, *Uncinula necator*;

Diseases caused by rust disease pathogens, such as, for example, *Gymnosporangium* species, such as, for example, *Gymnosporangium sabinae*; *Hemileia* species, such as, for example, *Hemileia vastatrix*; *Phakopsora* species, such as, for example, *Phakopsora pachyrhizi* and *Phakopsora meibomiae*; *Puccinia* species, such as, for example, *Puccinia recondita*, *Puccinia graminis* or *Puccinia striformis*; *Uromyces* species, such as, for example, *Uromyces appendiculatus*;

Diseases caused by pathogens from the group of the Oomycetes, such as, for example, *Albugo* species such as, for example, *Albugo cundida*, *Bremia* species, such as, for example, *Bremia lactucae*; *Peronospora* species, such as, for example, *Peronospora pisi* or *P. brassicae*; *Phytophthora* species, such as, for example *Phytophthora infestans*; *Plasmopara* species, such as, for example, *Plasmopara viticola*; *Pseudoperonospora* species, such as, for example, *Pseudoperonospora humuli* or *Pseudoperonospora cubensis*; *Pythium* species, such as, for example, *Pythium ultimum*;

Leaf blotch diseases and leaf wilt diseases caused, for example, by *Alternaria* species, such as, for example, *Alternaria solani*; *Cercospora* species, such as, for example, *Cercospora beticola*; *Cladiosporium* species, such as, for example, *Cladiosporium cucumerinum*; *Cochliobolus* species, such as, for example, *Cochliobolus sativus* (conidia form: *Drechslera*, Syn: *Helminthosporium*) or *Cochliobolw miyabeanus*; *Colletotrichum* species, such as, for example, *Colletotrichum lindemuthanium*; *Cycloconium* species, such as, for example, *Cycloconium oleaginum*; *Diaporthe* species, such as, for example, *Diaporthe citri*; *Elsinoe* species, such as, for example, *Elsinoe fawcettii*; *Gloeosporium* species, such as, for example, *Gloeosporium laeticolor*; *Glomerella* species, such as, for example, *Glomerella cingulata*; *Guignardia* species, such as, for example, *Guignardia bidwelli*; *Leptosphaeria* species, such as, for example, *Leptosphaeria maculans*; *Magnaporthe* species, such as, for example, *Magnaporthe grisea*; *Microdochium* species, such as, for example, *Microdochium nivale*; *Mycosphaerella* species, such as, for example, *Mycosphaerella graminicola*, *Mycosphaerella arachidicola* or *Mycosphaerella fijiensis*; *Phaeosphaeria* species, such as, for example, *Phaeosphaeria nodorum*; *Pyrenophora* species, such as, for example, *Pyrenophora teres* or *Pyrenophora tritici repentis*; *Ramularia* species, such as, for example, *Ramularia collo-cygni* or *Ramulania areola*; *Rhynchosporium* species, such as, for example, *Rhynchosporium secalis*; *Septoria* species, such as, for example, *Septoria apii* or *Septoria lycopersici*; *Stagonospora* species, such as, for example, *Stagonospora nodorum*; *Typhula* species, such as, for example, *Typhula incarnata*; *Venturia* species, such as, for example, *Venturia inaequalis*;

Root and stem diseases caused, for example, by *Corticium* species, such as, for example, *Corticium graminearum*; *Fusarium* species, such as, for example, *Fusarium oxysporum*; *Gaeumannomyces* species, such as, for example, *Gaeumannomyces graminis*; *Plasmodiophora* species, such as, for example, *Plasmodiophora brassicae*; *Rhizoctonia* species, such as, for example *Rhizoctonia solani*; *Sarocladium* species, such as, for example, *Sarocladium oryzae*; *Sclerotium* species, such as, for example, *Sclerotium oryzae*; *Tapesia* species, such as, for example, *Tapesia acuformis*; *Thielaviopsis* species, such as, for example, *Thielaviopsis basicola*;

Ear and panicle diseases (including maize cobs) caused, for example, by *Alternaria* species, such as, for example, *Alternaria* spp.; *Aspergillus* species, such as, for example, *Aspergillus flavus*; *Cladosporium* species, such as, for example, *Cladosporium cladosporioides*; *Claviceps* species, such as, for example, *Claviceps purpurea*; *Fusarium* species, such as, for example, *Fusarium culmorum*; *Gibberella* species, such as, for example, *Gibberella zeae*; *Monographella* species, such as, for example, *Monographella nivalis*; *Stagonospora* species, such as for example, *Stagonospora nodorum*;

Diseases caused by smut fungi, such as, for example, *Sphacelotheca* species, such as, for example, *Sphacelotheca reiliana*; *Tilletia* species, such as, for example, *Tilletia caries* or *Tilletia controversa*; *Urocystis* species, such as, for example, *Urocystis occulta*; *Ustilago* species, such as, for example, *Ustilago nuda*;

Fruit rot caused, for example, by *Aspergillus* species, such as, for example, *Aspergillus flavus*; *Botrytis* species, such as, for example, *Botrytis cinerea*; *Penicillium* species, such as, for example, *Penicillium expansum* or *Penicillium purpurogenum*; *Rhizopus* species, such as, for example, *Rhizopus stolonifer*; *Sclerotinia* species, such as, for example, *Sclerotinia sclerotiorum*; *Verticilium* species, such as, for example, *Verticilium alboatrum*;

Seed- and soil-borne rot and wilt diseases, and also diseases of seedlings, caused, for example, by *Alternaria* species, such as, for example, *Alternaria brassicicola*; *Aphanomyces* species, such as, for example, *Aphanomyces euteiches*; *Ascochyta* species, such as, for example, *Ascochyta lentis*; *Aspergillus* species, such as, for example, *Aspergillus flavus*; *Cladosporium* species, such as, for example, *Cladosporium herbarum*; *Cochliobolus* species, such as, for example, *Cochliobolus sativus* (conidia form: *Drechslera, Bipolaris* syn: *Helminthosporium*); *Colletotrichum* species, such as, for example, *Colletotrichum coccodes*; *Fusarium* species, such as, for example, *Fusarium culmorum*; *Gibberella* species, such as, for example, *Gibberella zeae*; *Macrophomina* species, such as, for example, *Macrophomina phaseolina*; *Microdochium* species, such as, for example, *Microdochium nivale*; *Monographella* species, such as, for example, *Monographella nivalis*; *Penicillium* species, such as, for example, *Penicillium expansum*; *Phoma* species, such as, for example, *Phoma lingam*; *Phomopsis* species, such as, for example, *Phomopsis sojae*; *Phytophthora* species, such as, for example, *Phytophthora cactorum*; *Pyrenophora* species, such as, for example, *Pyrenophora graminea*; *Pyricularia* species, such as, for example, *Pyricularia oryzae*; *Pythium* species, such as, for example, *Pythium ultimum*; *Rhizoctonia* species, such as, for example, *Rhizoctonia solani*; *Rhizopus* species, such as, for example, *Rhizopus oryzae*; *Sclerotium* species, such as, for example, *Sclerotium rolfsii*; *Septoria* species, such as, for example, *Septoria nodorum*; *Typhula* species, such as, for example, *Typhula incarnata*; *Verticillium* species, such as, for example, *Verticillium dahliae*;

Cancerous diseases, galls and witches' broom caused, for example, by *Nectria* species, such as, for example, *Nectria galligena*;

Wilt diseases caused, for example, by *Monilinia* species, such as, for example, *Monilinia laxa*;

Deformations of leaves, flowers and fruits caused, for example, by *Exobasidium* species, such as, for example, *Exobasidium vexams*; *Taphrina* species, such as, for example, *Taphrina deformans*;

Degenerative diseases of woody plants caused, for example, by *Esca* species, such as, for example, *Phaeomoniella chlamydospora, Phaeoacremonium aleophilum* or *Fomitiporia mediterranea*; *Ganoderma* species, such as, for example, *Ganoderma boninense*;

Diseases of flowers and seeds caused, for example, by *Botrytis* species, such as, for example, *Botrytis cinerea*;

Diseases of plant tubers caused, for example, by *Rhizoctonia* species, such as, for example, *Rhizoctonia solani*; *Helminthosporium* species, such as, for example, *Helminthosporium solani*;

Diseases caused by bacterial pathogens, such as, for example, *Xanthomonas* species, such as, for example, *Xanthomonas campestris* pv. *oryzae*; *Pseudomonas* species, such as, for example, *Pseudomonas syringae* pv. *lachrymans*; *Erwinia* species, such as, for example, *Erwinia amylovora*.

Preference is given to controlling the following diseases of soya beans:

Fungal diseases on leaves, stems, pods and seeds caused, for example, by *alternaria* leaf spot (*Alternaria* spec. *atrans*

*tenuissima*), anthracnose (*Colletotrichum gloeosporoides dematium* var. *truncatum*), brown spot (*Septoria glycines*), *cercospora* leaf spot and blight (*Cercospora kikuchii*), *choanephora* leaf blight (*Choanephora infundibulifera trispora* (Syn.)), *dactuliophora* leaf spot (*Dactuliophora glycines*), downy mildew (*Peronospora manshurica*), *drechslera* blight (*Drechslera glycini*), frogeye leaf spot (*Cercospora sojina*), *leptosphaerulina* leaf spot (*Leptosphaerulina trifolii*), *phyllostica* leaf spot (*Phyllosticta sojaecola*), pod and stem blight (*Phomopsis sojae*), powdery mildew (*Microsphaera diffusa*), *pyrenochaeta* leaf spot (*Pyrenochaeta glycines*), rhizoctonia aerial, foliage, and web blight (*Rhizoctonia solani*), rust (*Phakopsora pachyrhizi Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), *mycoleptodiscus* root rot (*Mycoleptodiscus terrestris*), *neocosmospora* (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active compounds according to the invention also show a strong invigorating action in plants. Accordingly, they are suitable for mobilizing the internal defenses of the plant against attack by unwanted microorganisms.

In the present context, plant-invigorating (resistance-inducing) substances are to be understood as meaning substances which are capable of stimulating the defense system of plants such that, when the treated plants are subsequently inoculated with unwanted microorganisms, they display substantial resistance to these microorganisms.

In the present case, undesired microorganisms are understood as meaning phytopathogenic fungi and bacteria. Thus, the substances according to the invention can be employed for protecting plants against attack by the abovementioned pathogens within a certain period of time after the treatment. The period of time within which their protection is effected is generally extended from 1 to 10 days, preferably 1 to 7 days, after the plants have been treated with the active compounds.

The fact that the active compounds, at the concentrations required for the controlling of plant diseases, are well tolerated by plants permits the treatment of above-ground plant parts, of vegetative propagation material and seed, and of the soil.

In this context, the active compounds according to the invention can be employed particularly successfully for controlling diseases in viticulture and in the cultivation of fruit, potatoes and vegetables, such as, for example, in particular against powdery mildew fungi, Oomycetes, such as, for example, *Phytophthora, Plasmopara, Pseudoperonospora* and *Pythium* species.

The active compounds according to the invention are also suitable for increasing the yield. Moreover, they display a low degree of toxicity and are well tolerated by plants.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (*Mycoplasma*-like organisms) and RLO (*Rickettsia*-like organisms). If appropriate, they can also be employed as insecticides. If appropriate, they can also be employed as intermediates or precursors for the synthesis of other active compounds.

The active compounds according to the invention, in combination with good plant tolerance and favourable toxicity to warm-blooded animals and being tolerated well by the environment, are suitable for protecting plants and plant organs, for increasing harvest yields and for improving the quality of harvested material in agriculture, in horticulture, in animal husbandry, in forests, in gardens and leisure facilities, in the protection of stored products and of materials, and in the hygiene sector. They are preferably employed as crop protection agents. They are active against normally sensitive and resistant species and against all or some stages of development.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for wet seed treatment, a water-soluble powder for slurry treatment, by encrusting, by coating with one or more coats, etc. It is furthermore possible to apply the active compounds by the ultra-low-volume method or to inject the active compound preparation or the active compound itself into the soil.

In the protection of materials, the compositions or active compounds according to the invention can furthermore be employed for protecting industrial materials against attack and destruction by unwanted microorganisms, such as, for example, fungi.

In the present context, industrial materials are understood as meaning nonliving materials which have been made for use in technology. For example, industrial materials which are to be protected by active compounds according to the invention from microbial modification or destruction can be glues, sizes, paper and board, textiles, leather, timber, paints and plastic articles, cooling lubricants and other materials which are capable of being attacked or destroyed by microorganisms. Parts of production plants, for example cooling-water circuits, which can be adversely affected by the multiplication of microorganisms may also be mentioned within the materials to be protected. Industrial materials which may be mentioned with preference for the purposes of the present invention are glues, sizes, paper and board, leather, timber, paints, cooling lubricants and heat-transfer fluids, especially preferably timber. The compositions or active compounds according to the invention can prevent disadvantageous effects such as rotting, decay, discoloration, decoloration or the formation of mould.

The method according to the invention for controlling unwanted fungi can also be employed for protecting storage goods. Here, storage goods are to be understood as meaning natural substances of vegetable or animal origin or process products thereof of natural origin, for which long-term protection is desired. Storage goods of vegetable origin, such as, for example, plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The active compounds according to the invention can prevent disadvantageous effects, such as rotting, decay, discoloration, decoloration or the formation of mould.

Microorganisms capable of degrading or changing the industrial materials which may be mentioned are, for example, bacteria, fungi, yeasts, algae and slime organisms. The active compounds according to the invention preferably act against fungi, in particular moulds, wood-discoloring and wood-destroying fungi (Basidiomycetes) and against slime organisms and algae. Microorganisms of the following genera may be mentioned as examples: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Escherichia*, such as *Escherichia coli*; *Pseudomonas*, such as *Pseudomonas aeruginosa*; *Staphylococcus*, such as *Staphylococcus aureus*.

The present invention furthermore relates to a composition for controlling unwanted microorganisms comprising at least one of the heterocyclyl-substituted thiazoles according to the invention. These are preferably fungicidal compositions comprising auxiliaries, solvents, carriers, surfactants or extenders suitable for use in agriculture.

According to the invention, a carrier is a natural or synthetic, organic or inorganic substance with which the active compounds are mixed or bonded for better applicability, in particular for application to plants or parts of plants or seed. The carrier, which may be solid or liquid, is generally inert and should be suitable for use in agriculture.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite and dolomite, and also synthetic granules of inorganic and organic meals, and granules of organic material, such as paper, sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol/POE and/or POP ethers, acid and/or POP/POE esters, alkylaryl and/or POP/POE ethers, fat and/or POP/POE adducts, POE and/or POP polyol derivatives, POE and/or POP/sorbitan or sugar adducts, alkyl or aryl sulphates, sulphonates and phosphates, or the corresponding PO ether adducts. Furthermore suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and also microencapsulations in polymeric substances.

The active compounds can be used as such, in the form of their formulations or the use forms prepared therefrom, such as ready-to-use solutions, emulsions, water- or oil-based suspensions, powders, wettable powders, pastes, soluble powders, dusts, soluble granules, granules for broadcasting, suspension-emulsion concentrates, natural materials impregnated with active compound, synthetic materials impregnated with active compound, fertilizers and also microencapsulations in polymeric substances. Application is carried out in a customary manner, for example by pouring, spraying, atomizing, broadcasting, dusting, foaming, painting-on, etc. It is furthermore possible to apply the active compounds by the ultra-low-volume method or to inject the preparation of active compound or the active compound itself into the soil. It is also possible to treat the seed of the plants.

The formulations mentioned can be prepared in a manner known per se, for example by mixing the active compounds with at least one customary extender, solvent or diluent, emulsifier, dispersant and/or binder or fixative, wetting agent, water repellant, if appropriate siccatives and UV stabilizers and if appropriate colorants and pigments, antifoams, preservatives, secondary thickeners, glues, gibberellins and other processing auxiliaries.

The compositions according to the invention include not only formulations which are already ready to use and can be applied to the plant or the seed using a suitable apparatus, but also commercial concentrates which have to be diluted with water prior to use.

The active compounds according to the invention can be present as such or in their (commercial) formulations and also in the use forms prepared from these formulations as a mixture with other (known) active compounds, such as insecticides, attractants, sterilants, bactericides, acaricides, nematicides, fungicides, growth regulators, herbicides, fertilizers, safeners and/or semiochemicals.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

Liquefied gaseous extenders or carriers are liquids which are gaseous at ambient temperature and under atmospheric pressure, for example aerosol propellants, such as halogenated hydrocarbons, and also butane, propane, nitrogen and carbon dioxide.

Tackifiers, such as carboxymethylcellulose and natural and synthetic polymers in the form of powders, granules and latices, such as gum arabic, polyvinyl alcohol, polyvinyl acetate, or else natural phospholipids, such as cephalins and lecithins and synthetic phospholipids can be used in the formulations. Other possible additives are mineral and vegetable oils.

If the extender used is water, it is also possible to use, for example, organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

The compositions according to the invention may additionally comprise further components, such as, for example, surfactants. Suitable surfactants are emulsifiers and/or foam-formers, dispersants or wetting agents having ionic or nonionic properties, or mixtures of these surfactants. Examples of these are salts of polyacrylic acid, salts of lignosulphonic acid, salts of phenolsulphonic acid or naphthalene-sulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, ligno-sulphite waste liquors and methylcellulose. The presence of a surfactant is required if one of the active compounds and/or one of the inert carriers is insoluble in water and the application is carried out in water. The proportion of surfactants is between 5 and 40 percent by weight of the compositions according to the invention.

It is possible to use colorants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

Other possible additives are perfumes, mineral or vegetable oils, if appropriate modified, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

If appropriate, it is also possible for other additional components to be present, for example protective colloids, binders, glues, thickeners, thixotropic agents, penetrants, stabilizers, sequestrants, complex foamers. In general, the active compounds can be combined with any solid or liquid additive customarily used for formulation purposes.

The formulations generally comprise between 0.05 and 99% by weight, 0.01 and 98% by weight, preferably between 0.1 and 95% by weight, particularly preferably between 0.5 and 90% by weight, of active compound, very particularly preferably between 10 and 70 percent by weight.

The formulations described above can be employed in a method according to the invention for controlling unwanted microorganisms where the heterocyclyl-substituted thiazoles according to the invention are applied to the microorganisms and/or their habitat.

The active compounds according to the invention, as such or in their formulations, can also be used in a mixture with known fungicides, bactericides, acaricides, nematicides or insecticides, for example to broaden the activity spectrum or to prevent the development of resistance.

Suitable mixing partners are, for example, known fungicides, insecticides, acaricides, nematicides or else bactericides (see also Pesticide Manual, 13th ed.).

A mixture with other known active compounds, such as herbicides, or with fertilizers and growth regulators, safeners and/or semiochemicals is also possible.

Application is carried out in a manner adapted to the use forms.

The invention furthermore comprises a method for treating seed.

A further aspect of the present invention relates in particular to seed treated with at least one of the heterocyclyl-substituted thiazoles according to the invention. The seed according to the invention is used in methods for protecting seed against phytopathogenic harmful fungi. In these methods, seed treated with at least one active compound according to the invention is used.

The compositions and active compounds according to the invention are also suitable for treating seed. A large part of the damage to crop plants which is caused by harmful organisms occurs when the seed is attacked during storage or after the seed is introduced into the soil, and also during and after germination of the plant. This phase is particularly critical since the roots and shoots of the growing plant are particularly sensitive and even minor damage can lead to the death of the whole plant. Protecting the seed and the germinating plant by the use of suitable compositions is therefore of great interest.

The control of phytopathogenic harmful fungi by treating the seed of plants has been known for a long time and is subject-matter of continuous improvements. However, in the treatment of seed, a number of problems are encountered which can not always by resolved in a satisfactory manner. Thus, it is desirable to develop methods for protecting the seed and the germinating plant which dispense with the additional application of crop protection agents after sowing or after the emergence of the plants or where additional applications are at least significantly reduced. It is furthermore desirable to optimize the amount of active compound employed in such a way as to provide maximum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

The present invention therefore also relates to a method for the protection of seed and germinating plants from attack by animal pests and/or phytopathogenic harmful fungi, by treating the seed with a composition according to the invention. The invention likewise relates to the use of the compositions according to the invention for the treatment of seed for protecting the seed and the germinating plant from phytopathogenic fungi. Furthermore, the invention relates to seed which has been treated with a composition according to the invention so as to afford protection from phytopathogenic fungi.

Animal pests and/or phytopathogenic harmful fungi which damage the plant after emergence are primarily controlled by treating the soil and the above-ground parts of the plants with crop protection agents. Owing to concerns with a possible impact of the crop protection agents on the environment and human and animal health, there are efforts to reduce the amount of active compounds applied.

One of the advantages of the present invention is that the particular systemic properties of the compositions according to the invention mean that treatment of the seed with these compositions not only protects the seed itself, but also the resulting plants after emergence, from animal pests and/or phytopathogenic harmful fungi. In this manner, the immediate treatment of the crop at the time of sowing or shortly thereafter can be dispensed with.

It is also to be considered advantageous that the compositions and active compounds according to the invention can be used in particular also for transgenic seed, where the plant growing from this seed is capable of expressing a protein which acts against pests. By treating such a seed with the compositions and active compounds according to the invention, is possible to control certain pests even by the expression of the, for example, insecticidal protein. Surprisingly, a further synergistic effect may be observed here, which further improves the effectiveness of the protection against attack by pests.

The compositions according to the invention are suitable for protecting seed of any plant variety which is employed in agriculture, in the greenhouse, in forests or in horticulture. In particular, this takes the form of seed of cereals (such as wheat, barley, rye, millet and oats), maize, cotton, soya beans, rice, potatoes, sunflowers, beans, coffee, beet (for example sugar beet and fodder beet), peanuts, vegetables (such as tomatoes, cucumbers, onions and lettuce), lawns and ornamental plants. The treatment of seed of cereals (such as wheat, barley, rye and oats), maize and rice is of particular importance.

As also described below, the treatment of transgenic seed with the compositions or active compounds according to the invention is also of particular importance. This takes the form of seed of plants which comprise at least one heterologous gene which governs the expression of a polypeptide or protein with insecticidal properties. The heterologous gene in transgenic seed may be derived, for example, from microorganisms of the species *Bacillus, Rhizobium, Pseudomonas, Serratia, Trichoderma, Clavibacter, Glomus* or *Gliocladium*. This heterologous gene preferably originates from *Bacillus* sp., the gene product having activity against the European corn borer and/or the Western corn root worm. It is particularly preferably a heterologous gene derived from *Bacillus thuringiensis*.

In the context of the present invention, the composition according to the invention is applied to the seed either alone or in a suitable formulation. Preferably, the seed is treated in a state which is stable enough to avoid damage during treatment. In general, the seed may be treated at any point in time between harvest and sowing. The seed usually used has been separated from the plant and freed from cobs, shells, stalks, coats, hairs or the flesh of the fruits. Thus, for example, it is possible to use seed which has been harvested, cleaned and dried to a moisture content of below 15% by weight. Alternatively, it is also possible to use seed which, after drying, has, for example, been treated with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the composition to the seed in the form of a suitable formulation. Suitable formulations and methods for the treatment of seed are known to the skilled worker and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compound which can be used according to the invention can be converted into customary seed dressing formulations, such as solutions, emulsions, suspensions, powders, foams, slurries or other coating materials for seed, and also ULV formulations.

These formulations are prepared in a known manner by mixing the active compounds or active compound combinations with customary additives, such as, for example, customary extenders and also solvents or diluents, colorants, wetting agents, dispersants, emulsifiers, defoamers, preservatives, secondary thickeners, adhesives, gibberellins and also water.

Suitable colorants that may be present in the seed dressing formulations which can be used according to the invention include all colorants customary for such purposes. Use may be made both of pigments, of sparing solubility in water, and of dyes, which are soluble in water. Examples that may be mentioned include the colorants known under the designations rhodamine B, C.I. Pigment Red 112, and C.I. Solvent Red 1.

Suitable wetting agents that may be present in the seed dressing formulations which can be used according to the invention include all substances which promote wetting and are customary in the formulation of active agrochemical compounds. With preference it is possible to use alkylnaphthalene-sulphonates, such as diisopropyl- or diisobutylnaphthalene-sulphonates.

Suitable dispersants and/or emulsifiers that may be present in the seed dressing formulations which can be used according to the invention include all nonionic, anionic, and cationic dispersants which are customary in the formulation of active agrochemical compounds. With preference, it is possible to use nonionic or anionic dispersants or mixtures of nonionic or anionic dispersants. Particularly suitable nonionic dispersants are ethylene oxide-propylene oxide block polymers, alkylphenol polyglycol ethers, and tristyrylphenol polyglycol ethers, and their phosphated or sulphated derivatives. Particularly suitable anionic dispersants are lignosulphonates, polyacrylic salts, and arylsulphonate-formaldehyde condensates.

Suitable defoamers that may be present in the seed dressing formulations which can be used according to the invention include all foam-inhibiting substances which are customary in the formulation of active agrochemical compounds. With preference it is possible to use silicone defoamers and magnesium stearate.

Suitable preservatives that may be present in the seed dressing formulations which can be used according to the invention include all substances which can be used for such purposes in agrochemical compositions. By way of example, mention may be made of dichlorophen and benzyl alcohol hemiformal.

Suitable secondary thickeners that may be present in the seed dressing formulations which can be used according to the invention include all substances which can be used for such purposes in agrochemical compositions. Preferred suitability is possessed by cellulose derivatives, acrylic acid derivatives, xanthan, modified clays, and finely divided silica.

Suitable adhesives that may be present in the seed dressing formulations which can be used according to the invention include all customary binders which can be used in seed dressing. With preference, mention may be made of polyvinylpyrrolidone, polyvinyl acetate, polyvinyl alcohol and tylose.

Suitable gibberellins that may be present in the seed dressing formulations which can be used according to the invention are preferably the gibberellins A1, A3 (=gibberellinic acid), A4 and A7; particularly preferably, gibberellinic acid is used. The gibberellins are known (cf. R. Wegler, "Chemie der Pflanzenschutz- and Schädlingsbekämpfungsmittel", Vol. 2, Springer Verlag, 1970, pp. 401-412).

The seed dressing formulations which can be used according to the invention may be used directly or after dilution with water beforehand to treat seed of any of a very wide variety of types. For instance, the concentrates or the preparations obtainable therefrom by dilution with water may be used to dress the seed of cereals, such as wheat, barley, rye, oats, and triticale, and also the seed of maize, rice, oilseed rape, peas, field beans, cotton, sunflowers, and beets, or else vegetable seed of any of a very wide variety of kinds. The seed dressing formulations which can be used according to the invention or their dilute preparations may also be used to dress seed of transgenic plants. In this context, additional synergistic effects may also arise in interaction with the substances formed by expression.

Suitable mixing equipment for treating seed with the seed dressing formulations which can be used according to the invention or the preparations prepared from them by adding water includes all mixing equipment which can commonly be used for dressing. The specific procedure adopted when dressing comprises introducing the seed into a mixer, adding the particular desired amount of seed dressing formulation, either as it is or following dilution with water beforehand, and carrying out mixing until the formulation is uniformly distributed on the seed. Optionally, a drying operation follows.

The application rate of the seed dressing formulations which can be used according to the invention may be varied within a relatively wide range. It depends on the respective content of the active compounds in the formulations and on the seed. In general, the application rates of active compound combination are between 0.001 and 50 g per kilogram of seed, preferably between 0.01 and 15 g per kilogram of seed.

In addition, the compounds of the formula (I) according to the invention also have very good antimycotic activity. They have a very broad antimycotic activity spectrum in particular against dermatophytes and yeasts, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The enumeration of these fungi does by no means limit the mycotic spectrum which can be covered, but is only for illustration.

Accordingly, the active compounds of the formula (I) according to the invention can be used both in medical and in non-medical applications.

The active compounds can be applied as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, painting-on, etc. It is also possible to apply the active compounds by the ultra-low-volume method or to inject the preparation of active compound or the active compound itself into the soil. It is also possible to treat the seed of the plants.

When using the active compounds according to the invention as fungicides, the application rates can be varied within a relatively wide range, depending on the type of application. The application rate of the active compounds according to the invention is in the treatment of parts of plants, for example leaves: from 0.1 to 10 000 g/ha, preferably from 10 to 1000 g/ha, particularly preferably from 50 to 300 g/ha (when the application is by watering or dripping, it is possible to reduce the application rate even more, in particular when inert substrates such as rock wool or perlite are used);

in the treatment of seed: from 2 to 200 g per 100 kg of seed, preferably from 3 to 150 g per 100 kg of seed, particularly preferably from 2.5 to 25 g per 100 kg of seed, very particularly preferably from 2.5 to 12.5 g per 100 kg of seed;

in soil treatment: from 0.1 to 10 000 g/ha, preferably from 1 to 5000 g/ha.

These application rates are mentioned only in an exemplary manner and are not limiting for the purpose of the invention.

In the veterinary sector and in animal keeping, the active compounds according to the invention are applied in the known manner by enteral administration in the form of, for example, tablets, capsules, drinks, drenches, granules, pastes, boluses, the feed-through method, suppositories, by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like.

When used for livestock, poultry, domestic animals and the like, the active compounds of the formula (I) can be applied as formulations (for example powders, emulsions, flowables) which comprise the active compounds in an amount of from 1 to 80% by weight, either directly or after 100- to 10 000-fold dilution, or else as a chemical bath.

If appropriate, the ready-to-use compositions may comprise further insecticides and, if appropriate, one or more further fungicides.

With respect to possible additional mixing partners, reference is made to the insecticides and fungicides mentioned above.

The compounds according to the invention can also be used for protecting objects which come into contact with salt water or brackish water, such as hulls, screens, nets, buildings, moorings and signalling systems, against colonization.

The compounds according to the invention, alone or in combination with other active compounds, can furthermore be employed as antifouling agents.

The treatment method according to the invention can be used for treating genetically modified organisms (GMOs), for example plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which is/are present in the plant (using for example, antisense technology, cosuppression technology or RNA interference (RNAi) technology. A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, the following effects, which exceed the effects which were actually to be expected, are possible: reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products.

At certain application rates, the active compound combinations according to the invention may also have a strengthening effect in plants. Accordingly, they are also suitable for mobilizing the defense system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably treated according to the invention include all plants with genetic material which bestows upon these plants particularly advantageous useful properties (whether this was achieved by breeding and/or biotechnology is immaterial).

Plants and plant cultivars which are also preferably treated according to the invention are resistant against one or more biotic stress factors, i.e. said plants have a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stress factors. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients or shade avoidance.

Plants and plant cultivars which may also be treated according to the invention are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore by affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or the hybrid effect which results in generally higher yield, vigour, health and resistance towards biotic and abiotic stress factors. Such plants are typically made by crossing an inbred male sterile parent line (the female parent) with another inbred male fertile parent line (the male parent). Hybrid seed is typically harvested from the male sterile plants and sold to growers. Male sterile plants can sometimes (e.g. in corn) be produced by detasseling, (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in the hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimu-*

*rium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes.

Other herbicide-resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species). Plants expressing an exogenous phosphinothricin acetyltransferase have been described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme. Tolerance to HPPD-inhibitors can also be obtained by transforming plants with genes encoding certain enzymes enabling the formation of homogentisate despite the inhibition of the native HPPD enzyme by the HPPD-inhibitor. Tolerance of plants to HPPD inhibitors can also be improved by transforming plants with a gene encoding an enzyme prephenate dehydrogenase in addition to a gene encoding an HPPD-tolerant enzyme.

Still further herbicide-resistant plants are plants that are made tolerant to acetolactate synthase (ALS) inhibitors. Known ALS-inhibitors include, for example, sulphonylurea, imidazolinone, triazolopyrimidines, pyrimidinyloxy(thio) benzoates, and/or sulphonylaminocarbonyltriazolinone herbicides. Different mutations in the ALS enzyme (also known as acetohydroxy acid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Other plants tolerant to imidazolinone and/or sulphonylurea can be obtained by induced mutagenesis, by selection in cell cultures in the presence of the herbicide or by mutation breeding.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, such as the insecticidal crystal proteins listed online at: http://www.lifesci.sussex-.ac.uk/Home/Neil_Crickmore/Bt/, or insecticidal portions thereof, for example proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or 3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR604;

5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/home/Neil_Crickmore/Bt/vip.html, for example proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1a and VIP2A proteins;

7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of the poly(ADP-ribose) polymerase (PARP) gene in the plant cells or plants.
b. plants which contain a stress tolerance-enhancing transgene capable of reducing the expression and/or the activity of the PARG encoding genes of the plants or plant cells;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyl transferase, nicotinamide adenine dinucleotide synthetase or nicotinamide phosphoribosyltransferase.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as, for example:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesized starch in wild type plant cells or plants, so that this modified starch is better suited for special applications.
2) transgenic plants which synthesize non-starch carbohydrate polymers or which synthesize non-starch carbohydrate polymers with altered properties in comparison to wild type plants without genetic modification. Examples are plants which produce polyfructose, especially of the inulin and levan type, plants which produce alpha-1,4-glucans, plants which produce alpha-1,6 branched alpha-1,4-glucans, and plants producing alternan.
3) transgenic plants which produce hyaluronan.

Plants or plant cultivars (that can be obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:
a) plants, such as cotton plants, which contain an altered form of cellulose synthase genes,
b) plants, such as cotton plants, which contain an altered form of rsw2 or rsw3 homologous nucleic acids;
c) plants, such as cotton plants, with an increased expression of sucrose phosphate synthase;
d) plants, such as cotton plants, with an increased expression of sucrose synthase;
e) plants, such as cotton plants, wherein the timing of the plasmodesmatal gating at the basis of the fibre cell is altered, for example through downregulation of fibre-selective β-1,3-glucanase;
f) plants, such as cotton plants, which have fibres with altered reactivity, for example through the expression of the N-acetylglucosaminetransferase gene including nodC and chitin synthase genes.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:

a) plants, such as oilseed rape plants, which produce oil having a high oleic acid content;
b) plants, such as oilseed rape plants, which produce oil having a low linolenic acid content;
c) plants, such as oilseed rape plants, which produce oil having a low level of saturated fatty acids.

Particularly useful transgenic plants which may be treated according to the invention are plants which comprise one or more genes which encode one or more toxins, are the following which are sold under the trade names: YIELD GARD® (for example maize, cotton, soya beans), KnockOut® (for example maize), BiteGard® (for example maize), Bt-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names: Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, that are listed for example in the databases for various national or regional regulatory agencies (see for example http://gmoinfo.jrc.it/gmp_browse.aspx and http://www.agbios.com/dbase.php).

According to the invention, the plants listed can be treated particularly advantageously with the compounds of the general formula (I) or the active compound mixtures according to the invention. The preferred ranges indicated above for the active compounds and mixtures also apply to the treatment of these plants. Particular emphasis is given to treating the plants with the compounds and mixtures specifically indicated in the present text.

The compositions or active compounds according to the invention can also be used to protect plants for a certain period after treatment against attack by the pathogens mentioned. The period for which protection is provided generally extends over 1 to 28 days, preferably over 1 to 14 days, particularly preferably over 1 to 10 days, very particularly preferably over 1 to 7 days, after the treatment of the plants with the active compounds, or over up to 200 days after seed treatment.

Preparation and use of the active compounds of the formula (I) according to the invention is shown in the examples below. However, the invention is not limited to these examples.

General remarks: Unless indicated otherwise, all chromatographic purification and separation steps were carried out on silica gel using a solvent gradient from 0:100 ethyl acetate/cyclohexane to 100:0 ethyl acetate/cyclohexane Preparation of Starting Materials of the Formula (IX)

tert-Butyl 4-(4-acetyl-1,3-thiazol-2-yl)piperidine-1-carboxylate (IX-1)

At room temperature, 1,1,1-triacetoxy-1,1-dihydro-1,2-benziodoxol-3(1H)-one (15% solution in dichloromethane, 28 g) are added dropwise to a solution of tert-butyl 4-[4-(1-hydroxyethyl)-1,3-thiazol-2-yl]piperidine-1-carboxylate (VIII-1, 2.06 g) in dichloromethane (40 ml). The reaction mixture is stirred at room temperature overnight, 5 g of silica gel are then added and the solvent is removed under reduced pressure. The residue is purified chromatographically. This gives tert-butyl 4-(4-acetyl-1,3-thiazol-2-yl)piperidine-1-carboxylate (1.65 g).

$^1$H NMR (DMSO-d6): δ 8.34 (s, 1H), 4.00 (d, 2H), 3.26 (m, 1H), 2.93 (td, 2H), 2.54 (s, 3H), 2.09-2.03 (m, 2H), 1.60 (qd, 2H), 1.41 (s, 9H)

MS (ESI): 255 (M–C(CH3)3+H)

Preparation of Starting Materials of the Formulae (IVa), (IVb) and (IVc)

tert-Butyl 4-[4-(2-phenylethyl)-1,3-thiazol-2-yl]piperidine-1-carboxylate (IV-1)

At 0° C., a solution of tert-butyl 4-carbamothioylpiperidine-1-carboxylate (1.95 g) is added dropwise to a solution of 1-bromo-4-phenylbutan-2-one (2.00 g) in ethanol (20 ml). Under argon, the reaction mixture is stirred at room temperature overnight. Triethylamine (1.7 ml) is added, and the mixture is diluted with ethyl acetate and washed with concentrated sodium chloride solution. The aqueous phase is removed and extracted with ethyl acetate. The combined organic phases are dried over sodium sulphate and concentrated under reduced pressure, which gives a mixture of tert-butyl 4-[4-(2-phenylethyl)-1,3-thiazol-2-yl]piperidine-1-carboxylate and tert-butyl 4-[4-hydroxy-4-(2-phenylethyl)-4,5-dihydro-1,3-thiazol-2-yl]piperidine-1-carboxylate. The two compounds are separated chromatographically. This gives tert-butyl 4-[4-(2-phenylethyl)-1,3-thiazol-2-yl]piperidine-1-carboxylate (800 mg) and tert-butyl 4-[4-hydroxy-4-(2-phenylethyl)-4,5-dihydro-1,3-thiazol-2-yl]piperidine-1-carboxylate (640 mg). Both compounds can be used for Process 1.2 since the latter compound is, under the reaction conditions, converted into the former.

$^1$H NMR (DMSO-d$_6$): δ 7.28-7.25 (m, 2H), 7.22-7.22 (m, 2H), 7.20-7.18 (m, 1H), 7.13 (s, 1H), 4.00 (bs, 2H), 3.35 (s, 2H), 3.16 (m, 1H), 2.95 (s, 4H), 2.00 (d, 2H), 1.52 (qd, 2H), 1.41 (s, 9H) ppm

MS (ESI): 373 ([M+H]$^+$)

tert-Butyl 4-{4-[(E)-2-(naphthalen-1-yl)ethenyl]-1,3-thiazol-2-yl}piperidine-1-carboxylate (IV-2)

Under argon, diethyl 1-naphthylmethylphosphonate (1.88 g) is dissolved in tetrahydrofuran (20 ml) and cooled to 0° C. 757 mg of potassium tert-butoxide are added, whereupon the colour of the solution changes to dark-red. After a further 10 min of stirring, tert-butyl 4-(4-formyl-1,3-thiazol-2-yl)piperidine-1-carboxylate (1.00 g) is added. The mixture is stirred at 0° C. for 30 min and then warmed to room temperature. After a further 20 min, conc. ammonium chloride solution is added. The aqueous phase is separated off and extracted with ethyl acetate. The combined organic phases are dried over sodium sulphate and concentrated, and the residue is purified chromatographically. This gives tert-butyl 4-{4-[(E)-2-(naphthalen-1-yl)ethenyl]-1,3-thiazol-2-yl}piperidine-1-carboxylate (1.16 g) as the E isomer.

$^1$H NMR (DMSO-d$_6$): δ 8.23 (d, 1H), 8.14 (d, 1H), 7.94 (d, 1H), 7.87 (d, 1H), 7.83 (d, 1H), 7.62 (s, 1H), 7.62-7.51 (m, 3H), 7.26 (d, 1H), 4.04 (d, 2H), 3.27 (m, 1H), 2.94 (t, 2H), 2.15-2.05 (m, 2H), 1.66 (qd, 2H), 1.42 (s, 9H) ppm

MS (ESI): 421 ([M+H]$^+$)

tert-Butyl 4-{4-[(Z)-2-(naphthalen-1-yl)ethenyl]-1,3-thiazol-2-yl}piperidine-1-carboxylate (IV-3)

Under argon, (1-naphthylmethyl)triphenylphosphonium chloride (2.96 g) is dissolved in 20 ml of tetrahydrofuran and cooled to 0° C., and potassium tert.-butoxide (757 mg) is added, whereupon the colour of the solution changes to dark-red. After 10 min of stirring, tert-butyl 4-(4-formyl-1,3-thiazol-2-yl)piperidine-1-carboxylate (1.00 g) is added. The mixture is stirred at 0° C. for another 30 min and then slowly warmed to room temperature. After a further 20 min, saturated ammonium chloride solution is added, and the aqueous phase is separated off. After extraction of the aqueous phase with ethyl acetate, the combined organic phases are dried over sodium sulphate and concentrated under reduced pressure. After chromatographic purification, this gives tert-butyl 4-{4-[(Z)-2-(naphthalen-1-yl)ethenyl]-1,3-thiazol-2-yl}piperidine-1-carboxylate (1.2 g, Z isomer).

$^1$H NMR (DMSO-d$_6$): δ 7.92 (t, 2H), 7.87-7.80 (m, 1H), 7.50-7.48 (m, 4H), 7.10 (d, 1H), 6.91 (d, 1H), 6.86 (s, 1H), 3.75 (d, 2H), 2.98 (m, 1H), 2.80 (t, 2H), 1.80-1.70 (m, 2H), 1.40 (s, 9H), 1.30 (qd, 2H) ppm

MS (ESI): 421 ([M+H]$^+$)

tert-Butyl 4-{4-[(1Z)-4-phenylpent-1-en-1-yl]-1,3-thiazol-2-yl}piperidine-1-carboxylate (IV-4)

tert-Butyl 4-(4-formyl-1,3-thiazol-2-yl)piperidine-1-carboxylate (1.00 g) is reacted with triphenyl(3-phenylbutyl)phosphonium iodide (3.53 g) and purified as described in IV-3. This gives tert-butyl 4-{4-[(1Z)-4-phenylpent-1-en-1-yl]-1,3-thiazol-2-yl}piperidine-1-carboxylate (1.23 g) in form of the Z isomer.

$^1$H NMR (DMSO-d$_6$): δ 7.30 (s, 1H), 7.26-7.22 (m, 4H), 7.15 (m, 1H), 6.33 (s, 1H), 5.59 (m, 1H), 3.98 (d, 2H), 3.19 (m, 1H), 3.00-2.83 (m, 5H), 2.06-1.97 (m, 2H), 1.60 (qd, 2H), 1.41 (s, 9H), 1.24 (d, 3H) ppm

MS (ESI): 413 ([M+H]$^+$)

tert-Butyl 4-[4-(3-phenylprop-1-yn-1-yl)-1,3-thiazol-2-yl]piperidine-1-carboxylate (IV-5)

Under argon, benzyl chloride (134 mg), bis(acetonitrile)dichloropalladium(II) (5.5 mg), 2-dicyclohexylphosphino-2',4',6'-triisopropylbiphenyl (30 mg) and caesium carbonate (363 mg) are added to a degassed solution of tert-butyl 4-(4-ethynyl-1,3-thiazol-2-yl)piperidine-1-carboxylate (X-1, 310 mg) in tetrahydrofuran (4 ml). The mixture is then warmed to 65° C. After subsequent cooling, the catalyst is removed by filtration over Celite and the filtrate is concentrated under reduced pressure. After chromatographic purification, this gives tert-butyl 4-[4-(3-phenylprop-1-yn-1-yl)-1,3-thiazol-2-yl]piperidine-1-carboxylate (329 mg).

$^1$H NMR (CD$_3$CN): δ 7.40-7.20 (m, 6H), 4.10-4.05 (m, 2H), 3.83 (s, 2H), 3.15 (m, 1H), 2.94-2.35 (m, 2H), 2.08-2.00 (m, 2H), 1.63 (qd, 2H), 1.43 (s, 9H) ppm

MS (ESI): 383 ([M+H]$^+$)

tert-Butyl 4-[4-(naphthalen-1-ylethynyl)-1,3-thiazol-2-yl]piperidine-1-carboxylate (IV-6)

Tetrakis(triphenylphosphine)palladium(0) (95 mg), copper(I) iodide (31 mg) and triethylamine (200 mg) are added to a solution of tert-butyl 4-{4-[(trimethylsilyl)ethynyl]-1,3-thiazol-2-yl}piperidine-1-carboxylate (XI-1, 600 mg) and 1-bromonaphthalene (375 mg) in degassed N,N-dimethylformamide. After heating to 85° C., tetra-n-butylammonium fluoride (1M in THF, 1.81 ml) is added dropwise. The reaction mixture is then diluted with water and extracted with ethyl acetate. The organic extracts are dried over sodium sulphate and concentrated under reduced pressure. After chromatographic purification, this gives tert-butyl 4-[4-(naphthalen-1-ylethynyl)-1,3-thiazol-2-yl]piperidine-1-carboxylate (576 mg).

$^1$H NMR (CD$_3$CN): δ 8.38 (d, 1H), 7.95 (d, 2H), 7.79 (d, 1H), 7.70 (s, 1H), 7.67-7.50 (m, 3H), 4.12 (d, 2H), 3.24 (m, 1H), 2.94 (t, 2H), 2.15-2.08 (m, 2H), 1.72 (qd, 2H), 1.45 (s, 9H) ppm

MS (ESI): 419 ([M+H]$^+$)

tert-Butyl 4-[4-(pyridin-3-ylethynyl)-1,3-thiazol-2-yl]piperidine-1-carboxylate (IV-7)

tert-Butyl 4-{4-[(trimethylsilyl)ethynyl]-1,3-thiazol-2-yl}piperidine-1-carboxylate (XI-1, 610 mg) is reacted analogously to Example IV-6 with 3-bromopyridine (291 mg). This gives tert-butyl 4-[4-(pyridin-3-ylethynyl)-1,3-thiazol-2-yl]piperidine-1-carboxylate (469 mg).

$^1$H NMR (CD$_3$CN): δ 8.74 (d, 1H), 8.55 (dd, 1H), 7.87 (s, 1H), 7.63 (m, 1H), 7.35 (dd, 1H), 4.10 (d, 2H), 3.20 (m, 2H), 2.93 (t, 2H), 2.13-2.05 (m, 2H), 1.69 (qd, 2H), 1.44 (s, 9H) ppm

MS (ESI): 270 ([M+2H—C=OOC(CH$_3$)$_3$]$^+$)

tert-Butyl 4-{4-[2-(naphthalen-1-yl)ethyl]-1,3-thiazol-2-yl}piperidine-1-carboxylate (IV-8)

tert-Butyl 4-{4-[(Z)-2-(naphthalen-1-yl)ethenyl]-1,3-thiazol-2-yl}piperidine-1-carboxylate (IV-3, 1.5 g) is dissolved in 90 ml of methanol and, at 30° C., hydrogenated under a hydrogen pressure of 10 bar using 10% Pd/C as catalyst. Removal of the catalyst by filtration and removal of the solvent under reduced pressure gives tert-butyl 4-{4-[2-(naphthalen-1-yl)ethyl]-1,3-thiazol-2-yl}piperidine-1-carboxylate (1.48 g) as a colourless oil.

$^1$H NMR (DMSO-d$_6$): δ 8.08 (d, 1H), 7.88 (d, 1H), 7.74 (d, 1H), 7.55-7.45 (m, 2H), 7.42-7.32 (m, 2H), 7.10 (s, 1H), 4.00 (d, 2H), 3.43 (t, 2H), 3.32-3.06 (m, 3H), 2.92 (t, 2H), 2.04-1.98 (m, 2H), 1.58 (qd, 2H), 1.42 (s, 9H) ppm

MS (ESI): 423 ([M+H]$^+$)

Preparation of Starting Materials of the Formula (X)

tert-Butyl 4-(4-ethynyl-1,3-thiazol-2-yl)piperidine-1-carboxylate (X-1)

Under argon, tert-butyl 4-(4-formyl-1,3-thiazol-2-yl)piperidine-1-carboxylate (600 mg) is dissolved in methanol, and potassium carbonate (839 mg) and dimethyl 1-diazo-2-oxopropylphosphonate (786 mg) are added. The mixture is stirred at room temperature for 3 hours. After aqueous work-up, the mixture is extracted with ethyl acetate and the extracts are dried with sodium sulphate and concentrated under reduced pressure. The residue is purified chromatographically. This gives tert-butyl 4-(4-ethynyl-1,3-thiazol-2-yl)piperidine-1-carboxylate (493 mg).

$^1$H NMR (CD$_3$CN): δ 7.51 (s, 1H), 4.07 (d, 2H), 3.36 (s, 1H), 3.16 (m, 1H), 2.90 (t, 2H), 2.10-2.00 (m, 2H), 1.65 (qd, 2H), 1.43 (s, 9H) ppm

MS (ESI): 237 ([M+2H—C(CH$_3$)$_3$]$^+$)

Preparation of Starting Materials of the Formula (XI)

tert-Butyl 4-{4-[(trimethylsilyl)ethynyl]-1,3-thiazol-2-yl}piperidine-1-carboxylate (XI-1)

Under argon, tert-butyl 4-(4-ethynyl-1,3-thiazol-2-yl)piperidine-1-carboxylate (X-1, 940 mg) is dissolved in tetrahydrofuran at −78° C., and lithiumhexamethyldisilazane (1M in hexane, 4.82 ml) is added dropwise. After 30 min, trimethylsilyl chloride (699 mg) is added dropwise, and cooling is removed. The mixture is stirred overnight, saturated ammonium chloride solution is then added and the mixture is extracted with ethyl acetate. The organic extracts are dried over sodium sulphate and concentrated under reduced pressure. The residue is purified chromatographically. This gives tert-butyl 4-{4-[(trimethylsilyl)ethynyl]-1,3-thiazol-2-yl}piperidine-1-carboxylate (1.28 g).

$^1$H NMR (CD$_3$CN): δ 7.42 (s, 1H), 4.05-3.97 (m, 2H), 3.09 (m, 1H), 2.83 (t, 2H), 2.05-1.90 (m, 2H), 1.59 (qd, 2H), 1.37 (s, 9H), 0.17 (s, 9H) ppm

MS (ESI): 309 ([M+2H—C(CH$_3$)$_3$]$^+$)

Preparation of Starting Materials of the Formula (IIa), (IIb) and (IIc)

4-[4-(2-Phenylethyl)-1,3-thiazol-2-yl]piperidine hydrochloride (II-1)

At 0° C., a 2-molar solution of hydrogen chloride in diethyl ether is added dropwise to a solution of tert-butyl 4-[4-(2-phenylethyl)-1,3-thiazol-2-yl]piperidin-1-carboxylate (IV-1, 640 mg). The reaction mixture is stirred at 0° C. and then slowly warmed to room temperature. The mixture is stirred overnight, and the solvent and excess hydrogen chloride are then removed. This gives 4-[4-(2-phenylethyl)-1,3-thiazol-2-yl]piperidine hydrochloride (590 mg).

$^1$H NMR (DMSO-d$_6$): δ 7.25-7.23 (m, 2H), 7.19-7.16 (m, 3H), 7.11 (s, 1H), 3.40-3.30 (m, 5H), 2.98 (s, 4H), 2.21-2.14 (m, 2H), 1.95-1.87 (m, 2H) ppm MS (ESI): 273 ([M−Cl]$^+$)

4-{4-[2-(Naphthalen-1-yl)ethyl]-1,3-thiazol-2-yl}piperidine hydrochloride (II-2)

Under argon and at 0° C., a solution of hydrogen chloride in diethyl ether (2 M, 25 ml) is added to tert-butyl 4-{4-[2-(naphthalen-1-yl)ethyl]-1,3-thiazol-2-yl}piperidine-1-carboxylate (IV-2, 1.40 g). The mixture is stirred at 0° C. and then slowly warmed to room temperature. The mixture is stirred overnight, and the excess acid and solvent are then removed under reduced pressure. This gives 4-{4-[2-(naphthalen-1-yl)ethyl]-1,3-thiazol-2-yl}piperidine hydrochloride (1.28 g).

$^1$H NMR (DMSO-d$_6$): δ 9.18 (bs, 1H), 8.93 (bs, 1H), 8.08 (d, 1H), 7.89 (d, 1H), 7.75 (d, 1H), 7.56-7.45 (m, 2H), 7.73-7.32 (m, 2H), 7.16 (s, 1H), 3.45 (d, 1H), 3.43 (d, 1H), 3.38-3.28 (m, 2H), 3.15-2.95 (m, 4H), 2.25-2.17 (m, 2H), 2.00 (qd, 2H) ppm MS (ESI): 323 ([M−Cl]$^+$)

4-[5-Bromo-4-(2-phenylethyl)-1,3-thiazol-2-yl]piperidine (II-3)

At 0° C., bromine (123 mg) is added dropwise to a solution of 4-[4-(2-phenylethyl)-1,3-thiazol-2-yl]piperidine hydrochloride (II-1, 200 mg) in acetic acid (2 ml). The mixture is stirred for 30 min, and saturated sodium bicarbonate solution is then added. The aqueous phase is separated off and extracted with ethyl acetate. The combined organic phases are dried over anhydrous sodium carbonate, concentrated under reduced pressure and purified chromatographically. This gives 4-[5-bromo-4-(2-phenylethyl)-1,3-thiazol-2-yl]piperidine (127 mg).

log P (pH2.3): 1.72

MS (ESI): 351, 353 ([M+1]$^+$)

Preparation of Compounds of the Formula (Ia)

Method A

2-[5-Methyl-3-(trifluoromethyl)-1H-pyrazol-1-yl]-1-{4-[4-(2-phenylethyl)-1,3-thiazol-2-yl]piperidin-1-yl}ethanone (I-53)

At 0° C., oxalyl chloride (134 mg) and a drop of N,N-dimethylformamide are added to a solution of [5-methyl-3-(trifluoromethyl)-1H-pyrazol-1-yl]acetic acid (185 mg) in dichloromethane. The reaction mixture is stirred at room temperature for 3 h. Solvent and excess reagent are removed under reduced pressure. The solid residue is then once more dissolved in dichloromethane and, at 0° C., added dropwise to a solution of 4-[4-(2-phenylethyl)-1,3-thiazol-2-yl]piperidine hydrochloride (II-1, 250 mg) and triethylamine (410 mg) in dichloromethane. Concentrated ammonium chloride solution is then added to the reaction solution, and the aqueous phase is removed and extracted with ethyl acetate. The combined organic phases are dried over anhydrous sodium sulphate and concentrated. This gives 2-[5-methyl-3-(trifluoromethyl)-1H-pyrazol-1-yl]-1-{4-[4-(2-phenylethyl)-1,3-thiazol-2-yl]piperidin-1-yl}ethanone (122 mg).

$^1$H NMR (DMSO-d$_6$): δ 7.28-7.26 (m, 2H), 7.22-7.21 (m, 2H), 7.19-7.15 (m, 2H), 6.51 (s, 1H), 5.33 (d, 1H), 5.25 (d, 1H), 4.36 (d, 1H), 3.95 (d, 1H), 3.35-3.20 (m, 2H), 2.96 (s, 4H), 2.82 (t, 1H), 2.21 (s, 3H), 2.09 (d, 1H), 2.07 (d, 1H), 1.78 (m, 1H), 1.53 (m, 1H) ppm

MS (ESI): 463 ([M+H]$^+$)

1-{4-[4-(2-Phenylethyl)-1,3-thiazol-2-yl]piperidin-1-yl}pentan-1-one (I-58)

Pentanoyl chloride (133 mg) is added to a solution of 4-[4-(2-phenylethyl)-1,3-thiazol-2-yl]piperidine hydrochloride (II-1, 309 mg) and triethylamine (0.7 ml) in dichloromethane (3 ml). The mixture is stirred overnight, and water is then added. The aqueous phase is separated off and extracted with ethyl acetate, and the combined organic phases are then dried with sodium sulphate and concentrated. The residue is purified. This gives 1-{4-[4-(2-phenylethyl)-1,3-thiazol-2-yl]piperidin-1-yl}pentan-1-one (179 mg).

$^1$H NMR (DMSO-d$_6$): δ 7.27-7.21 (m, 2H), 7.20-7.14 (m, 3H), 7.05 (s, 1H), 4.37 (bs, 1H), 3.95 (bs, 1H), 3.26-3.18 (m, 2H), 2.96 (s, 4H), 2.80 (bs, 1H), 2.33 (t, 2H), 2.04 (d, 2H), 1.55 (bs, 2H), 1.50 (tt, 2H), 1.33 (tq, 2H), 0.90 (t, 3H) ppm

MS (ESI): 357 ([M+H]$^+$)

2-[5-Methyl-3-(trifluoromethyl)-1H-pyrazol-1-yl]-1-(4-{4-[2-(naphthalen-1-yl)ethyl]-1,3-thiazol-2-yl}piperidin-1-yl)ethanone (I-81)

Oxalyl chloride (183 mg) and a drop of N,N-dimethylformamide are added to a solution of [5-methyl-3-(trifluoromethyl)-1H-pyrazol-1-yl]acetic acid (100 mg) in dichloromethane (5 ml). The reaction mixture is stirred at room temperature overnight. After removal of the solvents under reduced pressure, the residue is then dissolved in dichloromethane (5 ml) and a solution of 4-{4-[2-(naphthalen-1-yl)ethyl]-1,3-thiazol-2-yl}piperidine hydrochloride (II-2, 172 mg) and Hünig base (186 mg) in dichloromethane (5 ml) is added dropwise at 0° C. Following the addition of conc. ammonium chloride solution, the aqueous phase is separated off and extracted with ethyl acetate. The combined organic phases are dried over sodium sulphate and concentrated under reduced pressure. The residue is purified chromatographically. This gives 2-[5-methyl-3-(trifluoromethyl)-1H-pyrazol-1-yl]-1-(4-{4-[2-(naphthalen-1-yl)ethyl]-1,3-thiazol-2-yl}piperidin-1-yl)ethanone (150 mg).

$^1$H NMR (DMSO-d$_6$): δ 8.09 (d, 1H), 7.90 (d, 1H), 7.75 (d, 1H), 7.56-7.46 (m, 2H), 7.42-7.33 (m, 2H), 7.12 (s, 1H), 6.45 (s, 1H), 5.22 (bs, 2H), 4.31 (bs, 1H), 3.98 (bs, 1H), 3.44 (t, 2H), 3.35-3.26 (m, 2H), 3.15-3.05 (m, 2H), 2.90 (bs, 1H), 2.23 (s, 3H), 2.15-2.05 (m, 2H), 1.75 (bs, 1H), 1.62 (bs, 1H) ppm

MS (ESI): 513 ([M+H]$^+$)

2-[5-Methyl-3-(trifluoromethyl)-1H-pyrazol-1-yl]-1-{4-[4-(4-phenylpentyl)-1,3-thiazol-2-yl]piperidin-1-yl}ethanone (I-80)

tert-Butyl 4-{4-[(1Z)-4-phenylpent-1-en-1-yl]-1,3-thiazol-2-yl}piperidine-1-carboxylate (IV-4, 1.00 g) is dissolved in methanol and, at 40° C., hydrogenated under an H$_2$-pressure of 10 bar in the presence of Pd/C (10%) for 5 hours. Filtration and removal of the solvent under reduced pressure gives tert-butyl 4-[4-(4-phenylpentyl)-1,3-thiazol-2-yl]piperidine-1-carboxylate (1.00 g) as a colourless oil. This is deprotected analogously to Example II-2. This gives 850 mg of 4-[4-(4-phenylpentyl)-1,3-thiazol-2-yl]piperidine hydrochloride. 169 mg are then reacted analogously to Example I-81 with [5-methyl-3-(trifluoromethyl)-1H-pyrazol-1-yl]acetic acid (100 mg). After chromatographic purification, this gives 2-[5-methyl-3-(trifluoromethyl)-1H-pyrazol-1-yl]-1-{4-[4-(4-phenylpentyl)-1,3-thiazol-2-yl]piperidin-1-yl}ethanone (180 mg) as a colourless oil.

$^1$H NMR (DMSO-d$_6$): δ 7.28-7.23 (m, 2H), 7.19-7.14 (m, 3H), 7.02 (s, 1H), 6.44 (s, 1H), 5.20 (bs, 2H), 4.30 (bs, 1H), 3.95 (bs, 1H), 3.30-3.20 (m, 2H), 2.87 (bs, 1H), 2.72 (m, 1H), 2.67-2.62 (m, 2H), 2.22 (s, 3H), 2.07-2.02 (m, 2H), 1.72 (bs, 1H), 1.63-1.47 (m, 5H), 1.19 (d, 3H) ppm

MS (ESI): 505 ([M+H]$^+$)

1-{4-[5-Bromo-4-(2-phenylethyl)-1,3-thiazol-2-yl]piperidin-1-yl}-2-[5-methyl-3-(trifluoromethyl)-1H-pyrazol-1-yl]ethanone (I-78)

4-[5-Bromo-4-(2-phenylethyl)-1,3-thiazol-2-yl]piperidine (II-3, 127 mg) is reacted analogously to Example I-81 with [5-methyl-3-(trifluoromethyl)-1H-pyrazol-1-yl]acetic acid (118 mg). After chromatographic purification, this gives 1-{4-[5-bromo-4-(2-phenylethyl)-1,3-thiazol-2-yl]piperidin-1-yl}-2-[5-methyl-3-(trifluoromethyl)-1H-pyrazol-1-yl]ethanone (52 mg).

$^1$H NMR (DMSO-d$_6$): δ 7.27-7.22 (m, 2H), 7.18-7.13 (m, 3H), 6.45 (s, 1H), 5.22 (bs, 2H), 4.38 (bs, 1H), 3.95 (bs, 1H), 3.33-3.20 (m, 2H), 2.94 (s, 4H), 2.93 (bs, 1H), 2.22 (s, 3H), 2.09-2.02 (m, 2H), 1.80-1.50 (m, 2H) ppm

MS (ESI): 541 ([M+H]$^+$)

Method B

1-{4-[4-(2-Phenylethyl)-1,3-thiazol-2-yl]piperidin-1-yl}-2-(thiophen-3-yl)ethanone (I-63)

Thiophen-3-ylacetic acid (156 mg) and Hünig base (323 mg) are dissolved in dichloromethane (10 ml) and stirred for 30 min. 4-[4-(2-Phenylethyl)-1,3-thiazol-2-yl]piperidine hydrochloride (II-1, 309 mg), prepared according to Process 1.2, is added, and the mixture is stirred for a further 5 min before bromo-tris-pyrrolidino-phosphonium hexafluorophosphate (599 mg) is added. The reaction mixture is stirred at room temperature overnight. After removal of the solvent under reduced pressure, the residue is purified chromatographically. This gives 1-{4-[4-(2-phenylethyl)-1,3-thiazol-2-yl]piperidin-1-yl}-2-(thiophen-3-yl)ethanone (99 mg).

$^1$H NMR (DMSO-d$_6$): δ 7.44-7.43 (m, 1H), 7.28-7.12 (m, 6H), 7.05 (s, 1H), 6.99 (d, 1H), 4.38 (bs, 1H), 3.99 (bs, 1H), 3.72 (s, 2H), 3.22-3.15 (m, 2H), 2.96 (s, 4H), 2.81 (bs, 1H), 2.00 (d, 2H), 1.52 (m, 2H) ppm

MS (ESI): 397 ([M+H]$^+$)

2-[2-Chloro-5-(trifluoromethyl)phenyl]-1-{4-[4-(2-phenylethyl)-1,3-thiazol-2-yl]piperidin-1-yl}ethanone (I-67)

4-[4-(2-Phenylethyl)-1,3-thiazol-2-yl]piperidine hydrochloride (II-1, 309 mg) is reacted analogously to Example I-63 with [2-chloro-5-(trifluoromethyl)phenyl]acetic acid (262 mg). After chromatographic purification, this gives 2-[2-chloro-5-(trifluoromethyl)phenyl]-1-{4-[4-(2-phenylethyl)-1,3-thiazol-2-yl]piperidin-1-yl}ethanone (210 mg).

$^1$H NMR (DMSO-d$_6$): δ 7.71-7.58 (m, 3H), 7.27-7.12 (m, 5H), 7.07 (s, 1H), 4.37 (bs, 1H), 4.05 (bs, 1H), 3.97 (s, 2H), 3.35-3.23 (m, 2H), 2.97 (s, 4H), 2.88 (bs, 1H), 2.07 (d, 2H), 1.65 (bs, 2H) ppm

MS (ESI): 439 ([M+H]$^+$)

2-(5-Chloro-1-methyl-1H-pyrazol-4-yl)-1-{4-[4-(2-phenylethyl)-1,3-thiazol-2-yl]piperidin-1-yl}ethanone (I-65)

4-[4-(2-Phenylethyl)-1,3-thiazol-2-yl]piperidine hydrochloride (II-1, 280 mg) is reacted analogously to Example I-63 with (5-chloro-1-methyl-1H-pyrazol-4-yl)acetic acid (174 mg). After chromatographic purification, this gives 2-(5-chloro-1-methyl-1H-pyrazol-4-yl)-1-{4-[4-(2-phenylethyl)-1,3-thiazol-2-yl]piperidin-1-yl}ethanone (89 mg).

$^1$H NMR (DMSO-d$_6$): δ 7.40 (s, 1H), 7.26-7.15 (m, 5H), 7.06 (s, 1H), 4.35 (bs, 1H), 4.05 (bs, 1H), 3.76 (s, 3H), 3.49 (s, 2H), 3.30-3.19 (m, 2H), 2.99 (s, 4H), 2.82 (bs, 1H), 2.08-2.00 (m, 2H), 1.58 (bs, 2H) ppm

MS (ESI): 429 ([M+H]$^+$)

2-[4-Chloro-5-methyl-3-(trifluoromethyl)-1H-pyrazol-1-yl]-1-{4-[4-(2-phenylethyl)-1,3-thiazol-2-yl]piperidin-1-yl}propan-1-one (I-64)

4-[4-(2-Phenylethyl)-1,3-thiazol-2-yl]piperidine hydrochloride (II-1, 309 mg) is reacted analogously to Example I-63 with 2-[4-chloro-5-methyl-3-(trifluoromethyl)-1H-pyrazol-1-yl]propanoic acid (282 mg). After chromatographic purification, this gives 2-[4-chloro-5-methyl-3-(trifluoromethyl)-1H-pyrazol-1-yl]-1-{4-[4-(2-phenylethyl)-1,3-thiazol-2-yl]piperidin-1-yl}propan-1-one (165 mg).

$^1$H NMR (DMSO-d$_6$): δ 7.26-7.21 (m, 2H), 7.20-7.13 (m, 3H), 7.06 (s, 1H), 5.70 (m, 1H), 4.30 (bs, 1H), 4.00 (bs, 1H), 3.30-3.19 (m, 2H), 2.96 (s, 5H), 2.26 (d, 3H), 2.08-1.96 (m, 2H), 1.64-1.54 (m, 5H) ppm

MS (ESI): 511 ([M+H]$^+$)

[2,5-Bis(trifluoromethyl)phenyl]{4-[4-(2-phenylethyl)-1,3-thiazol-2-yl]piperidin-1-yl}methanone (I-61)

4-[4-(2-Phenylethyl)-1,3-thiazol-2-yl]piperidine hydrochloride (II-1, 309 mg) is reacted analogously to Example I-63 with 2,5-bis(trifluoromethyl)benzenecarbonyl chloride (304 mg). After chromatographic purification, this gives [2,5-bis(trifluoromethyl)phenyl]{4-[4-(2-phenylethyl)-1,3-thiazol-2-yl]piperidin-1-yl}methanone (282 mg).

$^1$H NMR (DMSO-d$_6$): δ 8.07-7.90 (m, 3H), 7.26-7.21 (m, 2H), 7.20-7.14 (m, 3H), 7.08 (s, 1H), 4.50 (d, 1H), 3.35-3.23 (m, 4H), 2.97 (s, 4H), 2.22-2.10 (m, 1H), 2.00-1.87 (m, 2H), 1.87-1.45 (m, 2H) ppm

MS (ESI): 513 ([M+H]$^+$)

3-(3,4-Dimethoxyphenyl)-1-{4-[4-(2-phenylethyl)-1,3-thiazol-2-yl]piperidin-1-yl}propan-1-one (I-66)

4-[4-(2-Phenylethyl)-1,3-thiazol-2-yl]piperidine hydrochloride (II-1, 309 mg) is reacted analogously to Example I-63 with 3-(3,4-dimethoxyphenyl)propanoic acid (231 mg). After chromatographic purification, this gives 3-(3,4-dimethoxyphenyl)-1-{4-[4-(2-phenylethyl)-1,3-thiazol-2-yl]piperidin-1-yl}propan-1-one (139 mg).

$^1$H NMR (DMSO-d$_6$): δ 7.26-7.21 (m, 2H), 7.20-7.12 (m, 3H), 7.05 (s, 1H), 6.85-6.80 (m, 3H), 6.75-6.71 (dd, 1H), 3.93 (bs, 1H), 3.74 (s, 3H), 3.69 (s, 3H), 3.20 (m, 1H), 2.96 (s, 4H), 2.80-2.74 (m, 2H), 2.65-2.55 (bs, 2H), 2.04-1.97 (m, 2H), 1.58-1.42 (m, 2H), 1.28 (t, 2H) ppm

MS (ESI): 465 ([M+H]$^+$)

2-(1,3-Benzothiazol-2-yl)-1-{4-[4-(2-phenylethyl)-1,3-thiazol-2-yl]piperidin-1-yl}ethanone (I-71)

4-[4-(2-Phenylethyl)-1,3-thiazol-2-yl]piperidine hydrochloride (II-1, 308 mg) is reacted analogously to Example I-63 with 1,3-benzothiazol-2-ylacetic acid (252 mg). After chromatographic purification, this gives 2-(1,3-benzothiazol-2-yl)-1-{4-[4-(2-phenylethyl)-1,3-thiazol-2-yl]piperidin-1-yl}ethanone (109 mg).

$^1$H NMR (DMSO-d$_6$): δ 8.03 (d, 1H), 7.93 (d, 1H), 7.47 (t, 1H), 7.40 (t, 1H), 7.25-7.16 (m, 5H), 7.06 (s, 1H), 4.40 (bs, 1H), 4.34 (s, 2H), 4.09 (bs, 1H), 3.40-3.15 (m, 3H), 2.96 (s, 4H), 2.08-2.02 (m, 2H), 1.65 (bs, 2H) ppm

MS (ESI): 448 ([M+H]$^+$)

2-(2H-Indazol-2-yl)-1-{4-[4-(2-phenylethyl)-1,3-thiazol-2-yl]piperidin-1-yl}ethanone (I-70)

4-[4-(2-Phenylethyl)-1,3-thiazol-2-yl]piperidine hydrochloride (II-1, 309 mg), prepared according to Process 1.2, is reacted analogously to Example I-63 with 2H-indazol-2-ylacetic acid (194 mg). After chromatographic purification, this gives 2-(2H-indazol-2-yl)-1-{-4-[4-(2-phenylethyl)-1,3-thiazol-2-yl]piperidin-1-yl}ethanone (67 mg).

$^1$H NMR (CD$_3$CN): δ 8.10 (s, 1H), 7.71 (d, 1H), 7.60 (d, 1H), 7.29-7.15 (m, 6H), 7.07 (dd, 1H), 6.87 (s, 1H), 5.45 (d, 1H), 5.36 (d, 1H), 4.48 (d, 1H), 4.00 (d, 1H), 3.35-3.23 (m, 2H), 3.00 (s, 4H), 2.86 (t, 1H), 2.18-2.06 (m, 2H), 1.80 (qd, 1H), 1.66 (qd, 1H) ppm

MS (ESI): 431 ([M+H]$^+$)

Method C

2-[5-Methyl-3-(trifluoromethyl)-1H-pyrazol-1-yl]-1-(4-{4-[2-(naphthalen-1-yl)ethyl]-1,3-thiazol-2-yl}piperidin-1-yl)ethanone (I-81)

2-[5-Methyl-3-(trifluoromethyl)-1H-pyrazol-1-yl]-1-{4-[4-(naphthalen-1-ylethynyl)-1,3-thiazol-2-yl]piperidin-1-yl}ethanone (I-50, 157 mg) is dissolved in methanol (1.5 ml) and, at 60° C., reacted with ammonium formiate (195 mg) and 20% Pd(OH)$_2$/C (4 mg) as catalyst. The catalyst is filtered off and the solvent is removed under reduced pressure, giving 2-[5-methyl-3-(trifluoromethyl)-1H-pyrazol-1-yl]-1-(4-{4-[2-(naphthalen-1-yl)ethyl]-1,3-thiazol-2-yl}piperidin-1-yl)ethanone (86 mg) as a colourless oil.

The product was characterized like the compound described beforehand.

Preparation of Compounds of the Formula (Ib)

2-[5-Methyl-3-(trifluoromethyl)-1H-pyrazol-1-yl]-1-(4-{4-[(E)-2-(naphthalen-1-yl)ethenyl]-1,3-thiazol-2-yl}piperidin-1-yl)ethanone (I-27)

tert-Butyl 4-{4-[(E)-2-(naphthalen-1-yl)ethenyl]-1,3-thiazol-2-yl}piperidine-1-carboxylate (IV-2, 171 mg) is deprotected analogously to Example II-2 and then reacted analogously to Example I-81 with [5-methyl-3-(trifluoromethyl)-1H-pyrazol-1-yl]acetic acid (100 mg). After chromatographic purification, this gives 2-[5-methyl-3-(trifluoromethyl)-1H-pyrazol-1-yl]-1-(4-{4-[(E)-2-(naphthalen-1-yl)ethenyl]-1,3-thiazol-2-yl}piperidin-1-yl)ethanone (180 mg).

$^1$H NMR (DMSO-$d_6$): δ 8.23 (d, 1H), 8.16 (d, 1H), 7.95 (d, 1H), 7.88 (d, 1H), 7.83 (d, 1H), 7.64 (s, 1H), 7.63-7.51 (m, 3H), 7.27 (d, 1H), 6.46 (s, 1H), 5.24 (bs, 2H), 4.38 (bs, 1H), 4.03 (bs, 1H), 3.40 (m, 1H), 3.32 (bs, 1H), 2.94 (bs, 1H), 2.24 (s, 3H), 2.23-2.12 (m, 2H), 1.85 (bs, 1H), 1.70 (bs, 1H) ppm

MS (ESI): 511 ([M+H]$^+$)

2-[5-Methyl-3-(trifluoromethyl)-1H-pyrazol-1-yl]-1-(4-{4-[(Z)-2-(naphthalen-1-yl)ethenyl]-1,3-thiazol-2-yl}piperidin-1-yl)ethanone (I-2)

tert-Butyl 4-{4-[(Z)-2-(naphthalen-1-yl)ethenyl]-1,3-thiazol-2-yl}piperidine-1-carboxylate (IV-3, 171 mg) is deprotected analogously to Example II-2 and then reacted analogously to Example I-81 with [5-methyl-3-(trifluoromethyl)-1H-pyrazol-1-yl]acetic acid (100 mg). After chromatographic purification, this gives 2-[5-methyl-3-(trifluoromethyl)-1H-pyrazol-1-yl]-1-(4-{4-[(E)-2-(naphthalen-1-yl)ethenyl]-1,3-thiazol-2-yl}piperidin-1-yl)ethanone (200 mg).

$^1$H NMR (DMSO-$d_6$): δ 7.95-7.92 (m, 2H), 7.87-7.84 (m, 1H), 7.52-7.43 (m, 4H), 7.11 (d, 1H), 6.93 (d, 1H), 6.88 (s, 1H), 6.45 (s, 1H), 5.14 (s, 2H), 4.05 (bs, 1H), 3.74 (bs, 1H), 3.20-3.05 (m, 2H), 2.88 (bs, 1H), 2.24 (s, 3H), 1.90-1.78 (bs, 2H), 1.50 (bs, 1H), 1.35 (bs, 1H) ppm

MS (ESI): 511 ([M+H]$^+$)

2-[5-Methyl-3-(trifluoromethyl)-1H-pyrazol-1-yl]-1-(4-{4-[(1Z)-4-phenylpent-1-en-1-yl]-1,3-thiazol-2-yl}piperidin-1-yl)ethanone (I-3)

tert-Butyl 4-{4-[(1Z)-4-phenylpent-1-en-1-yl]-1,3-thiazol-2-yl}piperidine-1-carboxylate (IV-4, 168 mg) is deprotected analogously to Example II-2 and then reacted analogously to Example I-81 with [5-methyl-3-(trifluoromethyl)-1H-pyrazol-1-yl]acetic acid (100 mg). This gives 2-[5-methyl-3-(trifluoromethyl)-1H-pyrazol-1-yl]-1-(4-{4-[(1Z)-4-phenylpent-1-en-1-yl]-1,3-thiazol-2-yl}piperidin-1-yl)ethanone (200 mg).

$^1$H NMR (DMSO-$d_6$): δ 7.32 (s, 1H), 7.29-7.22 (m, 4H), 7.15 (m, 1H), 6.44 (s, 1H), 6.35 (d, 1H), 5.60 (m, 1H), 5.20 (bs, 2H), 4.30 (bs, 1H), 3.98 (bs, 1H), 3.38-3.25 (m, 2H), 3.05-2.84 (m, 4H), 2.22 (s, 3H), 2.17-2.05 (m, 2H), 1.85-1.56 (m, 2H), 1.26 (d, 3H) ppm

MS (ESI): 503 ([M+H]$^+$)

2-[5-Methyl-3-(trifluoromethyl)-1H-pyrazol-1-yl]-1-(4-{4-[(Z)-2-(2-naphthyl)vinyl]-1,3-thiazol-2-yl}piperidin-1-yl)ethanone (I-20)

(2-Naphthylmethyl)(triphenyl)phosphonium chloride (454 mg) is dissolved in 5 ml of tetrahydrofuran and cooled to 0° C. under argon, and potassium tert.-butoxide (125 mg) is added, whereupon the colour of the solution turns to dark red. After 10 min of stirring, 2-(1-{[5-methyl-3-(trifluoromethyl)-1H-pyrazol-1-yl]acetyl}piperidin-4-yl)-1,3-thiazole-4-carbaldehyde (200 mg) is added. The mixture is stirred at 0° C. for another 30 min and then slowly warmed to room temperature. After a further 20 min, saturated ammonium chloride solution is added, and the aqueous phase is separated off. After extraction of the aqueous phase with ethyl acetate, the combined organic phases are dried over sodium sulphate and concentrated under reduced pressure. After chromatographic purification, this gives 2-[5-methyl-3-(trifluoromethyl)-1H-pyrazol-1-yl]-1-(4-{4-[(Z)-2-(2-naphthyl)vinyl]-1,3-thiazol-2-yl}piperidin-1-yl)ethanone (260 mg).

MS (ESI): 511 ([M+H]$^+$)

2-[5-Methyl-3-(trifluoromethyl)-1H-pyrazol-1-yl]-1-(4-{4-[(E)-2-phenylethenyl]-1,3-thiazol-2-yl}piperidin-1-yl)ethanethione (I-93)

Methoxyphenyldithiophosphonic anhydride (62 mg) is added to a solution of 2-[5-methyl-3-(trifluoromethyl)-1H-pyrazol-1-yl]-1-(4-{4-[(E)-2-phenylethenyl]-1,3-thiazol-2-yl}piperidin-1-yl)-ethanone (141 mg) in chloroform (1 ml) and 1,2-dimethoxyethane (2 ml). The reaction mixture is stirred at room temperature for 24 hours and at 40° C. for 3 hours. After removal of the solvent under reduced pressure, the residue is purified chromatographically. This gives 2-[5-methyl-3-(trifluoromethyl)-1H-pyrazol-1-yl]-1-(4-{4-[(E)-2-phenylethenyl]-1,3-thiazol-2-yl}piperidin-1-yl)-ethanethione (45 mg) as a colourless oil.

$^1$H NMR (CD$_3$CN): δ 7.55 (d, 2H), 7.43 (d, 1H), 7.37 (t, 2H), 7.30-7.28 (m, 2H), 7.18 (d, 1H), 6.39 (s, 1H), 5.41 (d, 1H), 5.26 (s, 2H), 4.42 (d, 1H), 3.54 (t, 1H), 3.45 (m, 1H), 3.38 (t, 1H), 2.31 (s, 3H), 2.30-2.23 (m, 2H), 1.95-1.80 (m, 2H) ppm

MS (ESI): 477 ([M+H]$^+$)

Preparation of Compounds of the Formula (Ic)

2-[5-Methyl-3-(trifluoromethyl)-1H-pyrazol-1-yl]-1-{4-[4-(naphthalen-1-ylethynyl)-1,3-thiazol-2-yl]piperidin-1-yl}ethanone (I-50)

tert-Butyl 4-[4-(naphthalen-1-ylethynyl)-1,3-thiazol-2-yl]piperidine-1-carboxylate (IV-6, 200 mg) is deprotected analogously to Example II-2 and then reacted analogously to Example I-81 with [5-methyl-3-(trifluoromethyl)-1H-pyrazol-1-yl]acetic acid (117 mg). After chromatographic purification, this gives 2-[5-methyl-3-(trifluoromethyl)-1H-pyrazol-1-yl]-1-{4-[4-(naphthalen-1-ylethynyl)-1,3-thiazol-2-yl]piperidin-1-yl}ethanone (112 mg).

$^1$H NMR (CD$_3$CN): δ 8.39 (d, 1H), 7.96 (d, 2H), 7.80 (d, 1H), 7.72 (s, 1H), 7.67-7.50 (m, 3H), 6.37 (s, 1H), 5.05 (s, 2H), 4.45 (bs, 1H), 3.98 (bs, 1H), 3.40-3.20 (m, 2H), 2.93 (bs, 1H), 2.25 (s, 3H), 2.25-2.15 (m, 2H), 1.90-1.75 (m, 2H) ppm

MS (ESI): 509 ([M+H]$^+$)

2-[5-Methyl-3-(trifluoromethyl)-1H-pyrazol-1-yl]-1-{4-[4-(pyridin-3-ylethynyl)-1,3-thiazol-2-yl]piperidin-1-yl}ethanone (I-51)

tert-Butyl 4-[4-(pyridin-3-ylethynyl)-1,3-thiazol-2-yl]piperidine-1-carboxylate (IV-7, 469 mg) is deprotected analogously to Example II-2 giving 3-{[2-(piperidin-4-yl)-1,3-thiazol-4-yl]ethynyl}-pyridine hydrochloride (407 mg). This is immediately reacted at room temperature with [5-methyl-3-(trifluoromethyl)-1H-pyrazol-1-yl]acetic acid (277 mg) in the presence of 4-dimethylaminopyridine (16 mg) and 1-ethyl-3-(3'-dimethylaminopropyl)carbodiimide (268 mg) in dichloromethane (5 ml). Stirring at room temperature overnight, concentration and chromatographic purification gives 2-[5-methyl-3-(trifluoromethyl)-1H-pyrazol-1-yl]-1-{4-[4-(pyridin-3-ylethynyl)-1,3-thiazol-2-yl]piperidin-1-yl}ethanone (65 mg).

$^1$H NMR (CD$_3$CN): δ 8.74 (dd, 1H), 8.59 (dd, 1H), 7.99 (s, 1H), 7.96 (m, 1H), 7.45 (dd, 1H), 6.45 (s, 1H), 5.22 (bs, 2H), 4.35 (bs, 1H), 4.00 (bs, 1H), 3.40-3.20 (m, 3H), 2.22 (s, 3H), 2.17-2.10 (m, 2H), 1.90-1.55 (m, 2H) ppm

MS (ESI): 460 ([M+H]$^+$)

2-[5-Methyl-3-(trifluoromethyl)-1H-pyrazol-1-yl]-1-{4-[4-(3-phenylprop-1-yn-1-yl)-1,3-thiazol-2-yl]piperidin-1-yl}ethanone (I-52)

tert-Butyl 4-[4-(3-phenylprop-1-yn-1-yl)-1,3-thiazol-2-yl]piperidine-1-carboxylate (IV-5, 320 mg) is then deprotected dann analogously to Example II-2 and then reacted analogously to Example I-81 with [5-methyl-3-(trifluoromethyl)-1H-pyrazol-1-yl]acetic acid (174 mg). After chromatographic purification, this gives 2-[5-methyl-3-(trifluoromethyl)-1H-pyrazol-1-yl]-1-{4-[4-(3-phenylprop-1-yn-1-yl)-1,3-thiazol-2-yl]piperidin-1-yl}ethanone (33 mg).

$^1$H NMR (CD$_3$CN): δ 7.46 (s, 1H), 7.42-7.34 (m, 4H), 7.30-7.25 (m, 1H), 6.39 (s, 1H), 5.09 (d, 1H), 5.02 (d, 1H), 4.45 (d, 1H), 3.91 (d, 1H), 3.84 (s, 2H), 3.25 (m, 2H), 2.82 (t, 1H), 2.23 (s, 3H), 2.18-2.05 (m, 2H), 1.82 (qd, 1H), 1.66 (qd, 1H) ppm

MS (ESI): 473 ([M+H]$^+$)

1-[4-(4-Ethynyl-1,3-thiazol-2-yl)piperidin-1-yl]-2-[5-methyl-3-(trifluoromethyl)-1H-pyrazol-1-yl]ethanone (I-86)

Under argon, 2-(1-{[5-methyl-3-(trifluoromethyl)-1H-pyrazol-1-yl]acetyl}piperidin-4-yl)-1,3-thiazol-4-carbaldehyde (200 mg) is dissolved in methanol (5 ml) and potassium carbonate (215 mg) and dimethyl 1-diazo-2-oxopropylphosphonate (199 mg) are added. The mixture is stirred at 40° C. After aqueous work-up, the mixture is extracted with ethyl acetate and the extracts are dried with sodium sulphate and concentrated under reduced pressure. The residue is purified chromatographically. This gives 1-[4-(4-ethynyl-1,3-thiazol-2-yl)piperidin-1-yl]-2-[5-methyl-3-(trifluoromethyl)-1H-pyrazol-1-yl]ethanone (67 mg).

$^1$H NMR (DMSO-d6): δ 7.86 (s, 1H), 6.44 (s, 1H), 5.20 (bs, 2H), 4.31 (bs, 1H), 4.08 (s, 1H), 3.98 (bs, 1H), 3.31 (m, 1H), 3.28 (bs, 1H), 2.88 (bs, 1H), 2.22 (s, 3H), 2.13-2.05 (m, 2H), 1.78 (bs, 1H), 1.61 (bs, 1H) ppm

MS (ESI): 383 ([M+H]$^+$)

2-[5-Methyl-3-(trifluoromethyl)-1H-pyrazol-1-yl]-1-(4-{4-[(trimethylsilyl)ethynyl]-1,3-thiazol-2-yl}piperidin-1-yl)ethanone (I-98)

Under argon, 1-[4-(4-ethynyl-1,3-thiazol-2-yl)piperidin-1-yl]-2-[5-methyl-3-(trifluoromethyl)-1H-pyrazol-1-yl] ethanone (I-86, 525 mg) is, at −78° C., dissolved in tetrahydrofuran (10 ml), and lithium hexamethyldisilazane (1M in hexane, 1.40 ml) is added dropwise. After 10 min, trimethylsilyl chloride (179 mg) is added dropwise. After 30 minutes of stirring, saturated ammonium chloride solution is added and the mixture is extracted with ethyl acetate. The organic extracts are dried over sodium sulphate and concentrated under reduced pressure. The residue is purified chromatographically. This gives 2-[5-methyl-3-(trifluoromethyl)-1H-pyrazol-1-yl]-1-(4-{4-[(trimethylsilyl)ethynyl]-1,3-thiazol-2-yl}piperidin-1-yl)ethanone (540 mg).

$^1$H NMR (DMSO-d6): δ 7.70 (s, 1H), 6.27 (s, 1H), 5.08 (d, 1H), 5.01 (d, 1H), 4.12 (bd, 1H), 3.76 (bd, 1H), 3.05 (t, 1H), 2.59 (t, 1H), 1.97 (s, 3H), 1.88-1.77 (m, 2H), 1.56 (tdd, 1H), 1.30 (tdd, 1H), 0.00 (s, 9H) ppm

MS (ESI): 455 ([M+1]$^+$)

1-(4-{4-[(4-Methoxyphenyl)ethynyl]-1,3-thiazol-2-yl}piperidin-1-yl)-2-[5-methyl-3-(trifluoromethyl)-1H-pyrazol-1-yl]ethanone (I-100)

Tetrakis(triphenylphosphine)palladium(0) (25 mg), copper(I) iodide (8 mg) and triethylamine (53 mg) are added to a solution of 2-[5-methyl-3-(trifluoromethyl)-1H-pyrazol-1-yl]-1-(4-{4-[(trimethylsilyl)ethynyl]-1,3-thiazol-2-yl}piperidin-1-yl)ethanone (I-98, 200 mg) and 1-bromo-4-methoxybenzene (91 mg) in degassed N,N-dimethylformamide (2 ml). After warming to 85° C., tetra-n-butylammonium fluoride (1M in THF, 0.48 ml) is added dropwise. The reaction mixture is then diluted with water and extracted with ethyl acetate. The organic extracts are dried over sodium sulphate and concentrated under reduced pressure. After chromatographic purification, this gives 1-(4-{4-[(4-methoxyphenyl)ethynyl]-1,3-thiazol-2-yl}piperidin-1-yl)-2-[5-methyl-3-(trifluoromethyl)-1H-pyrazol-1-yl]ethanone (84 mg).

$^1$H NMR (DMSO-d6): δ 7.84 (s, 1H), 7.49 (d, 2H), 6.98 (d, 2H), 6.45 (s, 1H), 5.22 (bs, 2H), 4.33 (bs, 1H), 3.98 (bs, 1H), 3.80 (s, 3H), 3.34 (m, 1H), 3.28 (bs, 1H), 2.89 (bs, 1H), 2.22 (s, 3H), 2.15-2.09 (m, 2H), 1.80 (bs, 1H), 1.63 (bs, 1H) ppm

MS (ESI): 489 ([M+H]$^+$)

1-(4-{4-[(2-Methoxyphenyl)ethynyl]-1,3-thiazol-2-yl}piperidin-1-yl)-2-[5-methyl-3-(trifluoromethyl)-1H-pyrazol-1-yl]ethanone (I-103)

Tetrakis(triphenylphosphine)palladium(0) (25 mg), copper(I) iodide (7 mg) and triethylamine (48 mg) are added to a solution of 1-[4-(4-ethynyl-1,3-thiazol-2-yl)piperidin-1-yl]-2-[5-methyl-3-(trifluoromethyl)-1H-pyrazol-1-yl]ethanone (I-86, 150 mg) and 1-iodo-2-methoxybenzene (101 mg) in degassed N,N-dimethylformamide (1.5 ml). After 2 hours of stirring at 85° C., the reaction mixture is then diluted with water and extracted with ethyl acetate. The organic extracts are dried over sodium sulphate and concentrated under reduced pressure. After chromatographic purification, this gives 1-(4-{4-[(2-methoxyphenyl)ethynyl]-1,3-thiazol-2-yl}piperidin-1-yl)-2-[5-methyl-3-(trifluoromethyl)-1H-pyrazol-1-yl]ethanone (100 mg).

$^1$H NMR (DMSO-d6): δ 7.86 (s, 1H), 7.47 (dd, 1H), 7.40 (td, 1H), 7.09 (d, 1H), 6.98 (td, 1H), 6.45 (s, 1H), 5.23 (bs, 2H), 4.33 (bs, 1H), 3.98 (bs, 1H), 3.86 (s, 3H), 3.35 (m, 1H), 3.29 (bs, 1H), 2.89 (bs, 1H), 2.23 (s, 3H), 2.15-2.08 (m, 2H), 1.80 (bs, 1H), 1.63 (bs, 1H) ppm

MS (ESI): 489 ([M+H]$^+$)

EXAMPLES

The compounds of the formula I listed in Table 1 below can be obtained analogously to the methods given above.

TABLE I

[Structure: A—L¹—C(=Y)—N(—W—X—) ring attached to thiazole with L²—L³—R³ at 4-position and R² at 5-position]

where

| Ex | A | L¹ | Y | W | X | R² | L² | L³ | R³ | log p |
|---|---|---|---|---|---|---|---|---|---|---|
| I-1 | 5-methyl-3-(trifluoromethyl)-1H-pyrazol-1-yl | CH₂ | O | CH₂CH₂ | CH₂CH₂ | H | CH=CH (Z) | bond | phenyl | 3.91[b] |
| I-2 | 5-methyl-3-(trifluoromethyl)-1H-pyrazol-1-yl | CH₂ | O | CH₂CH₂ | CH₂CH₂ | H | CH=CH (Z) | bond | naphthalen-1-yl | 4.52[b] |
| I-3 | 5-methyl-3-(trifluoromethyl)-1H-pyrazol-1-yl | CH₂ | O | CH₂CH₂ | CH₂CH₂ | H | CH=CH (Z) | CH₂CHCH₃ | phenyl | 4.84[b] |
| I-4 | 5-methyl-3-(trifluoromethyl)-1H-pyrazol-1-yl | CH₂ | O | CH₂CH₂ | CH₂CH₂ | H | CH=CH (Z) | bond | cyclohexyl | |
| I-5 | 3-(trifluoromethyl)-1H-pyrazol-1-yl | CH₂ | O | CH₂CH₂ | CH₂CH₂ | H | CH=CH (Z) | bond | cyclohexyl | |
| I-6 | 4-chloro-5-methyl-3-(trifluoromethyl)-1H-pyrazol-1-yl | CH₂ | O | CH₂CH₂ | CH₂CH₂ | H | CH=CH (Z) | bond | cyclohexyl | |
| I-7 | 3-(trifluoromethyl)-1H-pyrazol-1-yl | CH₂ | O | CH₂CH₂ | CH₂CH₂ | H | CH=CH (Z) | bond | phenyl | 3.72[b] |
| I-8 | 4-chloro-5-methyl-3-(trifluoromethyl)-1H-pyrazol-1-yl | CH₂ | O | CH₂CH₂ | CH₂CH₂ | H | CH=CH (Z) | bond | phenyl | 4.56[b] |
| I-9 | 5-methyl-3-(trifluoromethyl)-1H-pyrazol-1-yl | CH₂ | O | CH₂CH₂ | CH₂CH₂ | H | CH=CH (Z) | bond | 4-chlorophenyl | 4.41[b] |
| I-10 | 3-(trifluoromethyl)-1H-pyrazol-1-yl | CH₂ | O | CH₂CH₂ | CH₂CH₂ | H | CH=CH (Z) | bond | 4-chlorophenyl | 4.2[b] |
| I-11 | 4-chloro-5-methyl-3-(trifluoromethyl)-1H-pyrazol-1-yl | CH₂ | O | CH₂CH₂ | CH₂CH₂ | H | CH=CH (Z) | bond | 4-chlorophenyl | 4.92[b] |
| I-12 | 5-methyl-3-(trifluoromethyl)-1H-pyrazol-1-yl | CH₂ | O | CH₂CH₂ | CH₂CH₂ | H | CH=CH (Z) | bond | 4-methoxyphenyl | 3.9[b] |
| I-13 | 3-(trifluoromethyl)-1H-pyrazol-1-yl | CH₂ | O | CH₂CH₂ | CH₂CH₂ | H | CH=CH (Z) | bond | 4-methoxyphenyl | |
| I-14 | 4-chloro-5-methyl-3-(trifluoromethyl)-1H-pyrazol-1-yl | CH₂ | O | CH₂CH₂ | CH₂CH₂ | H | CH=CH (Z) | bond | 4-methoxyphenyl | 4.46[b] |
| I-15 | 5-methyl-3-(trifluoromethyl)-1H-pyrazol-1-yl | CH₂ | O | CH₂CH₂ | CH₂CH₂ | H | CH=CH (Z) | bond | 3-(trifluoromethyl)phenyl | 4.51[b] |
| I-16 | 3-(trifluoromethyl)-1H-pyrazol-1-yl | CH₂ | O | CH₂CH₂ | CH₂CH₂ | H | CH=CH (Z) | bond | 3-(trifluoromethyl)phenyl | 4.3[b] |
| I-17 | 4-chloro-5-methyl-3-(trifluoromethyl)-1H-pyrazol-1-yl | CH₂ | O | CH₂CH₂ | CH₂CH₂ | H | CH=CH (Z) | bond | 3-(trifluoromethyl)phenyl | 5.03[b] |
| I-18 | 3-(trifluoromethyl)-1H-pyrazol-1-yl | CH₂ | O | CH₂CH₂ | CH₂CH₂ | H | CH=CH (Z) | bond | naphthalen-1-yl | 4.35[b] |
| I-19 | 4-chloro-5-methyl-3-(trifluoromethyl)-1H-pyrazol-1-yl | CH₂ | O | CH₂CH₂ | CH₂CH₂ | H | CH=CH (Z) | bond | naphthalen-1-yl | 5.14[b] |
| I-20 | 5-methyl-3-(trifluoromethyl)-1H-pyrazol-1-yl | CH₂ | O | CH₂CH₂ | CH₂CH₂ | H | CH=CH (Z) | bond | naphthalen-2-yl | 4.61[b] |
| I-21 | 3-(trifluoromethyl)-1H-pyrazol-1-yl | CH₂ | O | CH₂CH₂ | CH₂CH₂ | H | CH=CH (Z) | bond | naphthalen-2-yl | 4.35[b] |
| I-22 | 4-chloro-5-methyl-3-(trifluoromethyl)-1H-pyrazol-1-yl | CH₂ | O | CH₂CH₂ | CH₂CH₂ | H | CH=CH (Z) | bond | naphthalen-2-yl | 5.08[b] |
| I-23 | 5-methyl-3-(trifluoromethyl)-1H-pyrazol-1-yl | CH₂ | O | CH₂CH₂ | CH₂CH₂ | H | CH=CH (Z) | CH₂ | phenyl | 4.41[b] |
| I-24 | 3-(trifluoromethyl)-1H-pyrazol-1-yl | CH₂ | O | CH₂CH₂ | CH₂CH₂ | H | CH=CH (Z) | CH₂ | phenyl | |
| I-25 | 4-chloro-5-methyl-3-(trifluoromethyl)-1H-pyrazol-1-yl | CH₂ | O | CH₂CH₂ | CH₂CH₂ | H | CH=CH (Z) | CH₂ | phenyl | |

TABLE I-continued

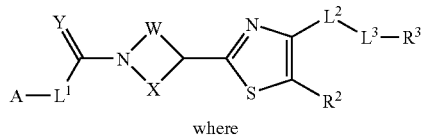

where

| Ex | A | L¹ | Y | W | X | R² | L² | L³ | R³ | log p |
|---|---|---|---|---|---|---|---|---|---|---|
| I-26 | 5-methyl-3-(trifluoromethyl)-1H-pyrazol-1-yl | $CH_2$ | O | $CH_2CH_2$ | $CH_2CH_2$ | H | CH=CH (E) | bond | phenyl | 3.99[b] |
| I-27 | 5-methyl-3-(trifluoromethyl)-1H-pyrazol-1-yl | $CH_2$ | O | $CH_2CH_2$ | $CH_2CH_2$ | H | CH=CH (E) | bond | naphthalen-1-yl | 4.63[b] |
| I-28 | 5-methyl-3-(trifluoromethyl)-1H-pyrazol-1-yl | $CH_2$ | O | $CH_2CH_2$ | $CH_2CH_2$ | H | CH=CH (E) | $CH_2$ | $CF_3$ | |
| I-29 | 5-methyl-3-(trifluoromethyl)-1H-pyrazol-1-yl | $CH_2$ | O | $CH_2CH_2$ | $CH_2CH_2$ | H | CH=CH (E) | $CH_2$ | tert-butyl | |
| I-30 | 5-methyl-3-(trifluoromethyl)-1H-pyrazol-1-yl | $CH_2$ | O | $CH_2CH_2$ | $CH_2CH_2$ | H | CH=CH (E) | $CH_2$ | ethenyl | |
| I-31 | 5-methyl-3-(trifluoromethyl)-1H-pyrazol-1-yl | $CH_2$ | O | $CH_2CH_2$ | $CH_2CH_2$ | H | CH=CH (E) | $CH_2$ | ethynyl | |
| I-32 | 5-methyl-3-(trifluoromethyl)-1H-pyrazol-1-yl | $CH_2$ | O | $CH_2CH_2$ | $CH_2CH_2$ | H | CH=CH (E) | $CH_2$ | cyclohexyl | |
| I-33 | 5-methyl-3-(trifluoromethyl)-1H-pyrazol-1-yl | $CH_2$ | O | $CH_2CH_2$ | $CH_2CH_2$ | H | CH=CH (E) | $CH_2$ | morpholin-4-yl | |
| I-34 | 5-methyl-3-(trifluoromethyl)-1H-pyrazol-1-yl | $CH_2$ | O | $CH_2CH_2$ | $CH_2CH_2$ | H | CH=CH (E) | bond | pyridin-3-yl | |
| I-35 | 5-(difluoromethyl)-3-methyl-1H-pyrazol-1-yl | $CH_2$ | O | $CH_2CH_2$ | $CH_2CH_2$ | H | $CH_2CH_2$ | bond | phenyl | 3.37[b] |
| I-36 | 3,5-dichloro-1H-pyrazol-1-yl | $CH_2$ | O | $CH_2CH_2$ | $CH_2CH_2$ | H | $CH_2CH_2$ | bond | phenyl | |
| I-37 | 3,5-dibromo-1H-pyrazol-1-yl | $CH_2$ | O | $CH_2CH_2$ | $CH_2CH_2$ | H | $CH_2CH_2$ | bond | phenyl | |
| I-38 | 2-bromo-5-(trifluoromethyl)phenyl | $CH_2$ | O | $CH_2CH_2$ | $CH_2CH_2$ | H | $CH_2CH_2$ | bond | phenyl | |
| I-39 | 5-bromo-2-methylphenyl | $CH_2$ | O | $CH_2CH_2$ | $CH_2CH_2$ | H | $CH_2CH_2$ | bond | phenyl | |
| I-40 | 2,5-dichlorophenyl | $CH_2$ | O | $CH_2CH_2$ | $CH_2CH_2$ | H | $CH_2CH_2$ | bond | phenyl | |
| I-41 | 2,5-dibromophenyl | $CH_2$ | O | $CH_2CH_2$ | $CH_2CH_2$ | H | $CH_2CH_2$ | bond | phenyl | |
| I-42 | 5-iodo-2-methylphenyl | $CH_2$ | O | $CH_2CH_2$ | $CH_2CH_2$ | H | $CH_2CH_2$ | bond | phenyl | |
| I-43 | 3,5-bis(trifluoromethyl)-1H-pyrazol-1-yl | $CH_2$ | O | $CH_2CH_2$ | $CH_2CH_2$ | H | $CH_2CH_2$ | bond | naphthalen-1-yl | 4.89[b] |
| I-44 | 5-(difluoromethyl)-3-methyl-1H-pyrazol-1-yl | $CH_2$ | O | $CH_2CH_2$ | $CH_2CH_2$ | H | $CH_2CH_2$ | bond | naphthalen-1-yl | |
| I-45 | 3,5-dichloro-1H-pyrazol-1-yl | $CH_2$ | O | $CH_2CH_2$ | $CH_2CH_2$ | H | $CH_2CH_2$ | bond | naphthalen-1-yl | |
| I-46 | 3,5-dibromo-1H-pyrazol-1-yl | $CH_2$ | O | $CH_2CH_2$ | $CH_2CH_2$ | H | $CH_2CH_2$ | bond | naphthalen-1-yl | |
| I-47 | 2-chloro-5-(trifluoromethyl)phenyl | $CH_2$ | O | $CH_2CH_2$ | $CH_2CH_2$ | H | $CH_2CH_2$ | bond | naphthalen-1-yl | |
| I-48 | 2-bromo-5-(trifluoromethyl)phenyl | $CH_2$ | O | $CH_2CH_2$ | $CH_2CH_2$ | H | $CH_2CH_2$ | bond | naphthalen-1-yl | |
| I-49 | 5-bromo-2-methylphenyl | $CH_2$ | O | $CH_2CH_2$ | $CH_2CH_2$ | H | $CH_2CH_2$ | bond | naphthalen-1-yl | |
| I-50 | 5-methyl-3-(trifluoromethyl)-1H-pyrazol-1-yl | $CH_2$ | O | $CH_2CH_2$ | $CH_2CH_2$ | H | C≡C | bond | naphthalen-1-yl | 4.66[c]; 4.5[b] |
| I-51 | 5-methyl-3-(trifluoromethyl)-1H-pyrazol-1-yl | $CH_2$ | O | $CH_2CH_2$ | $CH_2CH_2$ | H | C≡C | bond | pyridin-3-yl | 2.68[b] |
| I-52 | 5-methyl-3-(trifluoromethyl)-1H-pyrazol-1-yl | $CH_2$ | O | $CH_2CH_2$ | $CH_2CH_2$ | H | C≡C | $CH_2$ | phenyl | 3.88[b] |

TABLE I-continued

| Ex | A | L¹ | Y | W | X | R² | L² | L³ | R³ | log p |
|---|---|---|---|---|---|---|---|---|---|---|
| I-53 | 5-methyl-3-(trifluoromethyl)-1H-pyrazol-1-yl | CH₂ | O | CH₂CH₂ | CH₂CH₂ | H | CH₂CH₂ | bond | phenyl | 3.79[a] |
| I-54 | 3,5-dimethyl-1H-pyrazol-1-yl | CH₂ | O | CH₂CH₂ | CH₂CH₂ | H | CH₂CH₂ | bond | phenyl | 2.86[a] |
| I-55 | 3-(trifluoromethyl)-1H-pyrazol-1-yl | CH₂ | O | CH₂CH₂ | CH₂CH₂ | H | CH₂CH₂ | bond | phenyl | 3.57[b] |
| I-56 | 3-(trifluoromethyl)phenyl | CH₂ | O | CH₂CH₂ | CH₂CH₂ | H | CH₂CH₂ | bond | phenyl | 4.26[b] |
| I-57 | 3-chlorophenyl | CH₂ | O | CH₂CH₂ | CH₂CH₂ | H | CH₂CH₂ | bond | phenyl | 4.1[b] |
| I-58 | CH₃ | CH₂CH₂CH₂ | O | CH₂CH₂ | CH₂CH₂ | H | CH₂CH₂ | bond | phenyl | 3.73[b] |
| I-59 | 3,5-bis(trifluoromethyl)-1H-pyrazol-1-yl | CH₂ | O | CH₂CH₂ | CH₂CH₂ | H | CH₂CH₂ | bond | phenyl | 4.45[b] |
| I-60 | 4-chloro-5-methyl-3-(trifluoromethyl)-1H-pyrazol-1-yl | CH₂ | O | CH₂CH₂ | CH₂CH₂ | H | CH₂CH₂ | bond | phenyl | 4.34[b] |
| I-61 | 2,5-bis(trifluoromethyl)phenyl | bond | O | CH₂CH₂ | CH₂CH₂ | H | CH₂CH₂ | bond | phenyl | 4.67[b] |
| I-62 | 3-(trifluoromethyl)phenyl | bond | O | CH₂CH₂ | CH₂CH₂ | H | CH₂CH₂ | bond | phenyl | 4.23[b] |
| I-63 | thiophen-3-yl | CH₂ | O | CH₂CH₂ | CH₂CH₂ | H | CH₂CH₂ | bond | phenyl | 3.47[b] |
| I-64 | 4-chloro-5-methyl-3-(trifluoromethyl)-1H-pyrazol-1-yl | CHCH₃ | O | CH₂CH₂ | CH₂CH₂ | H | CH₂CH₂ | bond | phenyl | 4.62[b] |
| I-65 | 5-chloro-1-methyl-1H-pyrazol-4-yl | CH₂ | O | CH₂CH₂ | CH₂CH₂ | H | CH₂CH₂ | bond | phenyl | 2.98[b] |
| I-66 | 3,4-dimethoxyphenyl | CH₂CH₂ | O | CH₂CH₂ | CH₂CH₂ | H | CH₂CH₂ | bond | phenyl | 3.43[b] |
| I-67 | 2-chloro-5-(trifluoromethyl)phenyl | CH₂ | O | CH₂CH₂ | CH₂CH₂ | H | CH₂CH₂ | bond | phenyl | 4.73[b] |
| I-68 | 3-(trifluoromethyl)-1H-pyrazol-1-yl | CHCH₃ | O | CH₂CH₂ | CH₂CH₂ | H | CH₂CH₂ | bond | phenyl | 3.93[b] |
| I-69 | 1H-pyrazol-1-yl | CH₂ | O | CH₂CH₂ | CH₂CH₂ | H | CH₂CH₂ | bond | phenyl | 2.56[b] |
| I-70 | 2H-indazol-2-yl | CH₂ | O | CH₂CH₂ | CH₂CH₂ | H | CH₂CH₂ | bond | phenyl | 3.14[b] |
| I-71 | 1,3-benzothiazol-2-yl | CH₂ | O | CH₂CH₂ | CH₂CH₂ | H | CH₂CH₂ | bond | phenyl | 3.68[b] |
| I-72 | 1H-benzimidazol-2-yl | CH₂ | O | CH₂CH₂ | CH₂CH₂ | H | CH₂CH₂ | bond | phenyl | |
| I-73 | 5-methyl-3-(trifluoromethyl)-1H-pyrazol-1-yl | CH₂ | O | CH₂CH₂ | CH₂CH₂ | 2-methylpropyl | CH₂ | bond | H | 3.75[b] |
| I-74 | 3,5-dimethyl-1H-pyrazol-1-yl | CH₂ | O | CH₂CH₂ | CH₂CH₂ | H | C≡C | bond | naphthalen-1-yl | 3.85[c] |
| I-75 | pyridin-4-yl | CH₂ | O | CH₂CH₂ | CH₂CH₂ | H | CH₂CH₂ | bond | phenyl | |
| I-76 | 3,5-dimethyl-1H-pyrazol-1-yl | CH₂ | O | CH₂CH₂ | CH₂CH₂ | H | CH=CH (Z) | bond | naphthalen-1-yl | 3.73[b] |
| I-77 | 3,5-dimethyl-1H-pyrazol-1-yl | CH₂ | O | CH₂CH₂ | CH₂CH₂ | H | CH=CH (E) | bond | naphthalen-1-yl | 3.58[b] |
| I-78 | 5-methyl-3-(trifluoromethyl)-1H-pyrazol-1-yl | CH₂ | O | CH₂CH₂ | CH₂CH₂ | Br | CH₂CH₂ | bond | phenyl | 4.71[b] |
| I-79 | 3,5-dimethyl-1H-pyrazol-1-yl | CH₂ | O | CH₂CH₂ | CH₂CH₂ | H | CH₂CH₂ | bond | naphthalen-1-yl | 3.39[c] |
| I-80 | 5-methyl-3-(trifluoromethyl)-1H-pyrazol-1-yl | CH₂ | O | CH₂CH₂ | CH₂CH₂ | H | CH₂CH₂ | CH₂CHCH₃ | phenyl | 4.77[b] |
| I-81 | 5-methyl-3-(trifluoromethyl)-1H-pyrazol-1-yl | CH₂ | O | CH₂CH₂ | CH₂CH₂ | H | CH₂CH₂ | bond | naphthalen-1-yl | 4.37[b] |
| I-82 | 5-methyl-3-(trifluoromethyl)-1H-pyrazol-1-yl | CH₂ | O | CH₂CH₂ | CH₂CH₂ | H | CH₂CH₂ | bond | pyridin-3-yl | |
| I-83 | 3,5-dimethyl-1H-pyrazol-1-yl | CH₂ | O | CH₂CH₂ | CH₂CH₂ | H | CH₂CH₂ | CH₂CHCH₃ | phenyl | 3.83[b] |
| I-84 | 3,5-dimethyl-1H-pyrazol-1-yl | CH₂ | O | CH₂CH₂ | CH₂CH₂ | H | CH=CH (E) | bond | phenyl | 3.04[b] |
| I-85 | 3,5-dimethyl-1H-pyrazol-1-yl | CH₂ | O | CH₂CH₂ | CH₂CH₂ | H | CH=CH (E) | CH₂CHCH₃ | phenyl | 3.83[c] |

TABLE I-continued $$\underset{\text{where}}{A-L^1}\overset{Y}{\underset{}{\bigvee}}\overset{W}{\underset{X}{\bigvee}}N\overset{N}{\underset{S}{\bigvee}}\overset{L^2-L^3-R^3}{\underset{R^2}{\bigvee}}$$

where

| Ex | A | L¹ | Y | W | X | R² | L² | L³ | R³ | log p |
|---|---|---|---|---|---|---|---|---|---|---|
| I-86 | 5-methyl-3-(trifluoromethyl)-1H-pyrazol-1-yl | CH₂ | O | CH₂CH₂ | CH₂CH₂ | H | C≡C | bond | H | 2.57[b] |
| I-87 | 2,5-dichlorophenyl | CH₂ | O | CH₂CH₂ | CH₂CH₂ | H | CH₂CH₂ | bond | naphthalen-1-yl | |
| I-88 | 2,5-dibromophenyl | CH₂ | O | CH₂CH₂ | CH₂CH₂ | H | CH₂CH₂ | bond | naphthalen-1-yl | |
| I-89 | 5-iodo-2-methylphenyl | CH₂ | O | CH₂CH₂ | CH₂CH₂ | H | CH₂CH₂ | bond | naphthalen-1-yl | |
| I-90 | 3-chloro-5-(trifluoromethyl)pyridin-2-yl | CH₂ | O | CH₂CH₂ | CH₂CH₂ | H | CH₂CH₂ | bond | phenyl | |
| I-91 | 3-chloro-5-(trifluoromethyl)pyridin-2-yl | CH₂ | O | CH₂CH₂ | CH₂CH₂ | H | CH₂CH₂ | bond | naphthalen-1-yl | |
| I-92 | 5-methyl-3-(trifluoromethyl)-1H-pyrazol-1-yl | CH₂ | S | CH₂CH₂ | CH₂CH₂ | H | CH₂CH₂ | bond | naphthalen-1-yl | |
| I-93 | 5-methyl-3-(trifluoromethyl)-1H-pyrazol-1-yl | CH₂ | S | CH₂CH₂ | CH₂CH₂ | H | CH=CH (E) | bond | phenyl | 4.65[b] |
| I-94 | 5-methyl-3-(trifluoromethyl)-1H-pyrazol-1-yl | CH₂ | O | CH₂CH₂ | CH₂CH₂ | H | CH=CH (E) | bond | 3-(trifluoromethyl)phenyl | 4.46[b] |
| I-95 | 1,3-benzodioxol-5-yl | CH₂ | O | CH₂CH₂ | CH₂CH₂ | H | CH₂CH₂ | bond | phenyl | |
| I-96 | 3,5-dimethyl-1H-pyrazol-1-yl | CH₂ | O | CH₂CH₂ | CH₂CH₂ | H | CH=CH (E) | bond | 3-(trifluoromethyl)phenyl | 3.56[b] |
| I-97 | 2,3,6-trifluorophenyl | CH₂ | O | CH₂CH₂ | CH₂CH₂ | H | C≡C | bond | naphthalen-1-yl | 4.71[b] |
| I-98 | 5-methyl-3-(trifluoromethyl)-1H-pyrazol-1-yl | CH₂ | O | CH₂CH₂ | CH₂CH₂ | H | C≡C | bond | trimethylsilyl | 4.28[b] |
| I-99 | 5-methyl-3-(trifluoromethyl)-1H-pyrazol-1-yl | CH₂ | O | CH₂CH₂ | CH₂CH₂ | H | C≡C | bond | phenyl | 3.82[b] |
| I-100 | 5-methyl-3-(trifluoromethyl)-1H-pyrazol-1-yl | CH₂ | O | CH₂CH₂ | CH₂CH₂ | H | C≡C | bond | 4-methoxyphenyl | 3.79[b] |
| I-101 | 5-methyl-3-(trifluoromethyl)-1H-pyrazol-1-yl | CH₂ | O | CH₂CH₂ | CH₂CH₂ | H | C≡C | bond | 2-chlorophenyl | 4.12[b] |
| I-102 | 5-methyl-3-(trifluoromethyl)-1H-pyrazol-1-yl | CH₂ | O | CH₂CH₂ | CH₂CH₂ | H | C≡C | bond | 4-chlorophenyl | 4.37[b] |
| I-103 | 5-methyl-3-(trifluoromethyl)-1H-pyrazol-1-yl | CH₂ | O | CH₂CH₂ | CH₂CH₂ | H | C≡C | bond | 2-methoxyphenyl | 3.67[b] |
| I-104 | 5-methyl-3-(trifluoromethyl)-1H-pyrazol-1-yl | CH₂ | O | CH₂CH₂ | CH₂CH₂ | H | C≡C | bond | 2,4-dimethoxyphenyl | 3.67[b] |
| I-105 | 5-methyl-3-(trifluoromethyl)-1H-pyrazol-1-yl | CH₂ | O | CH₂CH₂ | CH₂CH₂ | H | C≡C | bond | 2,4-dichlorophenyl | 4.72[b] |
| I-106 | 5-methyl-3-(trifluoromethyl)-1H-pyrazol-1-yl | CH₂ | O | CH₂CH₂ | CH₂CH₂ | H | C≡C | bond | 2,5-dimethoxyphenyl | 3.65[b] |
| I-107 | 3,5-diethyl-1H-pyrazol-1-yl | CH₂ | O | CH₂CH₂ | CH₂CH₂ | H | CH₂CH₂ | bond | naphthalen-1-yl | 4.04[b] |
| I-108 | 5-ethyl-3-(trifluoromethyl)-1H-pyrazol-1-yl | CH₂ | O | CH₂CH₂ | CH₂CH₂ | H | CH₂CH₂ | bond | naphthalen-1-yl | 4.65[b] |
| I-109 | 3,5-bis(difluoromethyl)-1H-pyrazol-1-yl | CH₂ | O | CH₂CH₂ | CH₂CH₂ | H | CH₂CH₂ | bond | naphthalen-1-yl | 4.25[b] |
| I-110 | 3-tert-butyl-5-(trifluoromethyl)-1H-pyrazol-1-yl | CH₂ | O | CH₂CH₂ | CH₂CH₂ | H | CH₂CH₂ | bond | naphthalen-1-yl | 5.36[b] |
| I-111 | 5-tert-butyl-3-(trifluoromethyl)-1H-pyrazol-1-yl | CH₂ | O | CH₂CH₂ | CH₂CH₂ | H | CH₂CH₂ | bond | naphthalen-1-yl | 5.14[b] |
| I-112 | 3-tert-butyl-5-(pentafluoroethyl)-1H-pyrazol-1-yl | CH₂ | O | CH₂CH₂ | CH₂CH₂ | H | CH₂CH₂ | bond | naphthalen-1-yl | 5.78[b] |

TABLE I-continued where

| Ex | A | L¹ | Y | W | X | R² | L² | L³ | R³ | log p |
|---|---|---|---|---|---|---|---|---|---|---|
| I-113 | 5-tert-butyl-3-(pentafluoroethyl)-1H-pyrazol-1-yl | $CH_2$ | O | $CH_2CH_2$ | $CH_2CH_2$ | H | $CH_2CH_2$ | bond | naphthalen-1-yl | 5.54[b] |
| I-114 | 3,5-bis(trifluoromethyl)-1H-pyrazol-1-yl | $CH_2$ | O | $CH_2CH_2$ | $CH_2CH_2$ | H | C≡C | bond | naphthalen-1-yl | 5.03[b] |
| I-115 | 3,5-diethyl-1H-pyrazol-1-yl | $CH_2$ | O | $CH_2CH_2$ | $CH_2CH_2$ | H | C≡C | bond | naphthalen-1-yl | 4.2[b] |
| I-116 | 5-ethyl-3-(trifluoromethyl)-1H-pyrazol-1-yl | $CH_2$ | O | $CH_2CH_2$ | $CH_2CH_2$ | H | C≡C | bond | naphthalen-1-yl | 4.8[b] |
| I-117 | 3,5-bis(difluoromethyl)-1H-pyrazol-1-yl | $CH_2$ | O | $CH_2CH_2$ | $CH_2CH_2$ | H | C≡C | bond | naphthalen-1-yl | 4.41[b] |
| I-118 | 3-tert-butyl-5-(trifluoromethyl)-1H-pyrazol-1-yl | $CH_2$ | O | $CH_2CH_2$ | $CH_2CH_2$ | H | C≡C | bond | naphthalen-1-yl | 5.48[b] |
| I-119 | 5-tert-butyl-3-(trifluoromethyl)-1H-pyrazol-1-yl | $CH_2$ | O | $CH_2CH_2$ | $CH_2CH_2$ | H | C≡C | bond | naphthalen-1-yl | 5.14[b] |
| I-120 | 5-tert-butyl-3-(pentafluoroethyl)-1H-pyrazol-1-yl | $CH_2$ | O | $CH_2CH_2$ | $CH_2CH_2$ | H | C≡C | bond | naphthalen-1-yl | 5.59[b] |
| I-121 | 3-(propan-2-yl)-5-(trifluoromethyl)-1H-pyrazol-1-yl | $CH_2$ | O | $CH_2CH_2$ | $CH_2CH_2$ | H | $CH_2CH_2$ | bond | naphthalen-1-yl | 4.89[b] |
| I-122 | 3-(propan-2-yl)-5-(trifluoromethyl)-1H-pyrazol-1-yl | $CH_2$ | O | $CH_2CH_2$ | $CH_2CH_2$ | H | C≡C | bond | naphthalen-1-yl | 4.99[b] |
| I-123 | 5-methyl-3-(trifluoromethyl)-1H-pyrazol-1-yl | $CH_2$ | O | $CH_2CH_2$ | $CH_2CH_2$ | H | $CH_2CH_2$ | bond | 2,4-dichlorophenyl | 4.77[c]; 4.74[b] |
| I-124 | 2,5-dibromophenyl | $CH_2$ | O | $CH_2CH_2$ | $CH_2CH_2$ | H | C≡C | bond | naphthalen-1-yl | 5.52[c]; 5.47[b] |
| I-125 | 2,5-dichlorophenyl | $CH_2$ | O | $CH_2CH_2$ | $CH_2CH_2$ | H | C≡C | bond | H | 3.08[b] |
| I-126 | 5-methyl-3-(trifluoromethyl)-1H-pyrazol-1-yl | $CH_2$ | O | $CH_2CH_2$ | $CH_2CH_2$ | H | $CH_2CH_2$ | bond | 2-methylphenyl | 4.16[c]; 4.08[b] |
| I-127 | 5-methyl-3-(trifluoromethyl)-1H-pyrazol-1-yl | $CH_2$ | O | $CH_2CH_2$ | $CH_2CH_2$ | H | $CH_2CH_2$ | bond | 2-bromophenyl | |
| I-128 | 5-methyl-3-(trifluoromethyl)-1H-pyrazol-1-yl | $CH_2$ | O | $CH_2CH_2$ | $CH_2CH_2$ | H | $CH_2CH_2$ | bond | 2,6-difluorophenyl | 3.97[c], 3.9[b] |
| I-129 | 5-methyl-3-(trifluoromethyl)-1H-pyrazol-1-yl | $CH_2$ | O | $CH_2CH_2$ | $CH_2CH_2$ | H | $CH_2CH_2$ | bond | quinolin-8-yl | |
| I-130 | 5-methyl-3-(trifluoromethyl)-1H-pyrazol-1-yl | $CH_2$ | O | $CH_2CH_2$ | $CH_2CH_2$ | H | $CH_2CH_2$ | bond | 3-methylpyridin-2-yl | |
| I-131 | 5-methyl-3-(trifluoromethyl)-1H-pyrazol-1-yl | $CH_2$ | O | $CH_2CH_2$ | $CH_2CH_2$ | H | $CH_2CH_2$ | bond | 3,5-dimethylisoxazol-4-yl | |
| I-132 | 5-methyl-3-(trifluoromethyl)-1H-pyrazol-1-yl | $CH_2$ | O | $CH_2CH_2$ | $CH_2CH_2$ | H | $CH_2CH_2$ | bond | cyclohexyl | 5.01[b] |
| I-133 | 5-methyl-3-(trifluoromethyl)-1H-pyrazol-1-yl | $CH_2$ | O | $CH_2CH_2$ | $CH_2CH_2$ | H | $CH_2CH_2$ | bond | 1,2,3,4-tetrahydronaphthalen-1-yl | 4.95[b] |
| I-134 | 3,5-bis(trifluoromethyl)-1H-pyrazol-1-yl | $CH_2$ | O | $CH_2CH_2$ | $CH_2CH_2$ | H | $CH_2CH_2$ | bond | 2-methylphenyl | |
| I-135 | 3,5-bis(trifluoromethyl)-1H-pyrazol-1-yl | $CH_2$ | O | $CH_2CH_2$ | $CH_2CH_2$ | H | $CH_2CH_2$ | bond | 2-bromophenyl | |
| I-136 | 3,5-bis(trifluoromethyl)-1H-pyrazol-1-yl | $CH_2$ | O | $CH_2CH_2$ | $CH_2CH_2$ | H | $CH_2CH_2$ | bond | 2,6-difluorophenyl | |

TABLE I-continued

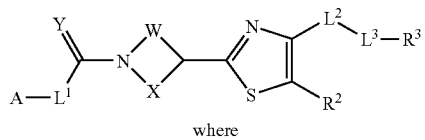

where

| Ex | A | L¹ | Y | W | X | R² | L² | L³ | R³ | log p |
|---|---|---|---|---|---|---|---|---|---|---|
| I-137 | 3,5-bis(trifluoromethyl)-1H-pyrazol-1-yl | $CH_2$ | O | $CH_2CH_2$ | $CH_2CH_2$ | H | $CH_2CH_2$ | bond | quinolin-8-yl | |
| I-138 | 3,5-bis(trifluoromethyl)-1H-pyrazol-1-yl | $CH_2$ | O | $CH_2CH_2$ | $CH_2CH_2$ | H | $CH_2CH_2$ | bond | 3-methylpyridin-2-yl | |
| I-139 | 3,5-bis(trifluoromethyl)-1H-pyrazol-1-yl | $CH_2$ | O | $CH_2CH_2$ | $CH_2CH_2$ | H | $CH_2CH_2$ | bond | 3,5-dimethylisoxazol-4-yl | |
| I-140 | 3,5-bis(trifluoromethyl)-1H-pyrazol-1-yl | $CH_2$ | O | $CH_2CH_2$ | $CH_2CH_2$ | H | $CH_2CH_2$ | bond | cyclohexyl | 5.76[b] |
| I-141 | 3,5-bis(trifluoromethyl)-1H-pyrazol-1-yl | $CH_2$ | O | $CH_2CH_2$ | $CH_2CH_2$ | H | $CH_2CH_2$ | bond | 1,2,3,4-tetrahydronaphthalen-1-yl | |
| I-142 | 3,5-bis(difluoromethyl)-1H-pyrazol-1-yl | $CH_2$ | O | $CH_2CH_2$ | $CH_2CH_2$ | H | $CH_2CH_2$ | bond | 2-methylphenyl | |
| I-143 | 3,5-bis(difluoromethyl)-1H-pyrazol-1-yl | $CH_2$ | O | $CH_2CH_2$ | $CH_2CH_2$ | H | $CH_2CH_2$ | bond | 2-bromophenyl | |
| I-144 | 3,5-bis(difluoromethyl)-1H-pyrazol-1-yl | $CH_2$ | O | $CH_2CH_2$ | $CH_2CH_2$ | H | $CH_2CH_2$ | bond | 2,6-difluorophenyl | |
| I-145 | 3,5-bis(difluoromethyl)-1H-pyrazol-1-yl | $CH_2$ | O | $CH_2CH_2$ | $CH_2CH_2$ | H | $CH_2CH_2$ | bond | quinolin-8-yl | |
| I-146 | 3,5-bis(difluoromethyl)-1H-pyrazol-1-yl | $CH_2$ | O | $CH_2CH_2$ | $CH_2CH_2$ | H | $CH_2CH_2$ | bond | 3-methylpyridin-2-yl | |
| I-147 | 3,5-bis(difluoromethyl)-1H-pyrazol-1-yl | $CH_2$ | O | $CH_2CH_2$ | $CH_2CH_2$ | H | $CH_2CH_2$ | bond | 3,5-dimethylisoxazol-4-yl | |
| I-148 | 3,5-bis(difluoromethyl)-1H-pyrazol-1-yl | $CH_2$ | O | $CH_2CH_2$ | $CH_2CH_2$ | H | $CH_2CH_2$ | bond | cyclohexyl | 4.87[b] |
| I-149 | 3,5-bis(difluoromethyl)-1H-pyrazol-1-yl | $CH_2$ | O | $CH_2CH_2$ | $CH_2CH_2$ | H | $CH_2CH_2$ | bond | 1,2,3,4-tetrahydronaphthalen-1-yl | 4.78[b] |
| I-150 | 2,5-dichlorophenyl | $CH_2$ | O | $CH_2CH_2$ | $CH_2CH_2$ | H | $CH_2CH_2$ | bond | 2-methylphenyl | |
| I-151 | 2,5-dichlorophenyl | $CH_2$ | O | $CH_2CH_2$ | $CH_2CH_2$ | H | $CH_2CH_2$ | bond | 2-bromophenyl | |
| I-152 | 2,5-dichlorophenyl | $CH_2$ | O | $CH_2CH_2$ | $CH_2CH_2$ | H | $CH_2CH_2$ | bond | 2,6-difluorophenyl | |
| I-153 | 2,5-dichlorophenyl | $CH_2$ | O | $CH_2CH_2$ | $CH_2CH_2$ | H | $CH_2CH_2$ | bond | quinolin-8-yl | |
| I-154 | 2,5-dichlorophenyl | $CH_2$ | O | $CH_2CH_2$ | $CH_2CH_2$ | H | $CH_2CH_2$ | bond | 3-methylpyridin-2-yl | |
| I-155 | 2,5-dichlorophenyl | $CH_2$ | O | $CH_2CH_2$ | $CH_2CH_2$ | H | $CH_2CH_2$ | bond | 3,5-dimethylisoxazol-4-yl | |
| I-156 | 2,5-dichlorophenyl | $CH_2$ | O | $CH_2CH_2$ | $CH_2CH_2$ | H | $CH_2CH_2$ | bond | cyclohexyl | |
| I-157 | 2,5-dichlorophenyl | $CH_2$ | O | $CH_2CH_2$ | $CH_2CH_2$ | H | $CH_2CH_2$ | bond | 1,2,3,4-tetrahydronaphthalen-1-yl | |
| I-158 | 2,5-dimethylphenyl | $CH_2$ | O | $CH_2CH_2$ | $CH_2CH_2$ | H | $CH_2CH_2$ | bond | 2-methylphenyl | 4.77[c]; 4.67[b] |
| I-159 | 2,5-dimethylphenyl | $CH_2$ | O | $CH_2CH_2$ | $CH_2CH_2$ | H | $CH_2CH_2$ | bond | 2-bromophenyl | |
| I-160 | 2,5-dimethylphenyl | $CH_2$ | O | $CH_2CH_2$ | $CH_2CH_2$ | H | $CH_2CH_2$ | bond | 2,6-difluorophenyl | 4.55[c]; 4.48[b] |
| I-161 | 2,5-dimethylphenyl | $CH_2$ | O | $CH_2CH_2$ | $CH_2CH_2$ | H | $CH_2CH_2$ | bond | quinolin-8-yl | |
| I-162 | 2,5-dimethylphenyl | $CH_2$ | O | $CH_2CH_2$ | $CH_2CH_2$ | H | $CH_2CH_2$ | bond | 3-methylpyridin-2-yl | |
| I-163 | 2,5-dimethylphenyl | $CH_2$ | O | $CH_2CH_2$ | $CH_2CH_2$ | H | $CH_2CH_2$ | bond | 3,5-dimethylisoxazol-4-yl | |
| I-164 | 2,5-dimethylphenyl | $CH_2$ | O | $CH_2CH_2$ | $CH_2CH_2$ | H | $CH_2CH_2$ | bond | cyclohexyl | |
| I-165 | 2,5-dimethylphenyl | $CH_2$ | O | $CH_2CH_2$ | $CH_2CH_2$ | H | $CH_2CH_2$ | bond | 1,2,3,4-tetrahydronaphthalen-1-yl | |
| I-166 | 5-methyl-3-(trifluoromethyl)-1H-pyrazol-1-yl | $CH_2$ | O | $CH_2CH_2$ | $CH_2CH_2$ | H | CH=CH (mixture of (Z) and (E) isomers) | bond | 2-methylphenyl | 4.23[b] |

TABLE I-continued $$\text{A—L}^1\text{—N(—Y)—W—X—[thiazole with N, S, R}^2\text{]—L}^2\text{—L}^3\text{—R}^3$$

where

| Ex | A | L¹ | Y | W | X | R² | L² | L³ | R³ | log p |
|---|---|---|---|---|---|---|---|---|---|---|
| I-167 | 5-methyl-3-(trifluoromethyl)-1H-pyrazol-1-yl | CH₂ | O | CH₂CH₂ | CH₂CH₂ | H | CH=CH (mixture of (Z) and (E) isomers) | bond | 2-bromophenyl | 4.39 and 4.44[b] |
| I-168 | 5-methyl-3-(trifluoromethyl)-1H-pyrazol-1-yl | CH₂ | O | CH₂CH₂ | CH₂CH₂ | H | CH=CH (mixture of (Z) and (E) isomers) | bond | 2,6-difluorophenyl | 3.90 and 4.21[b] |
| I-169 | 5-methyl-3-(trifluoromethyl)-1H-pyrazol-1-yl | CH₂ | O | CH₂CH₂ | CH₂CH₂ | H | CH=CH (mixture of (Z) and (E) isomers) | bond | quinolin-8-yl | |
| I-170 | 5-methyl-3-(trifluoromethyl)-1H-pyrazol-1-yl | CH₂ | O | CH₂CH₂ | CH₂CH₂ | H | CH=CH (mixture of (Z) and (E) isomers) | bond | 3-methylpyridin-2-yl | |
| I-171 | 5-methyl-3-(trifluoromethyl)-1H-pyrazol-1-yl | CH₂ | O | CH₂CH₂ | CH₂CH₂ | H | CH=CH (mixture of (Z) and (E) isomers) | bond | 3,5-dimethylisoxazol-4-yl | |
| I-172 | 5-methyl-3-(trifluoromethyl)-1H-pyrazol-1-yl | CH₂ | O | CH₂CH₂ | CH₂CH₂ | H | CH=CH (mixture of (Z) and (E) isomers) | bond | cyclohexyl | 4.99 and 5.07[b] |
| I-173 | 5-methyl-3-(trifluoromethyl)-1H-pyrazol-1-yl | CH₂ | O | CH₂CH₂ | CH₂CH₂ | H | CH=CH (mixture of (Z) and (E) isomers) | bond | 1,2,3,4-tetrahydronaphthalen-1-yl | 4.02 and 4.10[b] |
| I-174 | 3,5-bis(trifluoromethyl)-1H-pyrazol-1-yl | CH₂ | O | CH₂CH₂ | CH₂CH₂ | H | CH=CH (mixture of (Z) and (E) isomers) | bond | 2-methylphenyl | 4.93[b] |
| I-175 | 3,5-bis(trifluoromethyl)-1H-pyrazol-1-yl | CH₂ | O | CH₂CH₂ | CH₂CH₂ | H | CH=CH (mixture of (Z) and (E) isomers) | bond | 2-bromophenyl | 4.99[b] |
| I-176 | 3,5-bis(trifluoromethyl)-1H-pyrazol-1-yl | CH₂ | O | CH₂CH₂ | CH₂CH₂ | H | CH=CH (mixture of (Z) and (E) isomers) | bond | 2,6-difluorophenyl | 4.88[b] |
| I-177 | 3,5-bis(trifluoromethyl)-1H-pyrazol-1-yl | CH₂ | O | CH₂CH₂ | CH₂CH₂ | H | CH=CH (mixture of (Z) and (E) isomers) | bond | quinolin-8-yl | |
| I-178 | 3,5-bis(trifluoromethyl)-1H-pyrazol-1-yl | CH₂ | O | CH₂CH₂ | CH₂CH₂ | H | CH=CH (mixture of (Z) and (E) isomers) | bond | 3-methylpyridin-2-yl | |
| I-179 | 3,5-bis(trifluoromethyl)-1H-pyrazol-1-yl | CH₂ | O | CH₂CH₂ | CH₂CH₂ | H | CH=CH (mixture of (Z) and (E) isomers) | bond | 3,5-dimethylisoxazol-4-yl | |
| I-180 | 3,5-bis(trifluoromethyl)-1H-pyrazol-1-yl | CH₂ | O | CH₂CH₂ | CH₂CH₂ | H | CH=CH (mixture of (Z) and (E) isomers) | bond | cyclohexyl | 5.59 and 5.68[b] |
| I-181 | 3,5-bis(trifluoromethyl)-1H-pyrazol-1-yl | CH₂ | O | CH₂CH₂ | CH₂CH₂ | H | CH=CH (mixture of (Z) and (E) isomers) | bond | 1,2,3,4-tetrahydronaphthalen-1-yl | 5.60 and 5.78[b] |
| I-182 | 3,5-bis(difluoromethyl)-1H-pyrazol-1-yl | CH₂ | O | CH₂CH₂ | CH₂CH₂ | H | CH=CH (mixture of (Z) and (E) isomers) | bond | 2-methylphenyl | |
| I-183 | 3,5-bis(difluoromethyl)-1H-pyrazol-1-yl | CH₂ | O | CH₂CH₂ | CH₂CH₂ | H | CH=CH (mixture of (Z) and (E) isomers) | bond | 2-bromophenyl | 4.25 and 4.29[b] |

TABLE I-continued

Structure: A—L¹—C(=Y)—N(W)(X)—[thiazole with R², L²—L³—R³]

| Ex | A | L¹ | Y | W | X | R² | L² | L³ | R³ | log p |
|---|---|---|---|---|---|---|---|---|---|---|
| I-184 | 3,5-bis(difluoromethyl)-1H-pyrazol-1-yl | CH₂ | O | CH₂CH₂ | CH₂CH₂ | H | CH=CH (mixture of (Z) and (E) isomers) | bond | 2,6-difluorophenyl | 3.74 and 4.05[b] |
| I-185 | 3,5-bis(difluoromethyl)-1H-pyrazol-1-yl | CH₂ | O | CH₂CH₂ | CH₂CH₂ | H | CH=CH (mixture of (Z) and (E) isomers) | bond | quinolin-8-yl | |
| I-186 | 3,5-bis(difluoromethyl)-1H-pyrazol-1-yl | CH₂ | O | CH₂CH₂ | CH₂CH₂ | H | CH=CH (mixture of (Z) and (E) isomers) | bond | 3-methylpyridin-2-yl | |
| I-187 | 3,5-bis(difluoromethyl)-1H-pyrazol-1-yl | CH₂ | O | CH₂CH₂ | CH₂CH₂ | H | CH=CH (mixture of (Z) and (E) isomers) | bond | 3,5-dimethylisoxazol-4-yl | |
| I-188 | 3,5-bis(difluoromethyl)-1H-pyrazol-1-yl | CH₂ | O | CH₂CH₂ | CH₂CH₂ | H | CH=CH (mixture of (Z) and (E) isomers) | bond | cyclohexyl | 4.79 and 4.85[b] |
| I-189 | 3,5-bis(difluoromethyl)-1H-pyrazol-1-yl | CH₂ | O | CH₂CH₂ | CH₂CH₂ | H | CH=CH (mixture of (Z) and (E) isomers) | bond | 1,2,3,4-tetrahydronaphthalen-1-yl | 4.81 and 4.97[b] |
| I-190 | 2,5-dichlorophenyl | CH₂ | O | CH₂CH₂ | CH₂CH₂ | H | CH=CH (mixture of (Z) and (E) isomers) | bond | 2-methylphenyl | |
| I-191 | 2,5-dichlorophenyl | CH₂ | O | CH₂CH₂ | CH₂CH₂ | H | CH=CH (mixture of (Z) and (E) isomers) | bond | 2-bromophenyl | |
| I-192 | 2,5-dichlorophenyl | CH₂ | O | CH₂CH₂ | CH₂CH₂ | H | CH=CH (mixture of (Z) and (E) isomers) | bond | 2,6-difluorophenyl | |
| I-193 | 2,5-dichlorophenyl | CH₂ | O | CH₂CH₂ | CH₂CH₂ | H | CH=CH (mixture of (Z) and (E) isomers) | bond | quinolin-8-yl | |
| I-194 | 2,5-dichlorophenyl | CH₂ | O | CH₂CH₂ | CH₂CH₂ | H | CH=CH (mixture of (Z) and (E) isomers) | bond | 3-methylpyridin-2-yl | |
| I-195 | 2,5-dichlorophenyl | CH₂ | O | CH₂CH₂ | CH₂CH₂ | H | CH=CH (mixture of (Z) and (E) isomers) | bond | 3,5-dimethylisoxazol-4-yl | |
| I-196 | 2,5-dichlorophenyl | CH₂ | O | CH₂CH₂ | CH₂CH₂ | H | CH=CH (mixture of (Z) and (E) isomers) | bond | cyclohexyl | |
| I-197 | 2,5-dichlorophenyl | CH₂ | O | CH₂CH₂ | CH₂CH₂ | H | CH=CH (mixture of (Z) and (E) isomers) | bond | 1,2,3,4-tetrahydronaphthalen-1-yl | |
| I-198 | 2,5-dimethylphenyl | CH₂ | O | CH₂CH₂ | CH₂CH₂ | H | CH=CH (mixture of (Z) and (E) isomers) | bond | 2-methylphenyl | |
| I-199 | 2,5-dimethylphenyl | CH₂ | O | CH₂CH₂ | CH₂CH₂ | H | CH=CH (mixture of (Z) and (E) isomers) | bond | 2-bromophenyl | |
| I-200 | 2,5-dimethylphenyl | CH₂ | O | CH₂CH₂ | CH₂CH₂ | H | CH=CH (mixture of (Z) and (E) isomers) | bond | 2,6-difluorophenyl | |

TABLE I-continued

| Ex | A | L¹ | Y | W | X | R² | L² | L³ | R³ | log p |
|---|---|---|---|---|---|---|---|---|---|---|
| I-201 | 2,5-dimethylphenyl | CH₂ | O | CH₂CH₂ | CH₂CH₂ | H | CH=CH (mixture of (Z) and (E) isomers) | bond | quinolin-8-yl | |
| I-202 | 2,5-dimethylphenyl | CH₂ | O | CH₂CH₂ | CH₂CH₂ | H | CH=CH (mixture of (Z) and (E) isomers) | bond | 3-methylpyridin-2-yl | |
| I-203 | 2,5-dimethylphenyl | CH₂ | O | CH₂CH₂ | CH₂CH₂ | H | CH=CH (mixture of (Z) and (E) isomers) | bond | 3,5-dimethylisoxazol-4-yl | |
| I-204 | 2,5-dimethylphenyl | CH₂ | O | CH₂CH₂ | CH₂CH₂ | H | CH=CH (mixture of (Z) and (E) isomers) | bond | cyclohexyl | |
| I-205 | 2,5-dimethylphenyl | CH₂ | O | CH₂CH₂ | CH₂CH₂ | H | CH=CH (mixture of (Z) and (E) isomers) | bond | 1,2,3,4-tetrahydronaphthalen-1-yl | |
| I-206 | 5-methyl-3-(trifluoromethyl)-1H-pyrazol-1-yl | CH₂ | O | CH₂CH₂ | CH₂CH₂ | H | C≡C | bond | 2-methylphenyl | 4.15[c]; 4.15[b] |
| I-207 | 5-methyl-3-(trifluoromethyl)-1H-pyrazol-1-yl | CH₂ | O | CH₂CH₂ | CH₂CH₂ | H | C≡C | bond | 2-bromophenyl | 4.19[c]; 4.16[b] |
| I-208 | 5-methyl-3-(trifluoromethyl)-1H-pyrazol-1-yl | CH₂ | O | CH₂CH₂ | CH₂CH₂ | H | C≡C | bond | 2,6-difluorophenyl | 3.86[c]; 3.83[b] |
| I-209 | 5-methyl-3-(trifluoromethyl)-1H-pyrazol-1-yl | CH₂ | O | CH₂CH₂ | CH₂CH₂ | H | C≡C | bond | quinolin-8-yl | |
| I-210 | 5-methyl-3-(trifluoromethyl)-1H-pyrazol-1-yl | CH₂ | O | CH₂CH₂ | CH₂CH₂ | H | C≡C | bond | 3-methylpyridin-2-yl | 2.95[c]; 2.72[b] |
| I-211 | 5-methyl-3-(trifluoromethyl)-1H-pyrazol-1-yl | CH₂ | O | CH₂CH₂ | CH₂CH₂ | H | C≡C | bond | 3,5-dimethylisoxazol-4-yl | |
| I-212 | 3,5-bis(trifluoromethyl)-1H-pyrazol-1-yl | CH₂ | O | CH₂CH₂ | CH₂CH₂ | H | C≡C | bond | 2-methylphenyl | 4.73[b] |
| I-213 | 3,5-bis(trifluoromethyl)-1H-pyrazol-1-yl | CH₂ | O | CH₂CH₂ | CH₂CH₂ | H | C≡C | bond | 2-bromophenyl | 4.74[b] |
| I-214 | 3,5-bis(trifluoromethyl)-1H-pyrazol-1-yl | CH₂ | O | CH₂CH₂ | CH₂CH₂ | H | C≡C | bond | 2,6-difluorophenyl | 4.4[b] |
| I-215 | 3,5-bis(trifluoromethyl)-1H-pyrazol-1-yl | CH₂ | O | CH₂CH₂ | CH₂CH₂ | H | C≡C | bond | quinolin-8-yl | |
| I-216 | 3,5-bis(trifluoromethyl)-1H-pyrazol-1-yl | CH₂ | O | CH₂CH₂ | CH₂CH₂ | H | C≡C | bond | 3-methylpyridin-2-yl | 3.37[b] |
| I-217 | 3,5-bis(trifluoromethyl)-1H-pyrazol-1-yl | CH₂ | O | CH₂CH₂ | CH₂CH₂ | H | C≡C | bond | 3,5-dimethylisoxazol-4-yl | |
| I-218 | 3,5-bis(difluoromethyl)-1H-pyrazol-1-yl | CH₂ | O | CH₂CH₂ | CH₂CH₂ | H | C≡C | bond | 2-methylphenyl | 4.02[c]; 3.99[b] |
| I-219 | 3,5-bis(difluoromethyl)-1H-pyrazol-1-yl | CH₂ | O | CH₂CH₂ | CH₂CH₂ | H | C≡C | bond | 2-bromophenyl | 4.04[c]; 4.04[b] |
| I-220 | 3,5-bis(difluoromethyl)-1H-pyrazol-1-yl | CH₂ | O | CH₂CH₂ | CH₂CH₂ | H | C≡C | bond | 2,6-difluorophenyl | 3.73[c]; 3.7[b] |
| I-221 | 3,5-bis(difluoromethyl)-1H-pyrazol-1-yl | CH₂ | O | CH₂CH₂ | CH₂CH₂ | H | C≡C | bond | quinolin-8-yl | |

TABLE I-continued where

| Ex | A | $L^1$ | Y | W | X | $R^2$ | $L^2$ | $L^3$ | $R^3$ | log p |
|---|---|---|---|---|---|---|---|---|---|---|
| I-222 | 3,5-bis(difluoromethyl)-1H-pyrazol-1-yl | $CH_2$ | O | $CH_2CH_2$ | $CH_2CH_2$ | H | C≡C | bond | 3-methylpyridin-2-yl | 2.86[c]; 2.68[b] |
| I-223 | 3,5-bis(difluoromethyl)-1H-pyrazol-1-yl | $CH_2$ | O | $CH_2CH_2$ | $CH_2CH_2$ | H | C≡C | bond | 3,5-dimethylisoxazol-4-yl | 3.09[b] |
| I-224 | 2,5-dichlorophenyl | $CH_2$ | O | $CH_2CH_2$ | $CH_2CH_2$ | H | C≡C | bond | 2-methylphenyl | 4.91[b] |
| I-225 | 2,5-dichlorophenyl | $CH_2$ | O | $CH_2CH_2$ | $CH_2CH_2$ | H | C≡C | bond | 2-bromophenyl | 4.91[b] |
| I-226 | 2,5-dichlorophenyl | $CH_2$ | O | $CH_2CH_2$ | $CH_2CH_2$ | H | C≡C | bond | 2,6-difluorophenyl | 4.52[b] |
| I-227 | 2,5-dichlorophenyl | $CH_2$ | O | $CH_2CH_2$ | $CH_2CH_2$ | H | C≡C | bond | quinolin-8-yl | |
| I-228 | 2,5-dichlorophenyl | $CH_2$ | O | $CH_2CH_2$ | $CH_2CH_2$ | H | C≡C | bond | 3-methylpyridin-2-yl | 3.55[c] 3.35[b] |
| I-229 | 2,5-dichlorophenyl | $CH_2$ | O | $CH_2CH_2$ | $CH_2CH_2$ | H | C≡C | bond | 3,5-dimethylisoxazol-4-yl | 3.86[b] |
| I-230 | 2,5-dimethylphenyl | $CH_2$ | O | $CH_2CH_2$ | $CH_2CH_2$ | H | C≡C | bond | 2-methylphenyl | 4.78[c]; 4.75[b] |
| I-231 | 2,5-dimethylphenyl | $CH_2$ | O | $CH_2CH_2$ | $CH_2CH_2$ | H | C≡C | bond | 2-bromophenyl | 4.8[c]; 4.77[b] |
| I-232 | 2,5-dimethylphenyl | $CH_2$ | O | $CH_2CH_2$ | $CH_2CH_2$ | H | C≡C | bond | 2,6-difluorophenyl | 4.39[c]; 4.36[b] |
| I-233 | 2,5-dimethylphenyl | $CH_2$ | O | $CH_2CH_2$ | $CH_2CH_2$ | H | C≡C | bond | quinolin-8-yl | |
| I-234 | 2,5-dimethylphenyl | $CH_2$ | O | $CH_2CH_2$ | $CH_2CH_2$ | H | C≡C | bond | 3-methylpyridin-2-yl | |
| I-235 | 2,5-dimethylphenyl | $CH_2$ | O | $CH_2CH_2$ | $CH_2CH_2$ | H | C≡C | bond | 3,5-dimethylisoxazol-4-yl | 3.71[c]; 3.67[b] |
| I-236 | 3,5-bis(trifluoromethyl)-1H-pyrazol-1-yl | $CH_2$ | O | $CH_2CH_2$ | $CH_2CH_2$ | H | CH=CH (Z) | bond | 3-methylpyridin-2-yl | 2.46[b] |
| I-237 | 2,5-dimethylphenyl | $CH_2$ | O | $CH_2CH_2$ | $CH_2CH_2$ | H | CH=CH (Z) | bond | 2-methylphenyl | 4.95[c]; 4.86[b] |
| I-238 | 2,5-dimethylphenyl | $CH_2$ | O | $CH_2CH_2$ | $CH_2CH_2$ | H | C≡C | bond | H | 2.93[b]; 2.95[c] |
| I-239 | 3,5-bis(difluoromethyl)-1H-pyrazol-1-yl | $CH_2$ | O | $CH_2CH_2$ | $CH_2CH_2$ | H | C≡C | bond | H | 2.45[b] |
| I-240 | 3,5-bis(trifluoromethyl)-1H-pyrazol-1-yl | $CH_2$ | O | $CH_2CH_2$ | $CH_2CH_2$ | H | CH=CH (mixture of (Z) and (E) isomers) | bond | 2-chloro-6-fluorophenyl | 4.85 and 5.09[b] |
| I-241 | 3,5-bis(difluoromethyl)-1H-pyrazol-1-yl | $CH_2$ | O | $CH_2CH_2$ | $CH_2CH_2$ | H | CH=CH (mixture of (Z) and (E) isomers) | bond | 2-chloro-6-fluorophenyl | 4.09 and 4.33[b] |
| I-242 | 5-methyl-3-(trifluoromethyl)-1H-pyrazol-1-yl | $CH_2$ | O | $CH_2CH_2$ | $CH_2CH_2$ | H | CH=CH (mixture of (Z) and (E) isomers) | bond | 2-chloro-6-fluorophenyl | 4.48[b] |

The logP values were determined in accordance with EEC Directive 79/831 Annex V.A8 by HPLC (High Performance Liquid Chromatography) on reversed-phase columns (C 18), using the methods below:

[a] The determination was carried out in the acidic range at pH 2.3 using the mobile phases 0.1% aqueous phosphoric acid and acetonitrile; linear gradient from 10% acetonitrile to 95% acetonitrile.

[b] The LC-MS determination in the acidic range was carried out at pH 2.7 using the mobile phases 0.1% aqueous formic acid and acetonitrile (contains 0.1% formic acid): linear gradient from 10% acetonitrile to 95% acetonitrile.

[c] The LC-MS determination in the neutral range was carried out at pH 7.8 using the mobile phases 0.001 molar aqueous ammonium bicarbonate solution and acetonitrile; linear gradient from 10% acetonitrile to 95% acetonitrile.

Calibration was carried out using unbranched alkan-2-ones (having 3 to 16 carbon atoms), with known logP values (determination of the logP values by the retention times using linear interpolation between two successive alkanones).

The lambda-max values were determined in the maxima of the chromatographic signals using the UV spectra from 200 nm to 400 nm.

NMR Data of Selected Examples

| Ex | NMR Data |
|---|---|
| I-1 | $^1$HNMR δ = 7.46 (m, 2H), 7.31-7.18 (m, 4H), 6.62 (d, 1H), 6.57 (d, 1H), 6.44 (s, 1H), 5.19 (bs, 2H), 4.20 (bs, 1H), 3.90 (bs, 1H), 3.26 (m, 2H), 2.90 (m, 1H), 2.21 (s, 3H), 2.05 (m, 2H), 1.80-1.50 (m, 2H) ppm |
| I-2 | $^1$HNMR δ = 7.95-7.92 (m, 2H), 7.87-7.84 (m, 1H), 7.52-7.43 (m, 4H), 7.11 (d, 1H), 6.93 (d, 1H), 6.88 (s, 1H), 6.45 (s, 1H), 5.14 (s, 2H), 4.05 (bs, 1H), 3.74 (bs, 1H), 3.20-3.05 (m, 2H), 2.88 (bs, 1H), 2.24 (s, 3H), 1.90-1.78 (bs, 2H), 1.50 (bs, 1H), 1.35 (bs, 1H) ppm |

| Ex | NMR Data |
|---|---|
| I-3 | $^1$HNMR δ = 7.32 (s, 1H), 7.29-7.22 (m, 4H), 7.15 (m, 1H), 6.44 (s, 1H), 6.35 (d, 1H), 5.60 (m, 1H), 5.20 (bs, 2H), 4.30 (bs, 1H), 3.98 (bs, 1H), 3.38-3.25 (m, 2H), 3.05-2.84 (m, 4H), 2.22 (s, 3H), 2.17-2.05 (m, 2H), 1.85-1.56 (m, 2H), 1.26 (d, 3H) ppm |
| I-26 | $^1$HNMR δ = 7.56 (d, 2H), 7.50 (s, 1H), 7.39-7.34 (m, 3H), 7.28-7.18 (m, 2H), 6.45 (s, 1H), 5.23 (bs, 2H), 4.37 (bs, 1H), 4.01 (bs, 1H), 3.35 (m, 1H), 3.32 (bs, 1H), 2.90 (bs, 1H), 2.23 (s, 3H), 2.18-2.10 (m, 2H), 1.80 (bs, 1H), 1.63 (bs, 1H) ppm |
| I-27 | $^1$HNMR δ = 8.23 (d, 1H), 8.16 (d, 1H), 7.95 (d, 1H), 7.88 (d, 1H), 7.83 (d, 1H), 7.64 (s, 1H), 7.63-7.51 (m, 3H), 7.27 (d, 1H), 6.46 (s, 1H), 5.24 (bs, 2H), 4.38 (bs, 1H), 4.03 (bs, 1H), 3.40 (m, 1H), 3.32 (bs, 1H), 2.94 (bs, 1H), 2.24 (s, 3H), 2.23-2.12 (m, 2H), 1.85 (bs, 1H), 1.70 (bs, 1H) ppm |
| I-50 | $^1$HNMR (CD$_3$CN) δ = 8.39 (d, 1H), 7.96 (d, 2H), 7.80 (d, 1H), 7.72 (s, 1H), 7.67-7.50 (m, 3H), 6.37 (s, 1H), 5.05 (s, 2H), 4.45 (bs, 1H), 3.98 (bs, 1H), 3.40-3.20 (m, 2H), 2.93 (bs, 1H), 2.25 (s, 3H), 2.25-2.15 (m, 2H), 1.90-1.75 (m, 2H) ppm |
| I-51 | $^1$HNMR (CD$_3$CN) δ = 8.74 (dd, 1H), 8.59 (dd, 1H), 7.99 (s, 1H), 7.96 (m, 1H), 7.45 (dd, 1H), 6.45 (s, 1H), 5.22 (bs, 2H), 4.35 (bs, 1H), 4.00 (bs, 1H), 3.40-3.20 (m, 3H), 2.22 (s, 3H), 2.17-2.10 (m, 2H), 1.90-1.55 (m, 2H) ppm |
| I-52 | $^1$HNMR (CD$_3$CN) δ = 7.46 (s, 1H), 7.42-7.34 (m, 4H), 7.30-7.25 (m, 1H), 6.39 (s, 1H), 5.09 (d, 1H), 5.02 (d, 1H), 4.45 (d, 1H), 3.91 (d, 1H), 3.84 (s, 2H), 3.25 (m, 2H), 2.82 (t, 1H), 2.23 (s, 3H), 2.18-2.05 (m, 2H), 1.82 (qd, 1H), 1.66 (qd, 1H) ppm |
| I-53 | $^1$HNMR δ = 7.28-7.26 (m, 2H), 7.22-7.21 (m, 2H), 7.19-7.15 (m, 2H), 6.51 (s, 1H), 5.33 (d, 1H), 5.25 (d, 1H), 4.36 (d, 1H), 3.95 (d, 1H), 3.35-3.20 (m, 2H), 2.96 (s, 4H), 2.82 (t, 1H), 2.21 (s, 3H), 2.09 (d, 1H), 2.07 (d, 1H), 1.78 (m, 1H), 1.53 (m, 1H) ppm |
| I-54 | $^1$HNMR δ = 7.26-7.13 (m, 5H), 7.06 (s, 1H), 5.77 (s, 1H), 4.91 (bs, 2H), 4.28 (m, 1H), 4.03 (m, 1H), 3.25 (m, 1H), 3.16 (m, 1H), 2.97 (m, 4H), 2.85 (m, 1H), 2.11 (s, 3H), 2.10-1.97 (m + s, 5H), 1.61 (m, 2H) ppm |
| I-55 | $^1$HNMR δ = 7.85 (d, 1H), 7.26-7.13 (m, 5H), 7.06 (s, 1H), 6.66 (d, 1H), 5.27 (bs, 2H), 4.30 (bs, 1H), 3.95 (bs, 1H), 3.26 (m, 1H), 3.20-2.80 (m + s, 6H), 2.07 (m, 2H), 1.80-1.50 (m, 2H) ppm |
| I-57 | $^1$HNMR δ = 7.34-7.12 (m, 9H), 7.04 (s, 1H), 4.38 (bs, 1H), 4.00 (bs, 1H), 3.75 (s, 2H), 3.27-2.98 (m, 2H), 2.96 (m, 4H), 2.80 (bs, 1H), 2.02 (m, 2H), 1.51 (m, 2H) ppm |
| I-58 | $^1$HNMR δ = 7.27-7.21 (m, 2H), 7.20-7.14 (m, 3H), 7.05 (s, 1H), 4.37 (bs, 1H), 3.95 (bs, 1H), 3.26-3.18 (m, 2H), 2.96 (s, 4H), 2.80 (bs, 1H), 2.33 (t, 2H), 2.04 (d, 2H), 1.55 (bs, 2H), 1.50 (tt, 2H), 1.33 (tq, 2H), 0.90 (t, 3H) ppm |
| I-59 | $^1$HNMR δ = 7.47 (s, 1H), 7.26-7.13 (m, 5H), 7.07 (s, 1H), 5.46 (m, 2H), 4.27 (bs, 1H), 3.93 (bs, 1H), 3.30 (m, 1H), 3.20-2.85 (m + s, 6H), 2.05 (m, 2H), 1.79 (bs, 1H), 1.57 (bs, 1H) ppm |
| I-60 | $^1$HNMR δ = 7.26-7.13 (m, 5H), 7.07 (s, 1H), 5.29 (bs, 2H), 4.30 (bs, 1H), 3.92 (bs, 1H), 3.28 (m, 1H), 3.20 (m, 1H), 3.00-2.80 (m, 5H), 2.20 (s, 3H), 2.07 (m, 2H), 1.80 (bs, 1H), 1.60 (bs, 1H) ppm |
| I-61 | $^1$HNMR δ = 8.07-7.90 (m, 3H), 7.26-7.21 (m, 2H), 7.20-7.14 (m, 3H), 7.08 (s, 1H), 4.50 (d, 1H), 3.35-3.23 (m, 4H), 2.97 (s, 4H), 2.22-2.10 (m, 1H), 2.00-1.87 (m, 2H), 1.87-1.45 (m, 2H) ppm |
| I-63 | $^1$HNMR δ = 7.44-7.43 (m, 1H), 7.28-7.12 (m, 6H), 7.05 (s, 1H), 6.99 (d, 1H), 4.38 (bs, 1H), 3.99 (bs, 1H), 3.72 (s, 2H), 3.22-3.15 (m, 2H), 2.96 (s, 4H), 2.81 (bs, 1H), 2.00 (d, 2H), 1.52 (m, 2H) ppm |
| I-64 | $^1$HNMR δ = 7.26-7.21 (m, 2H), 7.20-7.13 (m, 3H), 7.06 (s, 1H), 5.70 (m, 1H), 4.30 (bs, 1H), 4.00 (bs, 1H), 3.30-3.19 (m, 2H), 2.96 (s, 5H), 2.26 (d, 3H), 2.08-1.96 (m, 2H), 1.64-1.54 (m, 5H) ppm |
| I-65 | $^1$HNMR δ = 7.40 (s, 1H), 7.26-7.15 (m, 5H), 7.06 (s, 1H), 4.35 (bs, 1H), 4.05 (bs, 1H), 3.76 (s, 3H), 3.49 (s, 2H), 3.30-3.19 (m, 2H), 2.99 (s, 4H), 2.82 (bs, 1H), 2.08-2.00 (m, 2H), 1.58 (bs, 1H) ppm |
| I-66 | $^1$HNMR δ = 7.26-7.21 (m, 2H), 7.20-7.12 (m, 3H), 7.05 (s, 1H), 6.85-6.80 (m, 3H), 6.75-6.71 (dd, 1H), 3.93 (bs, 1H), 3.74 (s, 3H), 3.69 (s, 3H), 3.20 (m, 1H), 2.96 (s, 4H), 2.80-2.74 (m, 2H), 2.65-2.55 (bs, 2H), 2.04-1.97 (m, 2H), 1.58-1.42 (m, 2H), 1.28 (t, 2H) ppm |
| I-67 | $^1$HNMR δ = 7.71-7.58 (m, 3H), 7.27-7.12 (m, 5H), 7.07 (s, 1H), 4.37 (bs, 1H), 4.05 (bs, 1H), 3.97 (s, 2H), 3.35-3.23 (m, 2H), 2.97 (s, 4H), 2.88 (bs, 1H), 2.07 (d, 2H), 1.65 (bs, 2H) ppm |
| I-68 | $^1$HNMR δ = 7.99 (d, 1H), 7.26-7.12 (m, 5H), 7.05 (s, 1H), 6.69 (d, 1H), 5.74 (q, 1H), 4.40-3.95 (m, 2H), 3.24 (m, 1H), 3.20-2.75 (m + s, 6H), 2.05 (m, 2H), 1.30-1.70 (m + d, 5H) ppm |
| I-70 | $^1$HNMR (CD$_3$CN) δ = 8.10 (s, 1H), 7.71 (d, 1H), 7.60 (d, 1H), 7.29-7.15 (m, 6H), 7.07 (dd, 1H), 6.87 (s, 1H), 5.45 (d, 1H), 5.36 (d, 1H), 4.48 (bs, 1H), 4.00 (d, 1H), 3.35-3.23 (m, 2H), 3.00 (s, 4H), 2.86 (t, 1H), 2.18-2.06 (m, 2H), 1.80 (qd, 1H), 1.66 (qd, 1H) ppm |
| I-71 | $^1$HNMR δ = 8.03 (d, 1H), 7.93 (d, 1H), 7.47 (t, 1H), 7.40 (t, 1H), 7.25-7.16 (m, 5H), 7.06 (s, 1H), 4.40 (bs, 1H), 4.34 (s, 2H), 4.09 (bs, 1H), 3.40-3.15 (m, 3H), 2.96 (s, 4H), 2.08-2.02 (m, 2H), 1.65 (bs, 2H) ppm |
| I-74 | $^1$HNMR δ = 8.31 (d, 1H), 8.02 (d, 2H), 7.82 (d, 1H), 7.69 (t, 1H), 7.63-7.51 (m, 3H), 5.79 (s, 1H), 4.95 (s, 2H), 3.41-3.32 (m, 2H), 2.19-2.09 (m, 3H), 2.12 (s, 3H), 2.07 (s, 3H), 1.81-1.53 (m, 4H) ppm |
| I-76 | $^1$HNMR δ = 8.21 (d, 1H), 8.13 (d, 1H), 7.95 (d, 1H), 7.89 (d, 1H), 7.84 (d, 1H), 7.62-7.51 (m, 4H), 7.28 (d, 1H), 5.79 (s, 1H), 4.92 (s, 1H), 3.42-3.31 (m, 2H), 2.21-2.09 (m, 3H), 2.12 (s, 3H), 2.07 (s, 3H), 1.85-1.59 (m, 4H) ppm |
| I-77 | $^1$HNMR δ = 7.29 (dd, 2H), 7.85 (dd, 1H), 7.55-7.41 (m, 4H), 7.11 (d, 1H), 6.90 (t, 2H), 5.79 (s, 1H), 4.86 (bs, 2H), 3.10 (m, 1H), 2.51 (m, 2H), 2.11 (s, 3H), 2.06 (s, 3H), 2.88-2.72 (m, 2H), 1.49-1.31 (m, 4H) ppm |
| I-78 | $^1$HNMR δ = 7.27-7.22 (m, 2H), 7.18-7.13 (m, 3H), 6.45 (s, 1H), 5.22 (bs, 2H), 4.38 (bs, 1H), 3.95 (bs, 1H), 3.33-3.20 (m, 2H), 2.94 (s, 4H), 2.93 (bs, 1H), 2.22 (s, 3H), 2.09-2.02 (m, 2H), 1.80-1.50 (m, 2H) ppm |

| Ex | NMR Data |
|---|---|
| I-79 | $^1$HNMR δ = 8.09 (d, 1H), 7.89 (d, 1H), 7.76 (d, 1H), 7.56-7.43 (m, 2H), 7.41-7.32 (m, 2H), 7.11 (s, 1H), 5.78 (s, 1H), 4.92 (s, 2H), 3.47-3.41 (m, 4H), 3.46-3.22 (m, 3H), 2.12 (s, 3H), 2.09-2.02 (m, 2H), 2.06 (s, 3H), 1.77-1.49 (m, 4H) ppm |
| I-80 | $^1$HNMR δ = 7.28-7.23 (m, 2H), 7.19-7.14 (m, 3H), 7.02 (s, 1H), 6.44 (s, 1H), 5.20 (bs, 2H), 4.30 (bs, 1H), 3.95 (bs, 1H), 3.30-3.20 (m, 2H), 2.87 (bs, 1H), 2.72 (m, 1H), 2.67-2.62 (m, 2H), 2.22 (s, 3H), 2.07-2.02 (m, 2H), 1.72 (bs, 1H), 1.63-1.47 (m, 5H), 1.19 (d, 3H) ppm |
| I-81 | $^1$HNMR δ = 8.09 (d, 1H), 7.90 (d, 1H), 7.75 (d, 1H), 7.56-7.46 (m, 2H), 7.42-7.33 (m, 2H), 7.12 (s, 1H), 6.45 (s, 1H), 5.22 (bs, 2H), 4.31 (bs, 1H), 3.98 (bs, 1H), 3.44 (t, 2H), 3.35-3.26 (m, 2H), 3.15-3.05 (m, 2H), 2.90 (bs, 1H), 2.23 (s, 3H), 2.15-2.05 (m, 2H), 1.75 (bs, 1H), 1.62 (bs, 1H) ppm |
| I-83 | $^1$HNMR δ = 7.32-7.21 (m, 2H), 7.19-7.11 (m, 4H), 7.02 (s, 1H), 5.75 (s, 1H), 4.87 (s, 1H), 3.26-3.12 (m, 2H), 2.72-2.68 (m, 2H), 2.67-2.59 (m, 4H), 2.11 (s, 3H), 2.05 (s, 3H), 2.02-1.91 (m, 4H), 1.61-1.42 (m, 4H), 1.19 (d, 3H) ppm |
| I-84 | $^1$HNMR δ = 7.56 (d, 2H), 7.50 (s, 1H), 7.37 (d, 2H), 7.34 (s, 1H), 7.30-7.16 (m, 2H), 5.79 (s, 1H), 4.93 (s, 2H), 3.41-3.26 (m, 2H), 2.93-2.76 (m, 1H), 2.12 (s, 3H), 2.04 (s, 3H), 2.11-2.03 (m, 2H), 1.78-1.54 (m, 4H) ppm |
| I-85 | $^1$HNMR δ = 7.31-7.21 (m, 5H), 7.19-7.12 (m, 1H), 6.33 (d, 1H), 5.79 (s, 1H), 5.62-5.52 (m, 1H), 4.92 (s, 2H), 4.38-4.12 (m, 1H), 4.12-3.92 (m, 1H), 3.33-3.22 (m, 2H), 2.96-2.81 (m, 4H), 2.10 (s, 3H), 2.03 (s, 3H), 1.72-1.53 (m, 2H), 1.21 (d, 3H) ppm |
| I-86 | $^1$HNMR δ = 7.86 (s, 1H), 6.44 (s, 1H), 5.20 (bs, 2H), 4.31 (bs, 1H), 4.08 (s, 1H), 3.98 (bs, 1H), 3.31 (m, 1H), 3.28 (bs, 1H), 2.88 (bs, 1H), 2.22 (s, 3H), 2.13-2.05 (m, 2H), 1.78 (bs, 1H), 1.61 (bs, 1H) ppm |
| I-93 | $^1$HNMR (CD$_3$CN) δ = 7.55 (d, 2H), 7.43 (d, 1H), 7.37 (t, 2H), 7.30-7.28 (m, 2H), 7.18 (d, 1H), 6.39 (s, 1H), 5.41 (d, 1H), 5.26 (s, 2H), 4.42 (d, 1H), 3.54 (t, 1H), 3.45 (m, 1H), 3.38 (t, 1H), 2.31 (s, 3H), 2.30-2.23 (m, 2H), 1.95-1.80 (m, 2H) ppm |
| I-94 | $^1$HNMR δ = 7.91 (s, 1H), 7.72 (d, 1H), 7.61-7.49 (m, 2H), 7.47 (s, 1H), 6.65 (s, 1H), 6.44 (s, 1H), 5.12 (s, 1H), 3.29-3.18 (m, 2H), 2.89-2.74 (m, 1H), 2.23-2.17 (m, 2H), 2.20 (s, 3H), 2.01 (d, 2H), 1.72-1.61 (m, 2H), 1.61-1.49 (m, 2H) ppm |
| I-96 | $^1$HNMR δ = 7.92 (s, 1H), 7.72 (d, 1H), 7.61-7.51 (m, 2H), 7.45 (s, 1H), 6.64 (s, 1H), 5.78 (s, 1H), 4.85 (s, 1H), 3.28-3.12 (m, 2H), 3.11-3.05 (m, 1H), 2.12-2.09 (m, 2H), 2.10 (s, 3H), 2.05 (s, 3H), 1.98 (d, 2H), 1.63-1.48 (m, 4H) ppm |
| I-97 | $^1$HNMR δ = 8.34 (d, 1H), 8.08 (s, 1H), 8.01 (d, 2H), 7.83 (dd, 1H), 7.68 (m, 1H), 7.62 (m, 1H), 7.57 (dd, 1H), 7.37 (m, 1H), 7.07 (m, 1H), 4.37 (bs, 1H), 4.15 (bs, 1H), 3.86 (bs, 2H), 3.40 (m, 1H), 3.34 (bs, 1H), 2.88 (bs, 1H), 2.16 (bs, 2H), 1.78 (bs, 1H), 1.64 (bs, 1H) ppm |
| I-98 | $^1$HNMR δ = 7.70 (s, 1H), 6.27 (s, 1H), 5.08 (d, 1H), 5.01 (d, 1H), 4.12 (bd, 1H), 3.76 (bd, 1H), 3.05 (t, 1H), 2.59 (t, 1H), 1.97 (s, 3H), 1.88-1.77 (m, 2H), 1.56 (tdd, 1H), 1.30 (tdd, 1H), 0.00 (s, 9H) ppm |
| I-99 | $^1$HNMR δ = 7.92 (s, 1H), 7.57-7.54 (m, 2H), 7.45-7.41 (m, 3H), 6.45 (s, 1H), 5.23 (bs, 2H), 4.33 (bs, 1H), 3.98 (bs, 1H), 3.36 (m, 1H), 3.28 (bs, 1H), 2.89 (bs, 1H), 2.23 (s, 3H), 2.16-2.08 (m, 2H), 1.80 (bs, 1H), 1.63 (bs, 1H) ppm |
| I-100 | $^1$HNMR δ = 7.84 (s, 1H), 7.49 (d, 2H), 6.98 (d, 2H), 6.45 (s, 1H), 5.22 (bs, 2H), 4.33 (bs, 1H), 3.98 (bs, 1H), 3.80 (s, 3H), 3.34 (m, 1H), 3.28 (bs, 1H), 2.89 (bs, 1H), 2.22 (s, 3H), 2.15-2.09 (m, 2H), 1.80 (bs, 1H), 1.63 (bs, 1H) ppm |
| I-101 | $^1$HNMR δ = 7.99 (s, 1H), 7.67 (dd, 1H), 7.56 (dd, 1H), 7.45 (td, 1H), 7.39 (td, 1H), 6.45 (s, 1H), 5.23 (bs, 2H), 4.33 (bs, 1H), 3.98 (bs, 1H), 3.37 (m, 1H), 3.28 (bs, 1H), 2.89 (bs, 1H), 2.23 (s, 3H), 2.15-2.09 (m, 2H), 1.80 (bs, 1H), 1.63 (bs, 1H) ppm |
| I-102 | $^1$HNMR δ = 7.95 (s, 1H), 7.60-7.55 (m, 2H), 7.52-7.46 (m, 2H), 6.45 (s, 1H), 5.22 (bs, 2H), 4.33 (bs, 1H), 3.98 (bs, 1H), 3.35 (m, 1H), 3.28 (bs, 1H), 2.89 (bs, 1H), 2.22 (s, 3H), 2.15-2.08 (m, 2H), 1.80 (bs, 1H), 1.63 (bs, 1H) ppm |
| I-103 | $^1$HNMR δ = 7.86 (s, 1H), 7.47 (dd, 1H), 7.40 (td, 1H), 7.09 (d, 1H), 6.98 (td, 1H), 6.45 (s, 1H), 5.23 (bs, 2H), 4.33 (bs, 1H), 3.98 (bs, 1H), 3.86 (s, 3H), 3.35 (m, 1H), 3.29 (bs, 1H), 2.89 (bs, 1H), 2.23 (s, 3H), 2.15-2.08 (m, 2H), 1.80 (bs, 1H), 1.63 (bs, 1H) ppm |
| I-104 | $^1$HNMR δ = 7.81 (s, 1H), 7.38 (d, 1H), 6.63 (d, 1H), 6.56 (dd, 1H), 6.45 (s, 1H), 5.22 (bs, 2H), 4.33 (bs, 1H), 3.98 (bs, 1H), 3.85 (s, 3H), 3.81 (s, 3H), 3.34 (m, 1H), 3.29 (bs, 1H), 2.89 (bs, 1H), 2.22 (s, 3H), 2.15-2.07 (m, 2H), 1.80 (bs, 1H), 1.64 (bs, 1H) ppm |
| I-105 | $^1$HNMR (CD$_3$CN) δ = 7.67 (s, 1H), 7.58 (d, 1H), 7.57 (d, 1H), 7.38 (dd, 1H), 6.37 (s, 1H), 5.04 (bs, 2H), 4.46 (bs, 1H), 3.95 (bs, 1H), 3.33 (m, 1H), 3.29 (bs, 1H), 2.90 (bs, 1H), 2.24 (s, 3H), 2.20-2.13 (m, 2H), 1.90-1.66 (m, 2H) ppm |
| I-106 | $^1$HNMR δ = 7.87 (s, 1H), 7.04-6.95 (m, 3H), 6.45 (s, 1H), 5.22 (bs, 2H), 4.33 (bs, 1H), 3.98 (bs, 1H), 3.81 (s, 3H), 3.74 (s, 3H), 3.34 (m, 1H), 3.29 (bs, 1H), 2.89 (bs, 1H), 2.23 (s, 3H), 2.15-2.08 (m, 2H), 1.80 (bs, 1H), 1.63 (bs, 1H) ppm |
| I-123 | $^1$HNMR (CD$_3$CN) δ = 7.44 (d, 1H), 7.22 (dd, 1H), 7.18 (d, 1H), 6.88 (s, 1H), 6.40 (s, 1H), 5.11 (d, 1H), 5.04 (d, 1H), 4.45 (bd, 1H), 3.91 (bd, 1H), 3.27 (m, 1H), 3.09 (t, 2H), 3.00 (t, 2H), 2.84 (td, 1H), 2.23 (s, 3H), 2.15 (bd, 1H), 2.10 (bd, 1H), 1.81 (tdd, 1H), 1.63 (tdd, 1H) ppm |
| I-124 | $^1$HNMR (CD$_3$CN) δ = 8.40 (d, 1H), 7.98 (d, 2H), 7.82 (dd, 1H), 7.76 (s, 1H), 7.68 (m, 1H), 7.62 (m, 1H), 7.56-7.45 (m, 3H), 7.33 (dd, 1H), 4.45 (bd, 1H), 4.06 (bd, 1H), 3.88 (d, 1H), 3.81 (d, 1H), 3.36 (m, 1H), 3.30 (t, 1H), 2.84 (t, 1H), 2.25-2.10 (m, 2H), 1.84 (m, 1H), 1.70 (m, 1H) ppm |
| I-125 | $^1$HNMR δ = 7.93 (s, 1H), 7.46-7.40 (m, 2H), 7.36 (d, 1H), 4.45-4.35 (m, 1H), 4.23 (s, 1H), 4.11-4.02 (m, 1H), 3.87 (d, 2H), 2.88-2.72 (m, 1H), 2.15-2.00 (m, 2H), 1.79-1.66 (m, 1H), 1.60-1.46 (m, 1H) |
| I-126 | $^1$HNMR (CD$_3$CN) δ = 7.16-7.05 (m, 4H), 6.87 (s, 1H), 6.39 (s, 1H), 5.11 (d, 1H), 5.03 (d, 1H), 4.46 (d, 1H), 3.91 (d, 1H), 3.32-3.23 (m, 2H), 3.01-2.93 (m, 4H), 2.84 (t, 1H), 2.27 (s, 3H), 2.23 (s, 3H), 2.18-2.07 (m, 2H), 1.82 (tdd, 1H), 1.65 (tdd, 1H) |
| I-128 | $^1$HNMR (CD$_3$CN) δ = 7.28-7.19 (m, 1H), 6.96-6.88 (m, 3H), 6.39 (s, 1H), 5.10 (d, 1H), 5.03 (d, 1H), 4.43 (d, 1H), 3.90 (d, 1H), 3.32-3.19 (m, 2H), 3.07-2.94 (m, 4H), 2.88 (td, 1H), 2.23 (s, 3H), 2.16-2.03 (m, 2H), 1.79 (tdd, 1H), 1.62 (tdd, 1H) |

| Ex | NMR Data |
|---|---|
| I-132 | $^1$HNMR δ = 7.12 (s, 1H), 6.49 (s, 1H), 5.31 (d, 1H), 5.22 (d, 1H), 4.35 (d, 1H), 3.95 (d, 1H), 3.45-3.20 (m, 2H), 2.82 (dd, 1H), 2.67 (dd, 2H), 2.21 (s, 3H), 2.06 (dd, 2H), 1.80-1.49 (m, 8H), 1.30-1.09 (m, 5H), 0.98-0.85 (m, 2H) ppm |
| I-133 | $^1$HNMR (CD$_3$CN) δ = 7.16-7.12 (m, 1H), 7.11-7.02 (m, 3H), 6.93 (s, 1H), 6.38 (s, 1H), 5.08 (d, 1H), 5.01 (d, 1H), 4.45 (bd, 1H), 3.99 (bd, 1H), 3.28-3.18 (m, 2H), 2.86-2.65 (m, 5H), 2.21 (s, 3H), 2.17-2.03 (m, 3H), 1.94-1.57 (m, 8H) ppm |
| I-134 | $^1$HNMR (CD$_3$CN) δ = 7.17 (s, 1H), 7.14-7.07 (m, 4H), 6.88 (s, 1H), 5.35 (d, 1H), 5.28 (d, 1H), 4.43 (d, 1H), 3.86 (d, 1H), 3.31-3.24 (m, 2H), 3.00-2.95 (m, 4H), 2.86 (ddd, 1H), 2.27 (s, 3H), 2.16 (d, 1H), 2.10 (d, 1H), 1.82 (tdd, 1H), 1.65 (tdd, 1H) ppm |
| I-136 | $^1$HNMR (CD$_3$CN) δ = 7.21 (m, 1H), 7.17 (s, 1H), 6.94-6.86 (m, 3H), 5.34 (d, 1H), 5.28 (d, 1H), 4.39 (d, 1H), 3.84 (d, 1H), 3.30-3.22 (m, 2H), 3.02 (t, 2H), 2.87 (ddd, 1H), 2.13 (d, 1H), 2.06 (d, 1H), 1.79 (tdd, 1H), 1.61 (tdd, 1H) ppm |
| I-138 | $^1$HNMR (CD$_3$CN) δ = 8.32 (d, 1H), 7.44 (d, 1H), 7.17 (s, 1H), 7.06 (dd, 1H), 6.89 (s, 1H), 5.34 (d, 1H), 5.28 (d, 1H), 4.42 (d, 1H), 3.85 (d, 1H), 3.30-3.23 (m, 2H), 3.12 (s, 4H), 2.86 (ddd, 1H), 2.23 (s, 3H), 2.15 (d, 1H), 2.09 (d, 1H), 1.80 (tdd, 1H), 1.62 (tdd, 1H) ppm |
| I-140 | $^1$HNMR (CD$_3$CN) δ = 7.17 (s, 1H), 6.90 (s, 1H), 5.35 (d, 1H), 5.27 (d, 1H), 4.42 (d, 1H), 3.86 (d, 1H), 3.32-3.21 (m, 2H), 2.86 (ddd, 1H), 2.75-2.67 (m, 2H), 2.20-2.04 (m, 2H), 1.85-1.50 (m, 9H), 1.42-1.12 (m, 4H), 1.00-0.88 (m, 2H) ppm |
| I-148 | $^1$HNMR δ = 7.18 (t, 1H), 7.13 (t, 1H), 7.03 (t, 1H), 6.91 (s, 1H), 5.43 (d, 1H), 5.35 (s, 1H), 4.32 (d, 1H), 3.94 (d, 1H), 3.30-3.21 (m, 2H), 2.82 (dd, 1H), 2.67 (dd, 2H), 2.10-2.00 (m, 2H), 1.83-1.48 (m, 8H), 1.35-1.10 (m, 5H), 0.95-0.85 (m, 2H) ppm |
| I-149 | $^1$HNMR (CD$_3$CN) δ = 7.17-7.10 (m, 1H), 7.11-7.03 (m, 3H), 6.95 (s, 1H), 6.89 (t, 1H), 6.82 (s, 1H), 6.78 (t, 1H), 5.23 (d, 1H), 5.17 (d, 1H), 4.44 (bd, 1H), 3.88 (bd, 1H), 3.30-3.21 (m, 2H), 2.98-2.67 (m, 5H), 2.15-2.03 (m, 3H), 1.94-1.58 (m, 8H) ppm |
| I-158 | $^1$HNMR δ = 7.18-7.05 (m, 5H), 7.03 (d, 1H), 6.93 (d, 1H), 6.90 (s, 1H), 4.47 (d, 1H), 3.94 (d, 1H), 3.70 (d, 1H), 3.62 (d, 1H), 3.35-3.22 (m, 2H), 2.95-2.85 (m, 4H), 2.78 (t, 1H), 2.25 (s, 3H), 2.23 (s, 3H), 2.15 (s, 3H), 2.10-1.94 (m, 2H), 1.61-1.45 (m, 2H) |
| I-160 | $^1$HNMR (CD$_3$CN) δ = 7.28-7.17 (m, 1H), 7.05 (d, 1H), 6.96 (d, 1H), 6.95-6.85 (m, 4H), 4.52 (d, 1H), 3.93 (d, 1H), 3.68 (d, 1H), 3.62 (d, 1H), 3.26-3.11 (m, 2H), 3.06-2.92 (m, 4H), 2.79 (td, 1H), 2.26 (s, 3H), 2.18 (s, 3H), 2.09-1.97 (m, 2H), 1.60 (qd, 2H) |
| I-166 | $^1$HNMR δ = 7.65-7.54 (m, 2H), 7.25-7.10 (m, 4H), 6.88 and 6.74 (s, 1H), 6.50 (s, 1H), 5.37-5.18 (m, 2H), 4.40 and 4.20 (d, 1H), 4.00 and 3.85 (d, 1H), 3.42-3.18 (m, 2H), 2.85 (dd, 1H), 2.38 and 2.20 (s, 3H), 2.22 and 2.20 (s, 3H), 2.19-2.10 and 2.05-1.93 (m, 2H), 1.83 and 1.67 (tdd, 1H), 1.59 and 1.48 (tdd, 1H) ppm |
| I-167 | $^1$HNMR δ = 7.86 (dd, 1H), 7.67-7.62 (m, 2H), 7.56 (dd, 1H), 7.43 (dd, 1H), 7.27 (d, 1H), 7.23 (dd, 1H), 6.50 (s, 1H), 5.34 (d, 1H), 5.24 (d, 1H), 4.40 (d, 1H), 3.99 (d, 1H), 3.45-3.20 (m, 2H), 2.83 (dd, 1H), 2.20 (s, 3H), 2.18-2.08 (m, 2H), 1.82 (tdd, 1H), 1.58 (tdd, 1H) ppm |
| I-172 | $^1$HNMR δ = 7.37 and 7.30 (s, 1H), 6.49 (s, 1H), 6.44 and 5.49 (dd, 1H), 6.35 and 6.24 (d, 1H), 5.35-5.18 (m, 2H), 4.37 and 4.29 (d, 1H), 3.95 (bs, 1H), 3.35-3.13 (m, 3H), 2.93 and 2.82 (dd, 1H), 2.21 (s, 3H), 2.18-2.02 (m, 2H), 1.85-1.48 (m, 6H), 1.35-1.05 (m, 6H) ppm |
| I-173 | $^1$HNMR δ = 7.51 and 7.34 (s, 1H), 7.13-7.04 (m, 4H), 6.54 and 5.67 (dd, 1H), 6.48 and 6.47 (s, 1H), 6.45 and 6.38 (d, 1H), 5.30 and 5.29 (d, 1H), 5.21 and 5.19 (d, 1H), 4.94 and 3.62 (m, 1H), 4.32 and 4.29 (d, 1H), 3.94 (m, 1H), 3.36-3.20 (m, 2H), 2.92-2.73 (m, 3H), 2.20 and 2.18 (s, 3H), 2.16-1.63 (m, 7H), 1.58 (m, 1H) ppm |
| I-174 | $^1$HNMR δ = 7.65-7.55 (m, 3H), 7.24-7.17 (m, 4H), 7.15 and 7.11 (s, 1H), 6.89 and 6.72 (s, 1H), 5.65-5.46 (m, 2H), 4.37 and 4.16 (d, 1H), 3.98 and 3.82 (d, 1H), 3.43-3.19 (m, 2H), 2.87 (dd, 1H), 2.38 and 2.20 (s, 3H), 2.18-2.10 and 2.05-1.92 (m, 2H), 1.82 and 1.66 (tdd, 1H), 1.58 and 1.43 (tdd, 1H) ppm |
| I-175 | $^1$HNMR δ = 7.84 (dd, 1H), 7.67-7.56 (m, 4H), 7.41 (t, 1H), 7.27 (d, 1H), 7.23 (td, 1H), 5.62 (d, 1H), 5.50 (d, 1H), 4.37 (d, 1H), 3.98 (d, 1H), 3.45-3.15 (m, 2H), 2.87 (dd, 1H), 2.18-2.09 (m, 2H), 1.82 (tdd, 1H), 1.56 (tdd, 1H) ppm |
| I-180 | $^1$HNMR (CD$_3$CN) δ = 7.17 (s, 1H), 7.13 and 7.02 (s, 1H), 6.49 and 5.55 (dd, 1H), 6.37 and 6.23 (d, 1H), 5.34 (d, 1H), 5.31 (d, 1H), 4.43 and 4.37 (d, 1H), 3.86 (d, 1H), 3.37-3.18 (m, 3H), 2.96 and 2.87 (ddd, 1H), 2.22-2.07 (m, 2H), 1.95-1.52 (m, 6H), 1.42-1.08 (m, 6H) ppm |
| I-181 | $^1$HNMR (CD$_3$CN) δ = 7.25-7.03 (m, 6H), 6.58 and 5.71 (dd, 1H), 6.46 and 6.39 (d, 1H), 5.35-5.23 (m, 2H), 4.98 and 4.67 (m, 1H), 4.42 and 4.34 (d, 1H), 3.84 and 3.63 (m, 1H), 3.34-3.23 (m, 2H), 2.96-2.65 (m, 3H), 2.20-2.04 (m, 2H), 2.00-1.58 (m, 6H) ppm |
| I-182 | $^1$HNMR δ = 7.65-7.57 (m, 2H), 7.33-6.70 (m, 8H), 5.43-5.33 (m, 2H), 4.38 and 4.17 (bd, 1H), 3.99 and 3.84 (bd, 1H), 3.43-3.18 (m, 2H), 2.85 (t, 1H), 2.38 and 2.20 (s, 3H), 2.17-1.90 (m, 2H), 1.88-1.42 (m, 2H) ppm |
| I-183 | $^1$HNMR δ = 7.86 (ddd, 1H), 7.68-7.62 (m, 2H), 7.55 (dd, 1H), 7.45-7.38 (m, 1H), 7.27 (d, 1H), 7.23 (dd, 1H), 7.18 (t, 1H), 7.03 (t, 1H), 6.90 (s, 1H), 5.50-5.32 (m, 2H), 4.38 and 4.12 (d, 1H), 3.99 and 3.80 (d, 1H), 3.45-3.15 (m, 2H), 2.86 (dd, 1H), 2.18-2.08 (m, 2H), 1.95 and 1.83 (tdd, 1H), 1.59 and 1.43 (tdd, 1H) ppm |
| I-188 | $^1$HNMR δ = 7.37 and 7.30 (s, 1H), 7.18 and 7.16 (t, 1H), 7.03 and 7.02 (t, 1H), 6.90 (s, 1H), 6.44 and 5.49 (dd, 1H), 6.35 and 6.24 (d, 1H), 5.45-5.30 (m, 2H), 4.35 and 4.28 (d, 1H), 3.94 (d, 1H), 3.40-3.15 (m, 3H), 2.93 and 2.82 (dd, 1H), 2.20-2.02 (m, 2H), 1.85-1.48 (m, 6H), 1.37-1.05 (m, 6H) ppm |
| I-189 | $^1$HNMR δ = 7.52 and 7.38 (s, 1H), 7.17 and 7.15 (t, 1H), 7.13-7.03 (m, 4H), 7.03 and 7.02 (t, 1H), 6.90 (s, 1H), 6.54 and 5.67 (dd, 1H), 6.45 and 6.38 (d, 1H), 5.45-5.32 (m, 2H), 4.95 and 3.63 (dd, 1H), 4.33 and 4.28 (d, 1H), 3.96-3.90 (m, 1H), 3.40-3.20 (m, 2H), 2.85 and 2.80 (dd, 1H), 2.82-2.70 (m, 2H), 2.16-1.68 (m, 6H), 1.60-1.49 (m, 2H) ppm |
| I-206 | $^1$HNMR (CD$_3$CN) δ = 7.62 (s, 1H), 7.50 (d, 1H), 7.33-7.26 (m, 2H), 7.25-7.17 (m, 1H), 6.39 (s, 1H), 5.10 (d, 1H), 5.03 (d, 1H), 4.48 (d, 1H), 3.92 (d, 1H), 3.36-3.21 (m, 2H), td (2.84, 1H), 2.48 (s, 3H), 2.22 (s, 3H), 2.20-2.09 (m, 2H), 1.85 (tdd, 1H), 1.68 (tdd, 1H) |

-continued

| Ex | NMR Data |
|---|---|
| I-207 | ¹HNMR δ = 8.05 (s, 1H), 7.76 (dd, 1H), 7.68 (dd, 1H), 7.46 (td, 1H), 7.38 (td, 1H), 6.49 (s, 1H), 5.32 (d, 1H), 5.23 (d, 1H), 4.37 (d, 1H), 3.98 (d, 1H), 3.43-3.20 (m, 2H), 2.84 (t, 1H), 2.20 (s, 3H), 2.09 (t, 2H), 1.82 (tdd, 1H), 1.58 (tdd, 1H) |
| I-208 | ¹HNMR δ = 8.14 (s, 1H), 7.62-7.51 (m, 1H), 7.28 (d, 1H), 7.26 (d, 1H), 6.49 (s, 1H), 5.32 (d, 1H), 5.23 (d, 1H), 4.37 (d, 1H), 3.97 (d, 1H), 3.44-3.20 (m, 2H), 2.85 (t, 1H), 2.21 (s, 3H), 2.12 (t, 2H), 1.89-1.76 (m, 1H), 1.65-1.50 (m, 1H) |
| I-210 | ¹HNMR δ = 8.44 (d, 1H), 8.12 (s, 1H), 7.75 (d, 1H), 7.35 (dd, 1H), 6.49 (s, 1H), 5.32 (d, 1H), 5.23 (d, 1H), 4.37 (d, 1H), 3.98 (d, 1H), 3.44-3.21 (m, 2H), 2.85 (t, 1H), 2.46 (s, 3H), 2.21 (s, 3H), 2.08-1.96 (m, 2H), 1.88-1.65 (m, 1H), 1.65-1.51 (m, 1H) |
| I-212 | ¹HNMR δ = 7.98 (s, 1H), 7.58 (s, 1H), 7.51 (d, 1H), 7.33 (m, 2H), 7.24 (m, 1H), 5.60 (d, 1H), 5.50 (d, 1H), 4.34 (m, 1H), 3.96 (m, 1H), 3.40-3.25 (m, 2H), 2.86 (m, 1H), 2.45 (s, 3H), 2.09 (m, 2H), 1.80 (m, 1H), 1.55 (m, 1H) ppm |
| I-213 | ¹HNMR δ = 8.05 (s, 1H), 7.76 (dd, 1H), 7.68 (dd, 1H), 7.58 (s, 1H), 7.45 (td, 1H), 7.36 (td, 1H), 5.60 (d, 1H), 5.50 (d, 1H), 4.34 (m, 1H), 3.95 (m, 1H), 3.25-3.39 (m, 2H), 2.86 (m, 1H), 2.10 (m, 2H), 1.80 (m, 1H), 1.55 (m, 1H) ppm |
| I-214 | ¹HNMR δ = 8.14 (s, 1H), 7.60-7.52 (m, 2H), 7.31-7.25 (m, 2H), 5.59 (d, 1H), 5.50 (d, 1H), 4.33 (m, 1H), 3.96 (m, 1H), 3.49-3.15 (m, 2H), 2.86 (m, 1H), 2.11 (m, 2H), 1.80 (m, 1H), 1.54 (m, 1H) ppm |
| I-216 | ¹HNMR δ = 8.44 (dd, 1H), 8.12 (s, 1H), 7.75 (d, 1H), 7.58 (s, 1H), 7.34 (dd, 1H), 5.60 (d, 1H), 5.50 (d, 1H), 4.34 (m, 1H), 3.97 (m, 1H), 3.42-3.26 (m, 2H), 2.87 (m, 1H), 2.46 (s, 3H), 2.12 (m, 2H), 1.81 (m, 1H), 1.56 (m, 1H) ppm |
| I-218 | ¹HNMR δ = 7.98 (s, 1H), 7.60-7.50 (m, 1H), 7.36-7.30 (m, 2H), 7.30-7.21 (m, 1H), 7.18 (t, 1H), 7.02 (t, 1H), 6.90 (s, 1H), 5.43 (d, 2H), 4.41-4.32 (m, 1H), 4.02-3.91 (m, 1H), 2.90-2.80 (m, 1H), 2.46 (s, 3H), 2.19-2.05 (m, 2H), 1.90-1.73 (m, 1H), 1.65-1.52 (m, 1H) |
| I-219 | ¹HNMR δ = 8.05 (s, 1H), 7.76 (d, 1H), 7.69 (d, 1H), 7.46 (t, 1H), 7.39 (t, 1H), 7.18 (t, 1H), 7.02 (t, 1H), 6.90 (s, 1H), 5.39 (d, 2H), 4.40-4.29 (m, 1H), 4.01-3.91 (m, 1H), 2.92-2.81 (m, 1H), 2.19-2.06 (m, 2H), 1.89-1.74 (m, 1H), 1.65-1.50 (m, 1H) |
| I-220 | ¹HNMR δ = 8.14 (s, 1H), 7.65-7.52 (m, 1H), 7.30-7.21 (m, 2H), 7.18 (t, 1H), 7.02 (t, 1H), 6.90 (s, 1H), 5.39 (d, 2H), 4.40-4.29 (m, 1H), 4.02-3.91 (m, 1H), 2.90-2.77 (m, 1H), 2.18-2.02 (m, 2H), 1.90-1.76 (m, 1H), 1.68-1.51 (m, 1H) |
| I-222 | ¹HNMR δ = 8.45 (bs, 1H), 8.12 (s, 1H), 7.75 (d, 1H), 7.38-7.33 (m, 1H), 7.18 (t, 1H), 7.02 (t, 1H), 6.90 (s, 1H), 5.39 (d, 2H), 4.39-4.31 (m, 1H), 4.01-3.92 (m, 1H), 3.00-2.78 (m, 1H), 2.46 (s, 3H), 2.18-2.03 (m, 2H), 1.89-1.76 (m, 1H), 1.65-1.52 (m, 1H) |
| I-223 | ¹HNMR δ = 8.02 (s, 1H), 7.15 (t, 1H), 7.02 (t, 1H), 6.90 (s, 1H), 5.38 (d, 2H), 4.39-4.30 (m, 1H), 4.04-3.91 (m, 1H), 2.87-2.79 (m, 1H), 2.28 (s, 3H), 2.16-2.04 (m, 2H), 1.90-1.73 (m, 1H), 1.62-1.49 (m, 1H) |
| I-224 | ¹HNMR δ = 7.98 (s, 1H), 7.50 (d, 1H), 7.47-7.42 (m, 2H), 7.39-7.32 (m, 3H), 7.27-7.20 (m, 1H), 4.46-4.38 (m, 1H), 4.12-4.04 (m, 1H), 3.88 (d, 2H), 2.85-2.76 (m, 1H), 2.46 (s, 3H), 2.17-2.05 (m, 2H), 1.79-1.67 (m, 1H), 1.62-1.48 (m, 1H) |
| I-225 | ¹HNMR δ = 8.05 (s, 1H), 7.76 (d, 1H), 7.68 (d, 1H), 7.50-7.44 (m, 3H), 7.41-7.30 (m, 2H), 4.46-4.36 (m, 1H), 4.11-4.02 (m, 1H), 3.87 (d, 2H), 2.86-2.74 (m, 1H), 2.17-2.05 (m, 2H), 1.80-1.68 (m, 1H), 1.64-1.50 (m, 1H) |
| I-226 | ¹HNMR δ = 8.13 (s, 1H), 7.65-7.52 (m, 2H), 7.49-7.43 (m, 2H), 7.35 (d, 1H), 7.25 (t, 1H), 4.46-4.37 (m, 1H), 4.13-4.04 (m, 1H), 3.88 (d, 2H), 2.86-2.75 (m, 1H), 2.18-2.04 (m, 2H), 1.80-1.69 (m, 1H), 1.62-1.50 (m, 1H) |
| I-228 | ¹HNMR δ = 8.46 (bs, 1H), 8.12 (s, 1H), 7.76 (d, 1H), 7.68-7.52 (m, 1H), 7.48-7.42 (m, 2H), 7.39-7.32 (m, 1H), 4.46-4.39 (m, 1H), 4.13-4.04 (m, 1H), 3.87 (d, 2H), 2.88-2.75 (m, 1H), 2.47 (s, 3H), 2.18-2.05 (m, 2H), 1.81-1.69 (m, 1H), 1.62-1.50 (m, 1H) |
| I-229 | ¹HNMR δ = 8.01 (s, 1H), 7.47-7.41 (m, 2H), 7.34 (d, 1H), 4.44-4.35 (m, 1H), 4.12-4.04 (m, 1H), 3.87 (d, 2H), 2.86-2.75 (m, 1H), 2.28 (s, 3H), 2.17-2.04 (m, 2H), 1.80-1.68 (m, 1H), 1.61-1.50 (m, 1H) |
| I-230 | ¹HNMR δ = 7.97 (s, 1H), 7.51 (d, 1H), 7.34 (d, 2H), 7.28-7.20 (m, 1H), 7.03 (d, 1H), 6.93 (d, 1H), 6.90 (s, 1H), 4.48 (d, 1H), 3.97 (d, 1H), 3.69 (d, 1H), 3.64 (d, 1H), 3.40-3.25 (m, 1H), 3.20 (t, 1H), 2.78 (t, 1H), 2.45 (s, 3H), 2.24 (s, 3H), 2.15 (s, 3H), 2.02 (t, 2H), 1.65-1.47 (m, 2H) |
| I-231 | ¹HNMR δ = 8.03 (s, 1H), 7.76 (dd, 1H), 7.68 (dd, 1H), 7.45 (td, 1H), 7.38 (td, 1H), 7.03 (d, 1H), 6.93 (d, 1H), 6.88 (s, 1H), 4.48 (d, 1H), 3.98 (d, 1H), 3.70 (d, 1H), 3.64 (d, 1H), 3.40-3.26 (m, 1H), 3.20 (t, 1H), 2.79 (t, 1H), 2.23 (s, 3H), 2.15 (s, 3H), 2.03 (t, 2H), 1.68-1.47 (m, 2H) |
| I-232 | ¹HNMR δ = 8.12 (s, 1H), 7.62-7.51 (m, 1H), 7.27 (t, 2H), 7.03 (d, 1H), 6.93 (d, 1H), 6.90 (s, 1H), 4.53-4.45 (m, 1H), 4.01-3.93 (m, 1H), 3.69 (d, 1H), 3.63 (d, 1H), 3.40-3.15 (m, 2H), 2.78 (t, 1H), 2.23 (s, 3H), 2.15 (s, 3H), 2.14-2.00 (m, 2H), 1.68-1.48 (m, 2H) |
| I-235 | ¹HNMR δ = 8.00 (s, 1H), 7.03 (d, 1H), 6.93 (d, 1H), 6.89 (s, 1H), 4.48 (d, 1H), 3.96 (d, 1H), 3.68 (d, 1H), 3.63 (d, 1H), 3.40-3.15 (m, 2H), 2.77 (t, 1H), 2.28 (s, 3H), 2.23 (s, 3H), 2.15 (s, 3H), 2.04 (t, 2H), 1.65-1.48 (m, 2H) |
| I-236 | ¹HNMR δ = 8.40 (dd, 1H), 7.74-7.56 (m, 5H), 7.17 (dd, 1H), 5.62 (d, 1H), 5.50 (d, 1H), 4.37 (m, 1H), 3.97 (m, 1H), 3.50-3.20 (m, 2H), 2.87 (m, 1H), 2.40 (s, 3H), 2.12 (m, 2H), 1.85 (m, 1H), 1.57 (m, 1H) ppm |
| I-237 | ¹HNMR δ = 7.68-7.50 (m, 3H), 7.25-7.15 (m, 3H), 7.11 (d, 1H), 7.03 (d, 1H), 6.93 (d, 1H), 6.90 (s, 1H), 4.51 (d, 1H), 3.97 (d, 1H), 3.71 (d, 1H), 3.63 (d, 1H), 3.40-3.15 (m, 2H), 2.79 (t, 1H), 2.38 (s, 3H), 2.24 (s, 3H), 2.14 (s, 3H), 2.12-2.00 (m, 2H), 1.65-1.48 (m, 2H) |
| I-238 | ¹HNMR δ = 7.92 (s, 1H), 7.02 (d, 1H), 6.93 (d, 1H), 6.89 (s, 1H), 4.46 (d, 1H), 4.22 (s, 1H), 3.95 (d, 1H), 3.68 (d, 1H), 3.62 (d, 1H), 3.34-3.23 (m, 1H), 3.18 (t, 1H), 2.77 (t, 1H), 2.23 (s, 3H), 2.14 (s, 3H), 2.02 (t, 2H), 1.63-1.44 (m, 2H) |
| I-239 | ¹HNMR δ = 7.93 (s, 1H), 7.17 (t, 1H), 7.02 (t, 1H), 6.90 (s, 1H), 5.38 (d, 2H), 4.37-4.30 (m, 1H), 4.23 (s, 1H), 4.01-3.89 (m, 1H), 2.89-2.77 (m, 1H), 2.15-2.00 (m, 2H), 1.84-1.70 (m, 1H), 1.61-1.49 (m, 1H) |

-continued

| Ex | NMR Data |
|---|---|
| I-240 | $^1$HNMR δ = 7.73 (s, 1H), 7.59 (s, 1H), 7.54 (d, 1H), 7.42-7.27 (m, 4H), 5.63 (d, 1H), 5.50 (d, 1H), 4.37 (d, 1H), 3.98 (d, 1H), 3.45-3.20 (m, 2H), 2.87 (dd, 1H), 2.18-2.08 (m, 2H), 1.83 (tdd, 1H), 1.58 (tdd, 1H) ppm |
| I-241 | $^1$HNMR δ = 7.73 (s, 1H), 7.54 (d, 1H), 7.42-7.27 (m, 4H), 7.19 (t, 1H), 7.03 (t, 1H), 6.91 (s, 1H), 5.45 (d, 1H), 5.36 (d, 1H), 4.38 (d, 1H), 4.01 (d, 1H), 3.45-3.22 (m, 2H), 2.86 (dd, 1H), 2.20-2.09 (m, 2H), 1.83 (tdd, 1H), 1.60 (tdd, 1H) ppm |
| I-242 | $^1$HNMR δ = 7.92 (d, 1H), 7.73 (s, 1H), 7.58-7.53 (dd, 1H), 7.45-7.28 (m, 3H), 6.50 (s, 1H), 5.34 (d, 1H), 5.23 (d, 1H), 4.40 (d, 1H), 3.99 (d, 1H), 3.43-3.20 (m, 2H), 2.85 (dd, 1H), 2.21 (s, 3H), 2.18-2.09 (m, 2H), 1.84 (tdd, 1H), 1.59 (tdd, 1H) ppm |

The chemical NMR shifts were measured in ppm at 400 MHz, unless indicated otherwise in the solvent DMSO-$d_6$ using tetramethylsilane as internal standard.

The following abbreviations describe signal splitting:

b=broad, s=singlet, d=doublet, t=triplet, q=quadruplet, m=multiplet

USE EXAMPLES

Example A

Phytophthora Test (Tomato)/Protective

| Solvent: | 49 parts by weight of N,N-dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. 1 day after the treatment, the plants are inoculated with a spore suspension of Phytophthora infestans and then remain at 100% rel. humidity and 22° C. for 24 h. The plants are then placed in a climatized chamber at about 96% relative atmospheric humidity and a temperature of about 20° C.

Evaluation is carried out 7 days after the inoculation. 0% means an efficacy which corresponds to that of the control, whereas an efficacy of 100% means that no infection is observed.

In this test, the compounds according to the invention I-1, I-2, I-3, I-9, I-15, I-26, I-27, I-35, I-43, I-50, I-51, I-52, I-53, I-59, I-74, I-77, I-79, I-80, I-81, I-83, I-93, I-96, I-98, I-99, I-100, I-101, I-102, I-103, I-104, I-105, I-107, I-108, I-109, I-114, I-115, I-116, I-117, I-121, I-122 and I-123 show, at an active compound concentration of 500 ppm, an efficacy of 70% or more.

Example B

Plasmopara Test (Grapevine)/Protective

| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of Plasmopara viticola and then remain in an incubation cabin at about 20° C. and 100% relative atmospheric humidity for 1 day. The plants are then placed in a greenhouse at about 21° C. and an atmospheric humidity of about 90% for 4 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

In this test, the compounds according to the invention I-1, I-9, I-35, I-43, I-50, I-51, I-53, I-59, I-74, I-80, I-81, I-93, I-96, I-98, I-99, I-100, I-101, I-102, I-103, I-104, I-105, I-108, I-109, I-114, I-115, I-116 and I-117 show, at an active compound concentration of 100 ppm, an efficacy of 70% or more.

The invention claimed is:

1. A compound of formula (I),

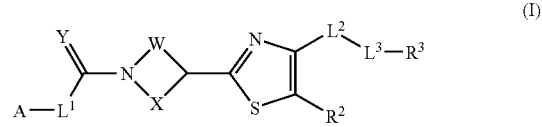

in which the symbols have the following meanings:

A represents methyl

Or

A represents unsubstituted or substituted phenyl, where the substituents independently of one another are selected from:

cyano, nitro, halogen, $C_1$-$C_6$-alkyl, $C_1$-$C_3$-haloalkyl, $C_3$-$C_6$-cycloalkyl, $C_3$-$C_6$-halocycloalkyl, $C_4$-$C_{10}$-cycloalkylalkyl, $C_4$-$C_{10}$-alkylcycloalkyl, $C_5$-$C_{10}$-alkylcycloalkylalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_2$-alkyl)silyl, benzyl, phenyl, hydroxyl, $C_1$-$C_4$-alkoxy, $C_1$-$C_4$-haloalkoxy, $OCH_2OCH_3$, SH, $C_1$-$C_4$-alkylthio, $C_1$-$C_6$-haloalkylthio, CHO, COOH, ($C_1$-$C_4$-alkoxy)carbonyl, $CONR^6R^7$, $CR^6$=$NOR^7$, ($C_1$-$C_4$-alkyl)carbonyl, ($C_1$-$C_4$-haloalkyl)carbonyl, ($C_1$-$C_4$-alkyl)carbonyloxy, ($C_1$-$C_4$-alkyl)carbonylthio, $C_1$-$C_4$-alkylsulphinyl, $C_1$-$C_4$-haloalkylsulphinyl, $C_1$-$C_4$- alkylsulphonyl, $C_1$-$C_4$-haloalkylsulphonyl, $NR^6R^7$, $NR^6COR^7$, $SF_5$, $SO_2NR^6R^7$, $C_2$-$C_4$-alkoxyalkyl or 1-methoxycyclopropyl or A is an optionally benzo-fused unsubstituted or substituted 5- or 6-membered heteroaryl, where the substituents independently of one another are selected from:

substituents at carbon:

cyano, nitro, halogen, $C_1$-$C_6$-alkyl, $C_1$-$C_3$-haloalkyl, $C_3$-$C_6$-cycloalkyl, $C_3$-$C_6$-halocycloalkyl $C_4$-$C_{10}$-cycloalkylalkyl, $C_4$-$C_{10}$-alkylcycloalkyl, $C_5$-$C_{10}$-alkylcycloalkylalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_2$-alkyl)silyl, benzyl, phenyl, hydroxyl, $C_1$-$C_4$-alkoxy, $C_1$-$C_4$-haloalkoxy, $OCH_2OCH_3$, SH, $C_1$-$C_4$-alkylthio, $C_1$-$C_6$-haloalkylthio, CHO, COOH, ($C_1$-$C_4$-alkoxy)carbonyl, $CONR^6R^7$, $CR^6$=$NOR^7$, ($C_1$-$C_4$-alkyl)carbonyl, ($C_1$-$C_4$-haloalkyl)carbonyl, ($C_1$-$C_4$-alkyl)carbonyloxy, ($C_1$-$C_4$-alkyl)carbonylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, $NR^6R^7$, $NR^6COR^7$, $SF_5$, $SO_2NR^6R^7$, $C_2$-$C_4$-alkoxyalkyl or 1-methoxycyclopropyl if the 5- or 6-membered heteroaryl contains nitrogen the substituents at the nitrogen are selected from substituents at nitrogen:

hydroxyl, $NR^6R^7$, $C_1$-$C_6$-alkyl, $C_1$-$C_3$-haloalkyl, $C_3$-$C_6$-cycloalkyl, $C_3$-$C_6$-halocycloalkyl, $C_4$-$C_{10}$-alkylcycloalkyl, $C_2$-$C_6$-alkenyl, $C_2$-$C_6$-haloalkenyl, $C_2$-$C_6$-alkynyl, or $C_2$-$C_6$-haloalkynyl $L^1$ represents $(C(R^1)_2)_n$ where n=0 to 3

$R^1$ are identical or different and independently of one another represent hydrogen, halogen, $C_1$-$C_2$-alkyl, $C_1$-$C_2$-haloalkyl or cyano, with the provision that $L^1$ may contain at most two $R^1$ different from hydrogen Y represents sulphur or oxygen, W represents an unsubstituted or monosubstituted $C_1$- to $C_3$-carbon chain, where the substituent is selected from the group consisting of oxo, hydroxyl, cyano and $C_1$-$C_4$-alkyl X represents an unsubstituted or monosubstituted $C_1$- to $C_2$-carbon chain, where the substituent is selected from the group consisting of oxo, hydroxyl, cyano and $C_1$-$C_4$-alkyl $R^2$ represents hydrogen, $C_1$-$C_2$-alkyl, $C_1$-$C_2$-haloalkyl or halogen $L^2$ represents —$C(R^8)_2$—$C(R^8)_2$— or —$CR^9$=$CR^9$— or —C≡C—

$L^3$ represents a direct bond or $L^3$ represents a $C_1$- to $C_4$-carbon chain which may contain up to two substituents, where the substituents independently of one another are selected from:

halogen, $C_1$-$C_2$-alkyl, $C_1$-$C_2$-alkoxy, $C_1$-$C_2$-haloalkyl or $C_3$-$C_6$-cycloalkyl $R^3$ represents methyl, $C_1$-$C_2$-haloalkyl, —CH=$CH_2$, —C≡CH, or unsubstituted or monosubstituted $C_3$-$C_{10}$-cycloalkyl, where the substituent is selected from:

cyano, halogen, $C_1$-$C_6$-alkyl, $C_1$-$C_3$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_2$-alkyl)silyl, phenyl, hydroxyl, oxo, $C_1$-$C_6$-alkoxy, $C_1$-$C_6$-haloalkoxy, $C_2$-$C_6$-alkenyloxy, $C_2$-$C_6$-alkynyloxy, $C_1$-$C_6$-alkylthio or $C_1$-$C_6$-haloalkylthio, or $R^3$ represents unsubstituted or substituted phenyl, where the substituents independently of one another are selected from:

cyano, nitro, halogen, $C_1$-$C_6$-alkyl, $C_1$-$C_3$-haloalkyl, $C_3$-$C_6$-cycloalkyl, $C_3$-$C_6$-halocycloalkyl, $C_4$-$C_{10}$-cycloalkylalkyl, $C_4$-$C_{10}$-halocycloalkylalkyl, $C_4$-$C_{10}$-alkylcycloalkyl, $C_5$-$C_{10}$-alkylcycloalkylalkyl, $C_4$-$C_{10}$-cycloalkoxyalkyl, $C_2$-$C_6$-alkenyl, $C_2$-$C_6$-haloalkenyl, $C_3$-$C_8$-cycloalkenyl, $C_3$-$C_8$-halocycloalkenyl, $C_2$-$C_6$-alkynyl, $C_2$-$C_6$-haloalkynyl, $C_2$-$C_6$-alkoxyalkyl, $C_2$-$C_6$-haloalkoxyalkyl, $C_3$-$C_8$-alkoxyalkoxyalkyl, tri($C_1$-$C_2$-alkyl)silyl, benzyl, phenyl, hydroxyl, $C_1$-$C_6$-alkoxy, $C_2$-$C_6$-alkoxyalkoxy, $C_1$-$C_6$-haloalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_3$-$C_6$-cycloalkoxy, $C_3$-$C_6$-cycloalkyloxy, $C_3$-$C_6$-halocycloalkoxy, $C_4$-$C_{10}$-cycloalkylalkyloxy, $NR^6R^7$, SH, $SF_5$, $C_1$-$C_6$-alkylthio, $C_1$-$C_6$-haloalkylthio, $C_2$-$C_6$-alkylalkylthio, $C_3$-$C_6$-cycloalkylthio, CHO, COOH, ($C_1$-$C_6$-alkoxy)carbonyl, $CONR^6R^7$, $CR^6$=$NOR^7$, ($C_1$-$C_6$-alkyl)carbonyl, ($C_1$-$C_6$-haloalkyl)carbonyl, ($C_1$-$C_6$-alkyl)carbonyloxy, ($C_1$-$C_6$-haloalkyl)carbonyloxy, ($C_1$-$C_6$-alkyl)carbonylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $NR^6COR^7$ or $SO_2NR^6R^7$ or $R^3$ represents saturated or partially or fully unsaturated naphthyl or indenyl, which may contain up to two substituents, where the substituents independently of one another are selected from:

cyano, halogen, $C_1$-$C_6$-alkyl, $C_1$-$C_3$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_2$-alkyl)silyl, phenyl, hydroxyl, $C_1$-$C_6$-alkoxy, $C_1$-$C_6$-haloalkoxy, $C_2$-$C_6$-alkenyloxy, $C_2$-$C_6$-alkynyloxy, $C_1$-$C_6$-alkylthio or $C_1$-$C_6$-haloalkylthio, or $R^3$ represents an unsubstituted or substituted 5- or 6-membered heteroaryl radical, where the substituents independently of one another are selected from the list below:

substituents at carbon: cyano, nitro, halogen, $C_1$-$C_6$-alkyl, $C_1$-$C_3$-haloalkyl, $C_3$-$C_6$-cycloalkyl, $C_3$-$C_6$-halocycloalkyl, $C_4$-$C_{10}$-cycloalkylalkyl, $C_4$-$C_{10}$-alkylcycloalkyl, $C_5$-$C_{10}$-alkylcycloalkylalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_2$-alkyl)silyl, benzyl, phenyl, hydroxyl, $C_1$-$C_4$-alkoxy, $C_1$-$C_4$-haloalkoxy, $OCH_2OCH_3$, SH, $C_1$-$C_4$-alkylthio, $C_1$-$C_6$-haloalkylthio, COOH, ($C_1$-$C_4$-alkoxy)carbonyl, $CONR^6R^7$, ($C_1$-$C_4$-alkyl)carbonyl, ($C_1$-$C_4$-haloalkyl)carbonyl, ($C_1$-$C_4$-alkyl)carbonyloxy, ($C_1$-$C_4$-alkyl)carbonylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, $NR^6R^7$, $NR^6COR^7$, $SF_5$, $SO_2NR^6R^7$, $C_2$-$C_4$-alkoxyalkyl or 1-methoxycyclopropyl if the 5- or 6-membered heteroaryl contains nitrogen the substituents at the nitrogen are selected from substituents at nitrogen:hydroxyl, $C_1$-$C_6$-alkyl, $C_1$-$C_3$-haloalkyl, $C_3$-$C_6$-cycloalkyl, $C_3$-$C_6$-halocycloalkyl, $C_4$-$C_{10}$-alkylcycloalkyl, $C_2$-$C_6$-alkenyl, $C_2$-$C_6$-haloalkenyl, $C_2$-$C_6$-alkynyl, $C_2$-$C_6$-haloalkynyl or phenyl or $R^3$ represents benzo-fused unsubstituted or substituted 5- or 6-membered heteroaryl which may contain up to two substituents, where the substituents independently of one another are selected from:

substituents at carbon: cyano, nitro, halogen, $C_1$-$C_6$-alkyl, $C_1$-$C_3$-haloalkyl, $C_3$-$C_6$-cycloalkyl, $C_3$-$C_6$-halocycloalkyl, $C_4$-$C_{10}$-cycloalkylalkyl, $C_4$-$C_{10}$-alkylcycloalkyl, $C_5$-$C_{10}$-alkylcycloalkylalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_2$-alkyl)silyl, benzyl, phenyl, hydroxyl, $C_1$-$C_4$-alkoxy, $C_1$-$C_4$-haloalkoxy, $OCH_2OCH_3$, SH, $C_1$-$C_4$-alkylthio, $C_1$-$C_6$-haloalkylthio, COOH, ($C_1$-$C_4$-alkoxy)carbonyl, $CONR^6R^7$, ($C_1$-$C_4$-alkyl)carbonyl, ($C_1$-$C_4$-haloalkyl)carbonyl, ($C_1$-$C_4$-alkyl)carbonyloxy, ($C_1$-$C_4$-alkyl)carbonylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, $NR^6R^7$, $NR^6COR^7$, $SF_5$, $SO_2NR^6R^7$, $C_2$-$C_4$-alkoxyalkyl or 1-methoxycyclopropyl if the 5- or 6-membered heteroaryl contains nitrogen the substituents at the nitrogen are selected from substituents at nitrogen:$C_1$-$C_6$-alkyl, $C_1$-$C_3$-haloalkyl, $C_3$-$C_6$-cycloalkyl, $C_3$-$C_6$-halocycloalkyl, $C_4$-$C_{10}$-alkylcycloalkyl, $C_2$-$C_6$-alkenyl, $C_2$-$C_6$-haloalkenyl, $C_2$-$C_6$-alkynyl, $C_2$-$C_6$-haloalkynyl or phenyl or $R^3$ is an unsubstituted or monosubstituted 5- to 15-membered heterocyclyl radical which is attached via a carbon atom and which may contain up to two further heteroatoms selected from the group consisting of nitrogen, oxygen and sulphur, where the substituent is selected from:

substituents at carbon: cyano, halogen, $C_1$-$C_6$-alkyl, $C_1$-$C_3$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_2$-alkyl)silyl, phenyl, hydroxyl, $C_1$-$C_6$-alkoxy, $C_1$-$C_6$-haloalkoxy, $C_2$-$C_6$-alkenyloxy, $C_2$-$C_6$-alkynyloxy, $C_1$-$C_6$-alkylthio or $C_1$-$C_6$-haloalkylthio if said up to two further heteroatoms includes nitrogen, the substituents at nitrogen may be: $C_1$-$C_6$-alkyl, $C_1$-$C_3$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_2$-alkyl)silyl or phenyl $R^6$, $R^7$ independently of one another represent hydrogen, $C_1$-$C_4$-alkyl, $C_1$-$C_3$-haloalkyl, $C_3$-$C_6$-cycloalkyl, $R^8$ are identical or different and independently of one another represent hydrogen, halogen, $C_1$-$C_4$-alkyl, $C_1$-$C_4$-alkoxy, $C_3$-$C_6$-cycloalkyl or $C_1$-$C_3$-haloalkyl, $R^9$ are identical or different and independently of one another represent hydrogen, $C_1$-$C_4$-alkyl or $C_3$-$C_6$-cycloalkyl, or an agrochemically active salt thereof.

2. A compound of formula (I) according to claim 1 in which the symbols have the following meanings:

A represents methyl or

A represents phenyl which may contain up to two substituents, where the substituents independently of one another are selected from:

cyano, nitro, halogen, $C_1$-$C_4$-alkyl, $C_1$-$C_3$-haloalkyl, $C_3$-$C_6$-cycloalkyl, $C_2$-$C_4$-alkenyl, $C_2$-$C_4$-alkynyl, hydroxyl, $C_1$-$C_4$-alkoxy, $C_1$-$C_4$-haloalkoxy, $C_1$-$C_4$-alkylthio, $C_1$-$C_4$-haloalkylthio, ($C_1$-$C_4$-alkoxy)carbonyl, ($C_1$-$C_4$-alkyl)carbonyl, ($C_1$-$C_4$-haloalkyl)carbonyl, $C_1$-$C_4$-alkylsulphinyl, $C_1$-$C_4$-haloalkylsulphinyl, $C_1$-$C_4$-alkylsulphonyl or $C_1$-$C_4$-haloalkylsulphonyl, or A represents a heteroaromatic radical selected from the group below: furan-2-yl, furan-3-yl, thiophen-2-yl, thiophen-3-yl, isoxazol-3-yl, isoxazol-4-yl, isoxazol-5-yl, 1H-pyrrol-1-yl, 1H-pyrrol-2-yl, 1H-pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-tri-azol-3-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1H-indol-1-yl, 1H-indol-2-yl, 1H-indol-3-yl, 1H-indol-4-yl, 1H-indol-5-yl, 1H-indol-6-yl, 1H-indol-7-yl, 1H-benzimidazol-1-yl, 1H-benzimidazol-2-yl, 1H-benzimidazol-4-yl, benzimidazol-5-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzoxazol-2-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl, which may contain up to two substituents, where the substituents independently of one another are selected from:

substituents at carbon: cyano, halogen, $C_1$-$C_4$-alkyl, $C_1$-$C_3$-haloalkyl, hydroxyl, $C_1$-$C_4$-alkoxy, $C_1$-$C_4$-haloalkoxy, $C_1$-$C_4$-alkylthio and/or $C_1$-$C_4$-haloalkylthio, substituents at nitrogen: $C_1$-$C_4$-alkyl, $C_1$-$C_3$-haloalkyl, cyclopropyl, $C_2$-$C_4$-alkenyl or $C_2$-$C_4$-alkynyl, $L^1$ represents $(C(R^1)_2)_n$ where n=0 to 3

$R^1$ are identical or different and independently of one another represent hydrogen, chlorine, fluorine, methyl, $CF_3$ or cyano, with the provision that $L^1$ may contain at most two $R^1$ different from hydrogen, Y represents sulphur or oxygen, W represents an unsubstituted or monosubstituted $C_1$- to $C_2$-carbon chain, where the substituent is selected from the group consisting of cyano and $C_1$-$C_2$-alkyl X represents an unsubstituted or monosubstituted $C_1$- to $C_2$-carbon chain, where the substituent is selected from the group consisting of cyano and $C_1$-$C_2$-alkyl, $R^2$ represents hydrogen, $C_1$-$C_2$-alkyl or halogen, $L^2$ represents —C($R^8$)$_2$—C($R^8$)$_2$— or —$CR^9$=$CR^9$— or —C≡C—, $L^3$ represents a direct bond, or $L^3$ represents a $C_1$- to $C_4$-carbon chain which may contain up to two substituents, where the substituents independently of one another are selected from:

$C_1$-$C_2$-alkyl, $C_1$-$C_2$alkoxy, $C_1$-$C_2$-haloalkyl or cyclopropyl, $R^3$ represents methyl, $C_1$-$C_2$-haloalkyl, —CH=$CH_2$, —C≡CH, or unsubstituted or monosubstituted $C_3$-$C_{10}$-cycloalkyl, where the substituent is selected from:

halogen, $C_1$-$C_6$-alkyl, $C_3$-$C_6$-cycloalkyl, $C_2$-$C_6$-alkenyl, $C_2$-$C_6$-alkynyl, tri($C_1$-$C_2$-alkyl)silyl, phenyl or oxo, or $R^3$ represents phenyl which may contain up to three substituents, where the substituents independently of one another are selected from:

cyano, nitro, halogen, $C_1$-$C_6$-alkyl, $C_1$-$C_3$-haloalkyl, $C_3$-$C_6$-cycloalkyl, $C_3$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_2$-alkyl)silyl, phenyl, hydroxyl, $C_1$-$C_6$-alkoxy, $C_1$-$C_6$-haloalkoxy, $C_1$-$C_6$-alkylthio or $C_1$-$C_6$-haloalkylthio, or $R^3$ represents naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 1H-inden-2-yl, 1H-inden-3-yl, 1H-inden-4-yl, 1H-inden-5-yl, 1H-inden-6-yl, 1H-inden-7-yl, 2,3-dihydro-1H-inden-1-yl, 2,3-dihydro-1H-inden-2-yl, 2,3-dihydro-1H-inden-4-yl or 2,3-dihydro-1H-inden-5-yl, which may contain up to two substituents, where the substituents independently of one another are selected from:

cyano, halogen, $C_1$-$C_6$-alkyl, $C_1$-$C_3$-haloalkyl, $C_3$-$C_6$-cycloalkyl, phenyl, hydroxyl, $C_1$-$C_6$-alkoxy, $C_1$-$C_3$-haloalkoxy, $C_1$-$C_6$-alkylthio or $C_1$-$C_3$-haloalkylthio, or $R^3$ represents furan-2-yl, furan-3-yl, thiophen-2-yl, thiophen-3-yl, isoxazol-3-yl, isoxazol-4-yl, isoxazol-5-yl, 1H-pyrrol-1-yl, 1H-pyrrol-2-yl, 1H-pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, or 1,2,4-triazin-3-yl, which may contain up to two substituents, where the substituents independently of one another are selected from:

substituents at carbon: cyano, halogen, $C_1$-$C_6$-alkyl, $C_1$-$C_3$-haloalkyl, $C_3$-$C_6$-cycloalkyl, phenyl, hydroxyl, $C_1$-$C_4$-alkoxy, $C_1$-$C_4$-haloalkoxy, $C_1$-$C_4$-alkylthio or $C_1$-$C_4$-haloalkylthio, substituents at nitrogen: $C_1$-$C_6$-alkyl, $C_1$-$C_3$-haloalkyl, $C_3$-$C_6$-cycloalkyl, $C_2$-$C_6$-alkenyl, $C_2$-$C_6$-alkynyl or phenyl, or $R^3$ represents 1H-indol-1-yl, 1H-indol-2-yl, 1H-indol-3-yl, 1H-indol-4-yl, 1H-indol-5-yl, 1H-indol-6-yl, 1H-indol-7-yl, 1H-benzimidazol-1-yl, 1H-benzimidazol-2-yl, 1H-benzimidazol-4-yl, benzimidazol-5-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl, which may contain up to two substituents, where the substituents independently of one another are selected from:

substituents at carbon: cyano, halogen, $C_1$-$C_6$-alkyl, $C_1$-$C_3$-haloalkyl, $C_3$-$C_6$-cycloalkyl, phenyl, hydroxyl, $C_1$-$C_4$-alkoxy, $C_1$-$C_4$-haloalkoxy, $C_1$-$C_4$-alkylthio or $C_1$-$C_4$-haloalkylthio, substituents at nitrogen: $C_1$-$C_6$-alkyl, $C_1$-$C_3$-haloalkyl, $C_3$-$C_6$-cycloalkyl, $C_2$-$C_6$-alkenyl, $C_2$-$C_6$-alkynyl or phenyl, or $R^3$ represents an unsubstituted or monosubstituted 5- to 6-membered heterocyclyl radical which is attached via a carbon atom and which may contain up to two further heteroatoms selected from the group consisting of nitrogen, oxygen and sulphur, where the substituent is selected from:

substituents at carbon: $C_1$-$C_6$-alkyl, $C_1$-$C_3$-haloalkyl, $C_3$-$C_6$-cycloalkyl, $C_2$-$C_6$-alkenyl, $C_2$-$C_6$-alkynyl, tri($C_1$-$C_2$-alkyl)silyl or phenyl, if said up to two further heteroatoms include nitrogen, substituents at nitrogen: $C_1$-$C_6$-alkyl, $C_3$-$C_6$-cycloalkyl, $C_2$-$C_6$-alkenyl, $C_2$-$C_6$-alkynyl, tri($C_1$-$C_2$-alkyl)silyl or phenyl, $R^8$ are identical or different and independently of one another represent hydrogen, halogen, $C_1$-$C_2$-alkyl, $C_1$-$C_2$-alkoxy, cyclopropyl or $C_1$-$C_2$-haloalkyl, $R^9$ are identical or different and independently of one another represent hydrogen, $C_1$-$C_2$-alkyl or cyclopropyl or an agrochemically active salt thereof.

3. Compounds of the formula (I) according to claim 1 in which the symbols have the following meanings, A represents methyl, or A represents phenyl which may contain up to two substituents, where the substituents independently of one another are selected from the list below:

cyano, nitro, halogen, $C_1$-$C_2$-alkyl, $C_1$-$C_2$-haloalkyl, hydroxyl, $C_1$-$C_2$-alkoxy or $C_1$-$C_2$-haloalkoxy, or A represents a heteroaromatic radical selected from the group below: furan-2-yl, furan-3-yl, thiophen-2-yl, thiophen-3-yl, oxazol-2-yl, oxazol-4-yl, oxazol-5-yl, thiazol-2-yl, thiazol-4-yl, thiazol-5-yl; pyrazol-1-yl, pyrazol-3-yl, pyrazol-4-yl, imidazol-1-yl, imidazol-2-yl, imidazol-4-yl, 1,2,4-triazol-1-yl, pyridin-2-yl, pyridin-3-yl, pyridin-4-yl, 1,2,4-triazin-3-yl, 1H-benzimidazol-2-yl or 1,3-benzothiazol-2-yl, which may contain up to two substituents, where the substituents independently of one another are selected from:

substituents at carbon: cyano, halogen, $C_1$-$C_2$-alkyl, $C_1$-$C_2$-haloalkyl, hydroxyl, $C_1$-$C_2$-alkoxy or $C_1$-$C_2$-haloalkoxy, substituents at nitrogen: $C_1$-$C_2$-alkyl or $C_1$-$C_2$-haloalkyl, $L^1$ represents $(C(R^1)_2)_n$ where n=0 to 3, $R^1$ are identical or different and independently of one another represent hydrogen or methyl, with the provision that $L^1$ may contain at most two methyl substituents, Y represents sulphur or oxygen, W represents —$CH_2CH_2$—, X represents —$CH_2CH_2$—, $R^2$ represents hydrogen, methyl or halogen, $L^2$ represents —C($R^8$)$_2$—C($R^8$)$_2$— or —C$R^9$=C$R^9$— or —C≡C—, $L^3$ represents a direct bond, or $L^3$ represents a $C_1$- to $C_4$-carbon chain which may contain up to two substituents, where the substituents independently of one another are selected from:

methyl, methoxy and/or $CF_3$, $R^3$ represents methyl, $C_1$-$C_2$-haloalkyl, —CH=CH$_2$, —C≡CH, or unsubstituted or monosubstituted $C_3$-$C_{10}$-cycloalkyl, where the substituent is selected:

fluorine, chlorine, methyl, ethyl, cyclopropyl, cyclopentyl or cyclohexyl, or $R^3$ represents phenyl which may contain up to three substituents, where the substituents independently of one another are selected from:

cyano, halogen, $C_1$-$C_6$-alkyl, $C_1$-$C_3$-haloalkyl, phenyl, hydroxyl, $C_1$-$C_6$-alkoxy, $C_1$-$C_6$-haloalkoxy, $C_1$-$C_6$-alkylthio or $C_1$-$C_6$-haloalkylthio, or $R^3$ represents naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 1H-inden-2-yl, 1H-inden-3-yl, 1H-inden-4-yl, 1H-inden-5-yl, 1H-inden-6-yl, 1H-inden-7-yl, 2,3-dihydro-1H-inden-1-yl, 2,3-dihydro-1H-inden-2-yl, 2,3-dihydro-1H-inden-4-yl or 2,3-dihydro-1H-inden-5-yl, which may contain up to two substituents, where the substituents independently of one another are selected from:

fluorine, chlorine, bromine, iodine, methyl, ethyl, $CF_3$, $CHF_2$, cyclopropyl, phenyl, hydroxyl, OMe, OEt, $OCF_3$, $OCHF_2$, $OC_2F_5$, SMe or $SCF_3$, or $R^3$ represents furan-2-yl, furan-3-yl, thiophen-2-yl, thiophen-3-yl, isoxazol-3-yl, isoxazol-4-yl, isoxazol-5-yl, 1H-pyrrol-1-yl, 1H-pyrrol-2-yl, 1H-pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl or 1,2,4-triazin-3-yl, which may contain up to two substituents, where the substituents independently of one another are selected from:

substituents at carbon: cyano, fluorine, chlorine, bromine, iodine, methyl, ethyl, 1-methylethyl, 1,1-dimethylethyl, $CF_3$, $CHF_2$, $C_2F_5$, $CCl_3$, cyclopropyl, phenyl, hydroxyl, OMe, OEt, OisoPr, $OCF_3$, $OCHF_2$, $OC_2F_5$, SMe or $SCF_3$, substituents at nitrogen: methyl, ethyl, 1-methylethyl, 1,1-dimethylethyl, cyclopropyl or phenyl, or $R^3$ represents 1H-indol-1-yl, 1H-indol-2-yl, 1H-indol-3-yl, 1H-indol-4-yl, 1H-indol-5-yl, 1H-indol-6-yl, 1H-indol-7-yl, 1H-benzimidazol-1-yl, 1H-benzimidazol-2-yl, 1H-benzimidazol-4-yl, benzimidazol-5-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl, which may contain up to two substituents, where the substituents independently of one another are selected from:

substituents at carbon: cyano, fluorine, chlorine, bromine, iodine, methyl, ethyl, 1-methylethyl, 1,1-dimethylethyl, $CF_3$, $CHF_2$, $C_2F_5$, $CCl_3$, cyclopropyl, phenyl, hydroxyl, OMe, OEt, OisoPr, $OCF_3$, $OCHF_2$, $OC_2F_5$, SMe or $SCF_3$, substituents at nitrogen: methyl, ethyl, 1-methylethyl, 1,1-dimethylethyl, cyclopropyl or phenyl, or $R^3$ represents unsubstituted or monosubstituted pyrrolidin-2-yl, pyrrolidin-3-yl, morpholin-3-yl, morpholin-2-yl, piperidin-2-yl, piperidin-3-yl or piperazin-2-yl, where the substituent is selected from:

substituents at carbon: methyl, ethyl, $CF_3$, cyclopropyl or phenyl, substituents at nitrogen: methyl, ethyl, cyclopropyl or phenyl, $R^8$ are identical or different and independently of one another represent hydrogen, methyl, ethyl or $CF_3$, $R^9$ are identical or different and independently of one another represent hydrogen, methyl or ethyl, or an agrochemically active salt thereof.

4. A compound of formula (I) according to claim 1 in which the symbols have the following meanings, A represents methyl, or A represents phenyl which may contain up to two substituents, where the substituents independently of one another are selected from:

cyano, fluorine, chlorine, bromine, iodine, methyl, ethyl, $CF_3$, $CHF_2$, $C_2F_5$, $CCl_3$ hydroxyl, OMe, $OCF_3$, $OCHF_2$, $OCH_2CF_3$ or $OC_2F_5$, or A represents a heteroaromatic radical selected from the group below: thiophen-3-yl, pyrazol-1-yl, pyrazol-4-yl, pyridin-4-yl, 1H-benzimidazol-2-yl or 1,3-benzothiazol-2-yl, which may contain up to two substituents, where the substituents independently of one another are selected from:

substituents at carbon: cyano, fluorine, chlorine, bromine, iodine, methyl, ethyl, $CF_3$, $CHF_2$, $C_2F_5$, $CCl_3$, hydroxyl, OMe, $OCF_3$, $OCHF_2$, $OCH_2CF_3$ or $OC_2F_5$, substituents at nitrogen: methyl, ethyl or $CF_3$, $L^1$ represents $(C(R^1)_2)_n$ where n=0 to 3, $R^1$ are identical or different and independently of one another represent hydrogen or methyl, with the provision that $L^1$ may contain at most one methyl substituent, Y represents sulphur or oxygen, W represents —CH$_2$CH$_2$—, X represents —CH$_2$CH$_2$—, $R^2$ represents hydrogen, methyl, chlorine or bromine, $L^2$ represents —C($R^8$)$_2$—C($R^8$)$_2$— or —C$R^9$=C$R^9$— or —C≡C—, L³ represents a direct bond,
or
L³ represents a C₁- to C₄-carbon chain,
R³ represents methyl, CF₃, —CH═CH₂, —C≡CH, cyclopropyl, cyclobutyl, cyclopentyl, cyclohexyl, cycloheptyl or cyclooctyl,
or
R³ represents phenyl which may contain up to two substituents, where the substituents independently of one another are selected from:
cyano, fluorine, chlorine, bromine, iodine, methyl, ethyl, 1-methylethyl, 1,1-dimethylethyl, CF₃, CHF₂, C₂F₅, CCl₃, phenyl, hydroxyl, OMe, OEt, OisoPr, OCF₃, OCHF₂, OC₂F₅, SMe or SCF₃,
or
R³ represents naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 1H-inden-2-yl, 1H-inden-3-yl, 1H-inden-4-yl, 1H-inden-5-yl, 1H-inden-6-yl, 1H-inden-7-yl, 2,3-dihydro-1H-inden-1-yl, 2,3-dihydro-1H-inden-2-yl, 2,3-dihydro-1H-inden-4-yl or 2,3-dihydro-1H-inden-5-yl,
or
R³ represents furan-2-yl, furan-3-yl, thiophen-2-yl, thiophen-3-yl, isoxazol-3-yl, isoxazol-4-yl, isoxazol-5-yl, 1H-pyrrol-1-yl, 1H-pyrrol-2-yl, 1H-pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl or 1,2,4-triazin-3-yl,
or
R³ represents 1H-indol-1-yl, 1H-indol-2-yl, 1H-indol-3-yl, 1H-indol-4-yl, 1H-indol-5-yl, 1H-indol-6-yl, 1H-indol-7-yl, 1H-benzimidazol-1-yl, 1H-benzimidazol-2-yl, 1H-benzimidazol-4-yl, benzimidazol-5-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl,
or
R³ represents pyrrolidin-2-yl, pyrrolidin-3-yl, morpholin-3-yl, morpholin-2-yl, piperidin-2-yl, piperidin-3-yl or piperazin-2-yl,
R⁸ are identical or different and independently of one another represent hydrogen, methyl or ethyl,
R⁹ are identical or different and independently of one another represent hydrogen, methyl or ethyl,
or an agrochemically active salt thereof.

5. A method for controlling phytopathogenic harmful fungi, comprising applying a compound of formula (I) according to claim 1 to phytopathogenic harmful fungi and/or a habitat thereof.

6. A composition for controlling phytopathogenic harmful fungi, comprising at least one compound according to claim 1 and an extender and/or a surfactant.

7. A heterocyclyl-substituted thiazoles of formula (I) according to claim 1, in an amount sufficient for controlling phytopathogenic harmful fungi.

8. Process for preparing a composition for controlling phytopathogenic harmful fungi, comprising mixing a heterocyclyl-substituted thiazole of the formula (I) according to claim 1 with an extender and/or a surfactant.

9. A process for preparing a compound of formula (I), comprising at least one of steps (a) to (n) below:

(a) the conversion of compounds of the formula (VII) in the presence of an organometallic compound R⁹-M and, if appropriate, in the presence of a solvent, into compounds of the formula (VIII), according to the reaction scheme below (Scheme 1):

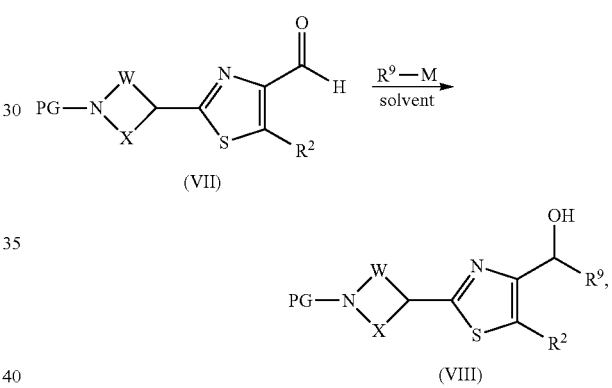

where
PG=unsubstituted or substituted phenylmethyl (where the substituents independently of one another are selected from the group consisting of methyl, methoxy, nitro, dioxolano), acetyl, C₁-C₄-alkoxycarbonyl and benzyloxycarbonyl,
M=for example MgCl, MgBr, MgI, Li,
R⁹=C₁-C₄-alkyl or C₃-C₆-cycloalkyl;

(b) the reaction of alcohols of the formula (VIII) with an oxidizing agent in the presence of a solvent, to give ketones of the formula (IX), according to the reaction scheme below (Scheme 2):

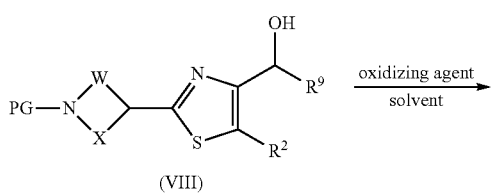

(e) the conversion of aldehydes of the formula (VII) in the presence of a base and, if appropriate, a solvent, into alkynes of the formula (X) according to the reaction scheme below (Scheme 5):

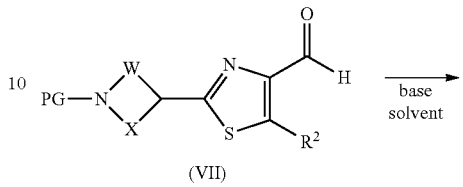

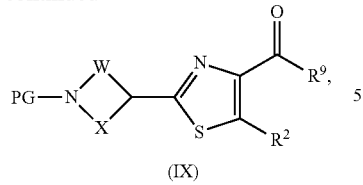

where
PG=unsubstituted or substituted phenylmethyl (where the substituents independently of one another are selected from the group consisting of methyl, methoxy, nitro, dioxolano), acetyl and $C_1$-$C_4$-alkoxycarbonyl,
$R^9$=$C_1$-$C_4$-alkyl or $C_3$-$C_6$-cycloalkyl;
(c) the conversion of ketones of the formula (IX) in the presence of a base or an acid and, if appropriate, a solvent, into compounds of the formula (IVb), according to the reaction scheme below (Scheme 3):

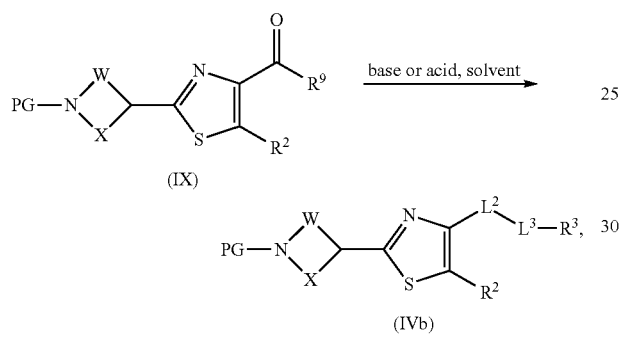

where
PG=unsubstituted or substituted phenylmethyl (where the substituents independently of one another are selected from the group consisting of methyl, methoxy, nitro, dioxolano), acetyl and $C_1$-$C_4$-alkoxycarbonyl;
(f) the reaction of alkynes of the formula (X) with an $R^3$-$L^3$-halide in an optionally catalyzed C—C coupling reaction in the presence of a base and, if appropriate, a solvent, to give compounds of the formula (IVc), according to the reaction scheme below (Scheme 6):

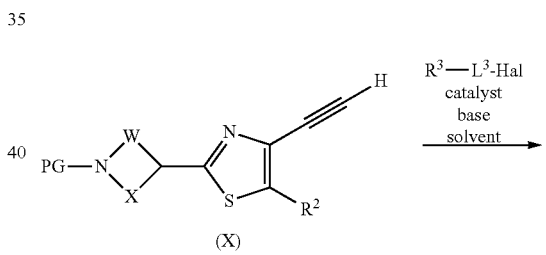

where
PG=unsubstituted or substituted phenylmethyl (where the substituents independently of one another are selected from the group consisting of methyl, methoxy, nitro, dioxolano), acetyl and $C_1$-$C_4$-alkoxycarbonyl,
$L^2$=—$CR^9$=$CR^9$—;
(d) the conversion of aldehydes of the formula (VII) in the presence of a base or an acid and, if appropriate, a solvent, into compounds of the formula (IVb), according to the reaction scheme below (Scheme 4):

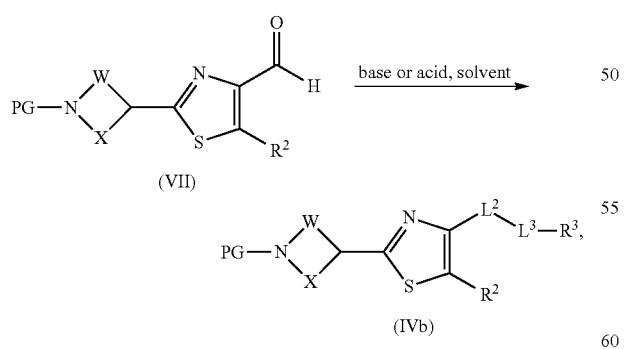

where
PG=unsubstituted or substituted phenylmethyl (where the substituents independently of one another are selected from the group consisting of methyl, methoxy, nitro, dioxolano), acetyl and $C_1$-$C_4$-alkoxycarbonyl,
Hal=Cl, Br or I,
$L^2$=—C≡C—;
(g) the reaction of alkynes of the formula (X) with a trialkylsilyl chloride ($R^{10}R^{11}R^{12}$)SiCl or trialkylsilyl triflate ($R^{10}R^{11}R^{12}$)SiOSO$_2$CF$_3$ or other known silylating agents in the presence of a base and, if appropriate, a solvent, to give compounds of the formula (XI), according to the reaction scheme below (Scheme 7):

where
PG=unsubstituted or substituted phenylmethyl (where the substituents independently of one another are selected from the group consisting of methyl, methoxy, nitro, dioxolano), acetyl and $C_1$-$C_4$-alkoxycarbonyl,
$L^2$=—$CR^9$=$CR^9$—;

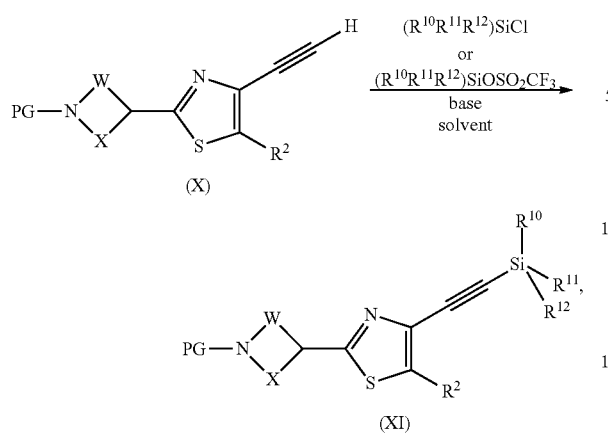

where
PG=unsubstituted or substituted phenylmethyl (where the substituents independently of one another are selected from the group consisting of methyl, methoxy, nitro, dioxolano), acetyl and $C_1$-$C_4$-alkoxycarbonyl,
$R^{10}$, $R^{11}$ and $R^{12}$=$C_1$-$C_4$ alkyl or phenyl;

(h) the reaction of alkynes of the formula (XI) with a compound $R^3$-$L^3$-Hal, if appropriate in the presence of a catalyst, in the presence of a base and, if appropriate, a solvent, to give compounds of the formula (IVc), according to the reaction scheme below (Scheme 8):

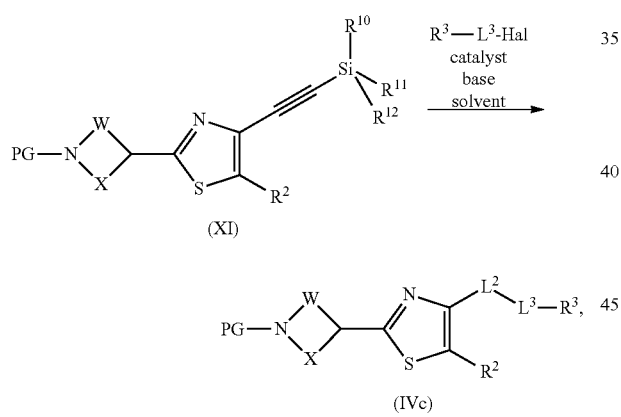

where
PG=unsubstituted or substituted phenylmethyl (where the substituents independently of one another are selected from the group consisting of methyl, methoxy, nitro, dioxolano), acetyl and $C_1$-$C_4$-alkoxycarbonyl,
Hal=Cl, Br or I,
$R^2$=hydrogen, $C_1$-$C_2$-alkyl or $C_1$-$C_2$-haloalkyl,
$L^2$=—C≡C—,
$R^{10}$, $R^{11}$ and $R^{12}$=$C_1$-$C_4$-alkyl or phenyl;

(i) the reaction of thioamides of the formula (V) with compounds of the formula (VIa) or (VIb) in the presence of a base and, if appropriate, in the presence of a solvent, to give compounds of the formula (IVa) or (IVb), according to the reaction scheme below (Scheme 9):

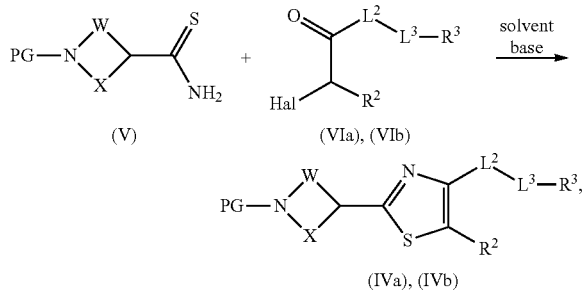

where
PG=unsubstituted or substituted phenylmethyl (where the substituents independently of one another are selected from the group consisting of methyl, methoxy, nitro, dioxolano), acetyl, $C_1$-$C_4$-alkoxycarbonyl and benzyloxycarbonyl,
Hal=Cl, Br or I,
$L^2$=—C($R^8$)$_2$—C($R^8$)$_2$— for compounds of the formula (IVa) and (VIa),
$L^2$=—C$R^9$=C$R^9$— for compounds of the formula (IVb) and (VIb),
W, X, $L^3$, $R^2$, $R^3$, $R^8$ and $R^9$ are as defined for formula (I) in claim 1;

(j) the conversion of compounds of the formula (IVb) or (IVc) in the presence of hydrogen, a catalyst and, if appropriate, a solvent, into compounds of the formula (IVa), according to the reaction scheme below, (Scheme 10):

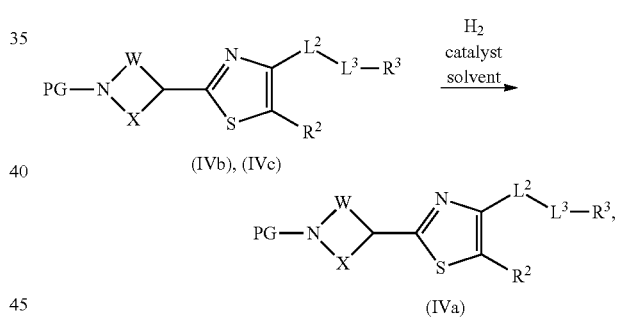

where
PG=acetyl or $C_1$-$C_4$-alkoxycarbonyl,
$L^2$=—C($R^8$)$_2$—C($R^8$)$_2$— for compounds of the formula (IVa),
$L^2$=—C$R^9$=C$R^9$— for compounds of the formula (IVb),
$L^2$=—C≡C— for compounds of the formula (IVc);

(k) the conversion of compounds of the formula (IV), if appropriate in the presence of a solvent and, if appropriate, in the presence of an acid or, if appropriate, in the presence of a base or, if appropriate, in the presence of a source of hydrogen, into compounds of the formula (II), according to the reaction scheme below (Scheme 11):

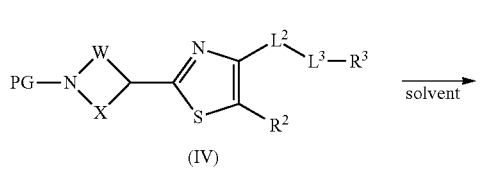

-continued

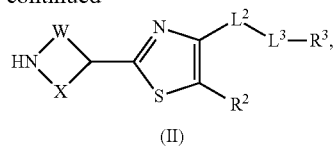
(II)

where

PG=acetyl, $C_1$-$C_4$-alkoxycarbonyl or benzyloxycarbonyl;

(l) the conversion of compounds of the formula (IIa') in the presence of a halogenating agent, if appropriate in the presence of an acid and a solvent, into compounds of the formula (IIa), according to the reaction scheme below (Scheme 12):

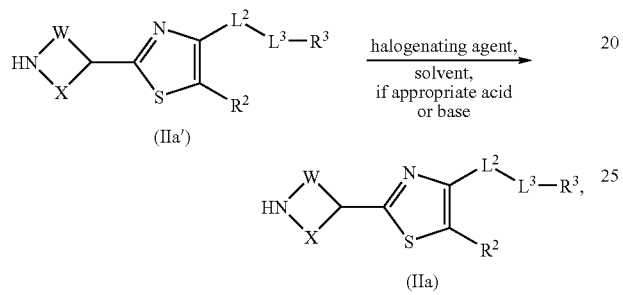

where $L^2 = -C(R^8)_2-C(R^8)_2-$, $R^2$=I, Br or Cl for compounds of the formula (IIa), $R^2$=hydrogen for compounds of the formula (IIa');

(m) the reaction of compounds of the formula (III) with compounds of the formula (II), if appropriate in the presence of a coupling agent, a base and a solvent, to give compounds of the formula (I), according to the reaction scheme below (Scheme 13):

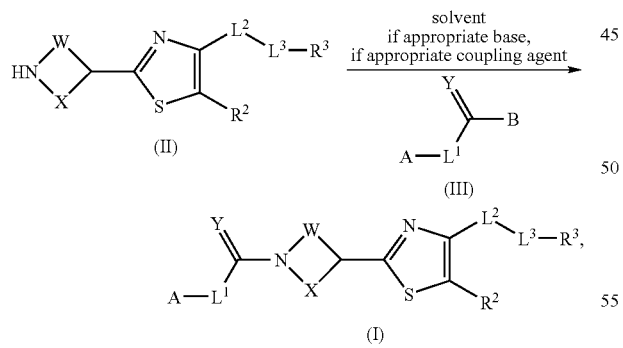

where

B=OH, chlorine, bromine or iodine,

Y=oxygen;

(n) the conversion of compounds of the formula (I) in the presence of a sulphurizing agent and, if appropriate, in the presence of a solvent, into compounds of the formula (I), according to the reaction scheme below (Scheme 14):

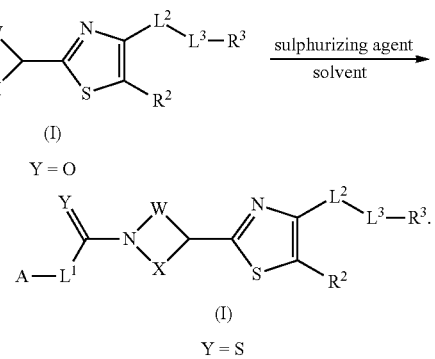

10. Process for preparing the compounds of the formula (I) according to claim 1, comprising at least one of steps (o) to (u) below:

(o) the conversion of aldehydes of the formula (XII) in the presence of a base and, if appropriate, a solvent, into alkynes of the formula (XIII), according to the reaction scheme below (Scheme 17):

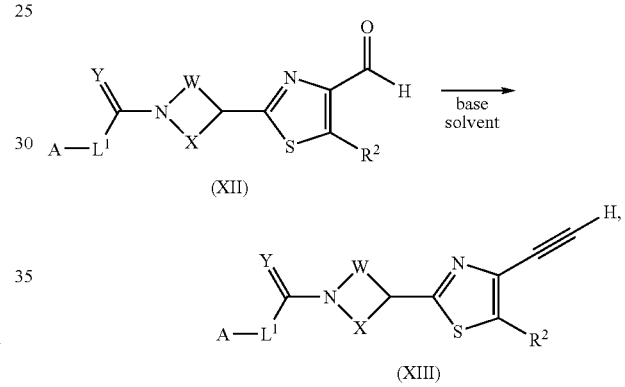

(p) the reaction of alkynes of the formula (XIII) with a trialkylsilyl chloride $(R^{10}R^{11}R^{12})SiCl$ or trialkylsilyl triflate $(R^{10}R^{11}R^{12})SiOSO_2CF_3$ or other known silylating agents in the presence of a base and, if appropriate, a solvent, to give compounds of the formula (XIV), according to the reaction scheme below (Scheme 18):

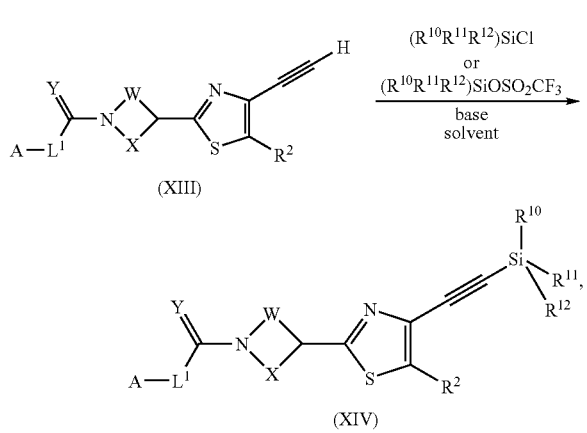

where $R^{10}$, $R^{11}$ and $R^{12}$=$C_1$-$C_4$ alkyl or phenyl;

(q) the reaction of alkynes of the formula (XIII) with an R³-L³-halide in an optionally catalyzed C—C coupling reaction in the presence of a base and, if appropriate, a solvent, to give compounds of the formula (Ic), according to the reaction scheme below (Scheme 19):

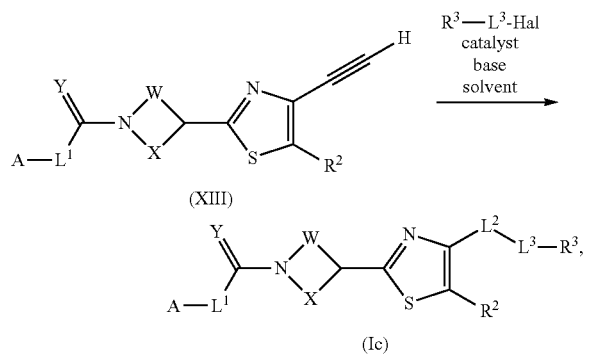

where
Hal=Cl, Br or I,
L²=—C≡C—;

(r) the reaction of alkynes of the formula (XIV) with a compound R³-L³-Hal, if appropriate in the presence of a catalyst, in the presence of a base and, if appropriate, a solvent, to give compounds of the formula (Ic), according to the reaction scheme below (Scheme 20):

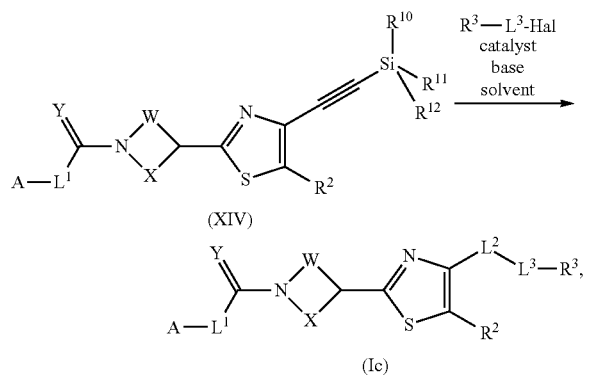

where
Hal=Cl, Br or I,
L²=—C≡C—,
R¹⁰, R¹¹ and R¹²=C₁-C₄-alkyl or phenyl;

(s) the conversion of aldehydes of the formula (XII) in the presence of a base or an acid and, if appropriate, a solvent, into compounds of the formula (Ib), according to the reaction scheme below (Scheme 21):

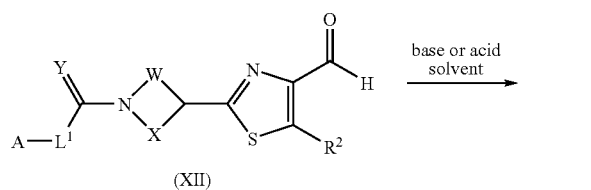

-continued

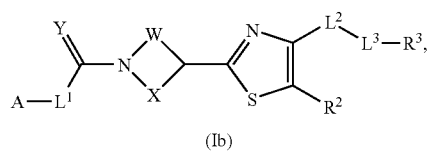

where
L²=—CR⁹=CR⁹—;

(t) the conversion of compounds of the formula (Ic) in the presence of hydrogen, a catalyst and, if appropriate, a solvent, into compounds of the formula (Ib), according to the reaction scheme below (Scheme 22):

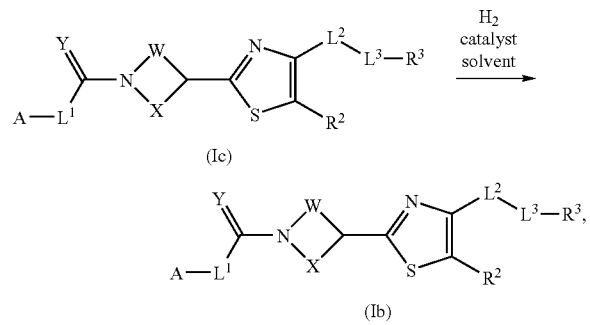

where
L²=—CR⁹=CR⁹— for compounds of the formula (Ib),
L²=—C≡C— for compounds of the formula (Ic);

(u) the conversion of compounds of the formula (Ib) or (Ic) in the presence of hydrogen, a catalyst and, if appropriate, a solvent, into compounds of the formula (Ia), according to the reaction scheme below (Scheme 23):

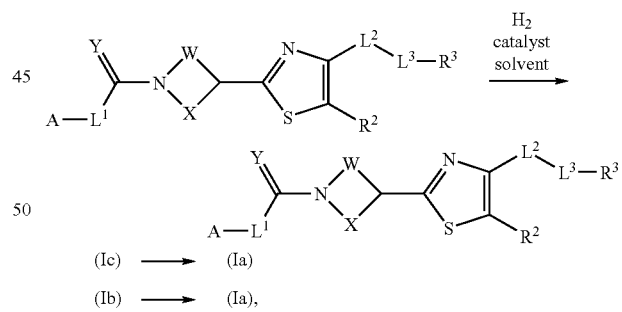

(Ic) ⟶ (Ia)
(Ib) ⟶ (Ia), where
L²=—C(R⁸)₂—C(R⁸)₂— for compounds of the formula (Ia),
L²=—CR⁹=CR⁹— for compounds of the formula (Ib),
L²=—C≡C— for compounds of the formula (Ic).

* * * * *